United States Patent
Singh et al.

(10) Patent No.: US 11,660,350 B2
(45) Date of Patent: *May 30, 2023

(54) ANTIBACTERIAL PRODUCTS

(71) Applicant: UNIVERSITY OF LINCOLN, Lincoln (GB)

(72) Inventors: Ishwar Singh, Lincoln (GB); Edward Taylor, Lincoln (GB)

(73) Assignee: UNIVERSITY OF LINCOLN, Lincoln (GB)

( * ) Notice: Subject to any disclaimer, the term of this patent is extended or adjusted under 35 U.S.C. 154(b) by 240 days.

This patent is subject to a terminal disclaimer.

(21) Appl. No.: 15/508,651

(22) PCT Filed: Sep. 4, 2015

(86) PCT No.: PCT/GB2015/052564
§ 371 (c)(1),
(2) Date: Mar. 3, 2017

(87) PCT Pub. No.: WO2016/034894
PCT Pub. Date: Mar. 10, 2016

(65) Prior Publication Data
US 2018/0147290 A1    May 31, 2018

(30) Foreign Application Priority Data
Sep. 5, 2014 (GB) ..................... 1415776

(51) Int. Cl.
| | | |
|---|---|---|
| *A61K 47/64* | (2017.01) | |
| *C07C 277/08* | (2006.01) | |
| *A61K 38/14* | (2006.01) | |
| *C07C 271/20* | (2006.01) | |
| *C07C 279/12* | (2006.01) | |
| *A61K 38/16* | (2006.01) | |
| *C07H 13/00* | (2006.01) | |
| *A61K 47/59* | (2017.01) | |
| *A61P 31/04* | (2006.01) | |
| *A61K 31/7034* | (2006.01) | |
| *A61K 31/7056* | (2006.01) | |

(52) U.S. Cl.
CPC .......... *A61K 47/64* (2017.08); *A61K 31/7034* (2013.01); *A61K 31/7056* (2013.01); *A61K 38/14* (2013.01); *A61K 38/164* (2013.01); *A61K 47/59* (2017.08); *A61P 31/04* (2018.01); *C07C 271/20* (2013.01); *C07C 277/08* (2013.01); *C07C 279/12* (2013.01); *C07H 13/00* (2013.01)

(58) Field of Classification Search
None
See application file for complete search history.

(56) References Cited

U.S. PATENT DOCUMENTS

| | | |
|---|---|---|
| 8,604,004 B2 | 12/2013 | Kahne et al. |
| 2004/0127403 A1 | 7/2004 | Parenti et al. |
| 2009/0203641 A1 | 8/2009 | Wong et al. |
| 2014/0018435 A1 | 1/2014 | Hong et al. |

FOREIGN PATENT DOCUMENTS

| | | | |
|---|---|---|---|
| EP | 1155623 | 11/2001 | |
| WO | WO 2002-036612 | 5/2002 | |
| WO | WO-0236612 A1 * | 5/2002 | ............ C07K 9/008 |
| WO | WO 2004-009665 | 1/2004 | |
| WO | WO2004/009665 | 1/2004 | |
| WO | WO 2004-017925 | 3/2004 | |
| WO | WO2007/087256 | 8/2007 | |
| WO | WO2007/099396 | 9/2007 | |
| WO | WO 2007-138047 | 12/2007 | |
| WO | WO 2009-046314 | 4/2009 | |
| WO | WO2010/011304 | 1/2010 | |
| WO | WO 2010-147831 | 12/2010 | |
| WO | WO2010/147831 | 12/2010 | |
| WO | WO 2013-063405 | 5/2013 | |

OTHER PUBLICATIONS

Tschiche et al. "Polyglycerol-based amphiphilic dendrons as potential siRNA carriers for in vivo applications" J. Materials Chemistry B 2:2153-2167. (Year: 2014).*
El-Abadla et al. "Moenomycin A: The Role of the Methyl Group in the Moenuronamide Unit and a General Discussion of Structure-Activity Relationships" Tetrahedron 55:699-722. (Year: 1999).*
Cheng et al. "Domain requirement of moenomycin binding to bifunctional transglycosylases and development of high-throughput discovery of antibiotics" Proc. Natl. Acad. Sci. 105:431-436. (Year: 2008).*
Patenge et al. "Inhibition of Growth and Gene Expression by PNA-peptide Conjugates in *Streptococcus pyogenes*" Molecular Therapy—Nucleic Acids 2:e132. (Year: 2013).*
Afifi et al., "Antimicrobial activity of furazolidone and some growth-promoters," *Veterinary Medical Journal Giza*, 37:299-311 (Abstract only), 1989.
Alex et al., "Amino-acid derived 1,2-benzisothiazolinone derivatives as novel small molecule antifungal inhibitors: identification of potential genetic targets," *Antimicrob. Agents Chemother.*, 56:4630-4639, 2012.
Arnusch et al., "Enhanced membrane pore formation through high-affinity targeted antimicrobial peptides," *PLoS One*, 7:e39768, 2012.

(Continued)

*Primary Examiner* — Sudhakar Katakam
*Assistant Examiner* — Zachary J Miknis
(74) *Attorney, Agent, or Firm* — Parker Highlander PLLC

(57) ABSTRACT

The invention provides a combination of an antibacterial agent (in particular vancomycin or moenomycin) and a delivery agent, in which the delivery agent is bonded, or capable of binding, to the antibacterial agent, and in which the delivery agent is capable of binding to one or more structures on a bacterial cell membrane. The invention further provides the use of such combinations in treating or preventing bacterial infections.

Figure 1:
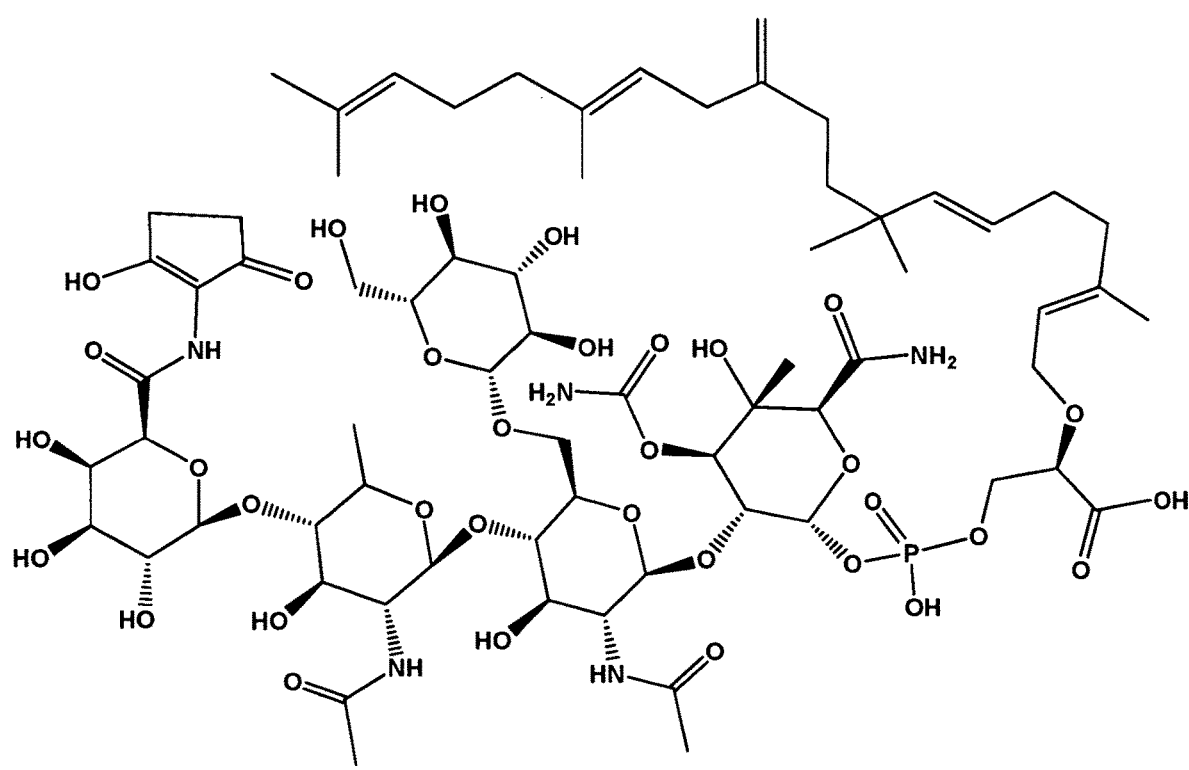

19 Claims, 2 Drawing Sheets
Specification includes a Sequence Listing.

(56) References Cited

OTHER PUBLICATIONS

Barnes et al., "Factors affecting the incidence and anti-salmonella activity of the anaerobic caecal flora of the young chick," *J. Hyg. Camb.*, 82:263-283, 1979.
Batty et al., "The effect of relative humidity on swine vesicular disease virus in dried films before and during formaldehyde fumigation," *J. Hyg. Camb.*, 82:255-261, 1979.
Beck et al., "Dietary balance of sodium, potassium, and chloride influences plasma uric acid concentrations in chicks," *Poultry Sci.*, 59:1197-1202 (Abstract only), 1980.
Calabretta et al., "Antibacterial activities of poly (amidoamine) dendrimers terminated with amino and poly (ethylene glycol) groups," Biomacromolecules, 8:1807-1811, 2007.
Cheng et al., "Domain requirement of moenomycin binding to bifunctional transglycosylases and development of high-throughput discovery of antibiotics," *PNAS*, 105:431-436, 2008.
Choi et al., "Dendrimer-Based Multivalent Vancomycin Nanoplatform for Targeting the Drug-Resistant Bacterial Surface," *ACS Nano*, 7:214-228, 2013.
Durairaj at al., "Nanosized dendritic polyguanidilyated translocators for enhanced solubility, permeability, and delivery of gatifloxacin," *Invest. Ophthalmol. Vis. Sci.*, 51:5804, 2010.
El-Abadla et al., "Moenomycin A: The role of the methyl group in the moenuronamide unit and a general discussion of structure-activity relationships," *Tetrahedron*, 55:699-722, 1999.
Falagas et al., "Toxicity of polymyxins: a systematic review of the evidence from old and recent studies," *Critical Care*, 10(R27):1-13, 2006.
Gardiner et al., "PAMAM dendrimers for the delivery of the antibacterial triclosan," *J. Enzyme Inhib. Med. Chem.*, 23:623-628, 2008.
Gemmell et al., "Role of certain virulence factors in a murine model of *Staphylococcus aureus* arthritis," *J. Med. Microbiol.*, 46:208-213, 1997.
Geukens et al., "Membrane topology of the *Streptomyces lividans* type I signal peptidases," *J. Bacteriol.*, 183:4752-4760, 2001.
International Preliminary Report on Patentability issued in corresponding PCT Application No. PCT/GB2015/052564, dated Mar. 7, 2017.
International Search Report and Written Opinion issued in corresponding PCT Application No. PCT/GB2015/052564, dated Feb. 29, 2016.
Khalaf et al., "Distamycin analogues with enhanced lipophilicity: synthesis and antimicrobial activity," *J. Med. Chem.*, 47:2133-2156, 2004.
Linnett et al., "Additional antibiotic inhibitors of peptidoglycan synthesis," *Antimicrob. Agents Chemother.*, 4:231-236 (Abstract only), 1973.
Mamber et al., "Effects of antimicrobial agents fed to chickens on some gram-negative enteric bacilli," *Applied Microbiology*, 50:638-648 (Abstract only), 1985.
Ohno et al., "In vitro and in vivo activity of penicillinase inhibitor KA-107 against *Staphylococcus aureus* FS-1277," *Antimicrob. Agents Chemother.*, 4:226-230, 1973.
Ostash et al., "Moenomycin family antibiotics: chemical synthesis, biosynthesis, and biological activity," *Nat. Prod. Rep.*, 27:1594-1617, 2010.
Page, "Siderophore conjugates," *Ann. N. Y. Acad. Sci.*, 1277:115, 2013.
Pfaller, "Flavophospholipol use in animals: Positive implications for antimicrobial resistance based on its microbiologic properties," *Diagn. Mier. Infec. Dis.*, 56:115-121, 2006.
Shepherd et al., "Hyperbranched poly (NIPAM) polymers modified with antibiotics for the reduction of bacterial burden in infected human tissue engineered skin," *Biomaterials*, 32:258, 2011.
Sierks et al., "Application of Cross-Linked Carboxymethyl Cellulose Degradation by [beta]-Glucosidase and Vaginal Microbes to Toxic Shock Syndrome," *Applied Microbiology*, 50:634-637, 1985.
Son et al., "Bioreducible polymers for gene silencing and delivery," *Acc. Chem. Res.*, 45:1100-1112, 2012.
Sorgeloos et al., "New Type of Turbidostat with Intermittent Determination of Cell Density Outside the Culture Vessel," *Applied Microbiology*, 31:327-331, 1976.
Taylor et al., "The total synthesis of moenomycin A," *J. Am. Chem. Soc.*, 128:15084-15085, 2006.
Taylor, "Problems and Progress in Complex Oligosaccharide Synthesis: The Total Synthesis of Moenomycin A," Ph.D. Thesis, Harvard University, 2006.
Therien et al., "Broadening the spectrum of [beta]-lactam anitbiotics thorugh inhibition of signal peptidase type I," *Antimicrob. Agents Chemother.*, 56:4662-4670 (Abstract only), 2012.
Tschiche et al., "Polyglycerol-based amphiphilic dendrons as potential siRNA carriers for in vivo applications," *J. Mater. Chem. B*, 2:2153-2167, 2014.
Tseng et al., "Development of bacterial transglycosylase inhibitors as new antibiotics: Moenomycin A treatment for drug-resistant Helicobacter pylori," *Bioorganic Med. Chem. Lett.*, 24:2412-2414, 2014.
Typas et al., "From the regulation of peptidoglycan synthesis to bacterial growth and morphology," *Nat. Rev. Microbiol*, 10:123-136, 2012.
Van Dijck et al., "Sensitivity of environmental microorganisms to antimicrobial agents," *Applied Microbiology.*, 31:332-336 (Abstract only), 1976.
Venturelli et al., "Optimizing cell permeation of an antibiotic resistance inhibitor for improved efficacy," *J. Med. Chem.*, 50:5644-5654, 2007.
Wallhaeusser et al., "Moenomycin, a new antibiotic: I. Fermentation and isolation," *Antimicrob. Agents Chemother.*, 734-736 (Abstract only), 1965.
Wang et al., "Identification and characterization of a monofunctional glycotransferase from *Staphylococcus aureus*," *J. Bacteriol.*, 183:4779-4785 (Abstract only), 2001.
Welzel, "A long research story culminates in the first total synthesis of moenomycin A," *Angew. Chem., Int. Ed.*, 46:4825-4829, 2007.
Wesolowski et al., "Basic peptide-morpholino oligomer conjugate that is very effective in killing bacteria by gene-specific and nonspecific modes," *PNAS*, 108:16582-16587, 2011.
Wesolowski et al., "Combined effect of a peptide-morpholino oligonucleotide conjugate and a cell-penetrating peptide as an antibiotic," *PNAS*, 110:8686-8689, 2013.
Xue et al., "Amino-terminated generation 2 poly (amidoamine) dendrimer as a potential broad-spectrum, nonresistance-inducing antibacterial agent," *AAPS J.*, 15:132-142, 2013.
Yuan et al., "Structural Analysis of the Contacts Anchoring Moenomycin to Peptidoglycan Glycotransferases and Implications for Antibiotic Design," *ACS Chem. Biol.*, 3:429-436, 2008.
Zheng et al., "Siderophore-Mediated Cargo Delivery to the Cytoplasm of *Escherichia coli* and Pseudomonas aeruginosa: Syntheses of Monofunctionalized Enterobactin Scaffolds and Evaluation of Enterobactin—Cargo Conjugate Uptake," *J. Am. Chem. Soc.*, 134:18388, 2012.
Zasloff, Michael. "Antimicrobial peptides of multicellular organisms." *Nature* 415.6870 (2002): 389-395.
Madaan, Kanika, et al. "Dendrimers in drag delivery and targeting: Drug-dendrimer interactions and toxicity issues." *Journal of Pharmacy & Bioallied Sciences* 6.3 (2014): 139.
Sato, Katsuhiko, and Jun-ichi Anzai. "Dendrimers in layer-by-layer assemblies: synthesis and applications." *Molecules* 18.7 (2013): 8440-8460.
Zhu, Jingyi, and Xiangyang Shi. "Dendrimer-based nanodevices for targeted drug delivery applications." *Journal of Materials Chemistry B* 1.34 (2013): 4199-4211.
"Amino Acid." *Wikipedia*, Wikimedia Foundation, Nov. 13, 2020, https://en.wikipedia.org/w/index.php?title=Amino_acid&oldid=988424009.
"Amino acid", Wikipedia, page last edited on Nov. 13, 2020, pp. 1-14, XP055927482, Retrieved from the Internet: URL:https://en.wikipedia.org/w/index,php?title=Amino_acid&oldid=988424009 [retrieved on Jun. 2, 2022].

(56) References Cited

OTHER PUBLICATIONS

Calabretta et al., "*Antibacterial Activities of Poly (amidoamine) Dendrimers Terminated with Amino and Poly (ethylene glycol) Groups*", Biomacromelecules, vol. 8, No. 6, Jun. 2007, pp. 1807-1811.
Dose et al., "*Facile synthesis of colorimetric histone deacetylase ubstrates*", Chemical Communications, vol. 48, No. 76, Jan. 2012, p. 9525.
Falagas et al., "*Toxicity of polymyxins: a. systematic review of the evidence form old and recent studies*", Critical, Care, vol. 10, No. 1, p. R27, published Feb. 13, 2006.
Gardiner et al., "*PAMAM dendrimers for the delivery of the antibacterial Triclosan*", Joutnal of Enzyme Inhibition and Medicinal, Chemistry, vol. 23, No. 5, Jan. 2008, pp. 623-628.
Nadja et al., "*Inhibition of Growth and Gene Expression by PNA-peptide Conjugates in Streptococcus pyogenes*", Molecular Therapy-Nucleic Acids, vol. 2, Jan. 2013, pp. 2153-2167.
Tschiche et al., "*Polyglycerol-based amphiphilic dendrons as potential siRNA carriers for in vivo applications*". Journal of Materials Chemistry. B, vol. 2. No. 15, Jan. 2014, pp. 2153-2167.
Xiaoyan et al., "*Amino-Terminated Generation 2 Poly (amidoamine) Dendrimer as a Potential Broad-Spectrum, Nonresistance-Inducing Antibacterial Agent*", The AAPS Springer US, Boston, vol. 15, No. 1, Nov. 8, 2012, pp. 132-142,.

\* cited by examiner

SEQUENCE LISTING

```
<160> NUMBER OF SEQ ID NOS: 37

<210> SEQ ID NO 1
<211> LENGTH: 8
<212> TYPE: PRT
<213> ORGANISM: Artificial Sequence
<220> FEATURE:
<223> OTHER INFORMATION: Synthetic peptide sequence

<400> SEQUENCE: 1

Arg Arg Arg Arg Arg Arg Arg Arg
1               5

<210> SEQ ID NO 2
<211> LENGTH: 13
<212> TYPE: PRT
<213> ORGANISM: Artificial Sequence
<220> FEATURE:
<223> OTHER INFORMATION: Synthetic peptide sequence

<400> SEQUENCE: 2

Lys Pro Leu Ile Tyr Leu Leu Arg Leu Arg Gly Gln Phe
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Synthetic peptide sequence

<400> SEQUENCE: 3
```

```
Lys Pro Leu Ile Tyr Leu Leu Leu Arg Arg Gly Gln Phe
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 4

Lys Arg Arg Lys Arg Arg Lys Arg Arg
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 5

Lys Arg Arg Arg Arg Arg Arg
1               5

<210> SEQ ID NO 6
<211> LENGTH: 12
<212> TYPE: PRT
<213> ORGANISM: Artificial Sequence
<220> FEATURE:
<223> OTHER INFORMATION: Synthetic peptide sequence

<400> SEQUENCE: 6

Pro Leu Ile Tyr Leu Lys Leu Leu Lys Gly Gln Phe
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 7

Arg Arg Arg Arg Arg Arg Arg
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 8

Pro Leu Ile Tyr Leu Leu Gly Arg Arg
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 9

Pro Leu Ile Tyr Leu Leu Arg Gly Arg
```

```
<210> SEQ ID NO 10
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 10

Pro Leu Ile Tyr Leu Leu Lys Gly Arg
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 11

Pro Leu Ile Tyr Leu Leu Arg Gly Lys
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 12

Pro Leu Ile Tyr Leu Leu Lys Gly Lys
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 13

Pro Leu Ile Tyr Leu Lys Leu Leu Lys
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic peptide sequence

<400> SEQUENCE: 14

Lys Lys Lys Lys Lys Arg
1               5

<210> SEQ ID NO 15
<211> LENGTH: 4
<212> TYPE: PRT
<213> ORGANISM: Artificial Sequence
<220> FEATURE:
<223> OTHER INFORMATION: Synthetic peptide sequence

<400> SEQUENCE: 15

Arg Arg Arg Arg
1
```

<210> SEQ ID NO 16
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 16

Arg Arg Arg Arg Arg Arg Arg Arg Arg
1               5

<210> SEQ ID NO 17
<211> LENGTH: 10
<212> TYPE: PRT
<213> ORGANISM: Artificial Sequence
<220> FEATURE:
<223> OTHER INFORMATION: Synthetic peptide sequence

<400> SEQUENCE: 17

Arg Arg Arg Arg Arg Arg Arg Arg Arg Arg
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Synthetic peptide sequence

<400> SEQUENCE: 18

Lys Lys Arg Arg Arg Arg Arg Arg Arg Arg
1               5                   10

<210> SEQ ID NO 19
<211> LENGTH: 8
<212> TYPE: PRT
<213> ORGANISM: Artificial Sequence
<220> FEATURE:
<223> OTHER INFORMATION: Synthetic peptide sequence

<400> SEQUENCE: 19

Lys Lys Arg Lys Lys Lys Lys Arg
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 20

Arg Arg Trp Trp Arg Arg Trp Arg Arg
1               5

<210> SEQ ID NO 21
<211> LENGTH: 12
<212> TYPE: PRT
<213> ORGANISM: Artificial Sequence
<220> FEATURE:
<223> OTHER INFORMATION: Synthetic peptide sequence

<400> SEQUENCE: 21

Pro Leu Ile Tyr Leu Arg Leu Leu Arg Gly Gln Phe
1               5                   10

```
<210> SEQ ID NO 22
<211> LENGTH: 13
<212> TYPE: PRT
<213> ORGANISM: Artificial Sequence
<220> FEATURE:
<223> OTHER INFORMATION: Synthetic peptide sequence

<400> SEQUENCE: 22

Phe Gln Gly Arg Leu Arg Leu Leu Tyr Ile Leu Pro Lys
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Synthetic peptide sequence

<400> SEQUENCE: 23

Phe Gln Gly Arg Arg Leu Leu Leu Tyr Ile Leu Pro Lys
1               5                   10

<210> SEQ ID NO 24
<211> LENGTH: 7
<212> TYPE: PRT
<213> ORGANISM: Artificial Sequence
<220> FEATURE:
<223> OTHER INFORMATION: Synthetic peptide sequence

<400> SEQUENCE: 24

Arg Arg Arg Arg Arg Arg Lys
1               5

<210> SEQ ID NO 25
<211> LENGTH: 12
<212> TYPE: PRT
<213> ORGANISM: Artificial Sequence
<220> FEATURE:
<223> OTHER INFORMATION: Synthetic peptide sequence

<400> SEQUENCE: 25

Phe Gln Gly Lys Leu Leu Lys Leu Tyr Ile Leu Pro
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Synthetic peptide sequence

<400> SEQUENCE: 26

Phe Gln Gly Arg Leu Leu Arg Leu Tyr Ile Leu Pro
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Synthetic peptide sequence

<400> SEQUENCE: 27

Phe Gln Gly Arg Leu Arg Leu Leu Tyr Ile Leu Pro
1               5                   10
```

<210> SEQ ID NO 28
<211> LENGTH: 12
<212> TYPE: PRT
<213> ORGANISM: Artificial Sequence
<220> FEATURE:
<223> OTHER INFORMATION: Synthetic peptide sequence

<400> SEQUENCE: 28

Phe Gln Gly Arg Arg Leu Leu Leu Tyr Ile Leu Pro
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Synthetic peptide sequence

<400> SEQUENCE: 29

Lys Pro Leu Ile Tyr Leu Arg Leu Leu Arg Gly Gln Phe
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Synthetic peptide sequence

<400> SEQUENCE: 30

Phe Gln Gly Arg Leu Leu Arg Leu Tyr Ile Leu Pro Lys
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Synthetic peptide sequence

<400> SEQUENCE: 31

Arg Arg Arg Arg Arg Arg Arg Arg Lys Lys
1               5                   10

<210> SEQ ID NO 32
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 32

Arg Arg Lys Arg Arg Lys Arg Arg Lys
1               5

<210> SEQ ID NO 33
<211> LENGTH: 6
<212> TYPE: PRT
<213> ORGANISM: Artificial Sequence
<220> FEATURE:
<223> OTHER INFORMATION: Synthetic peptide sequence

```
<400> SEQUENCE: 33

Arg Lys Lys Lys Lys Lys
1               5

<210> SEQ ID NO 34
<211> LENGTH: 8
<212> TYPE: PRT
<213> ORGANISM: Artificial Sequence
<220> FEATURE:
<223> OTHER INFORMATION: Synthetic peptide sequence

<400> SEQUENCE: 34

Arg Lys Lys Lys Lys Arg Lys Lys
1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic peptide sequence

<400> SEQUENCE: 35

Arg Arg Trp Arg Arg Trp Trp Arg Arg
1               5

<210> SEQ ID NO 36
<211> LENGTH: 12
<212> TYPE: PRT
<213> ORGANISM: Artificial Sequence
<220> FEATURE:
<223> OTHER INFORMATION: Synthetic peptide sequence

<400> SEQUENCE: 36

Pro Leu Ile Tyr Leu Leu Arg Leu Arg Gly Gln Phe
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Synthetic peptide sequence

<400> SEQUENCE: 37

Pro Leu Ile Tyr Leu Leu Leu Arg Arg Gly Gln Phe
1               5                   10
```

ANTIBACTERIAL PRODUCTS

This application is a national phase application under 35 U.S.C. § 371 of International Application No. PCT/GB2015/052564, filed Sep. 4, 2015, which claims benefit of United Kingdom Application No. 1415776.2, filed Sep. 5, 2014, the entire contents of each of which are hereby incorporated by reference.

FIELD OF THE INVENTION

This invention relates to delivery agents that have affinity for bacterial cell walls, and combinations comprising such delivery agents together with antibacterial agents for treating and preventing bacterial infections.

BACKGROUND

We are currently facing a worldwide pandemic of multi-drug resistant bacteria, arising from the long-term use of antibacterials. Antibacterial overavailability and poor prescribing practices have allowed exposure to sub-optimal concentrations of antibacterials, promoting the evolution of environmental resistance mechanisms in bacteria.

There is therefore a continuing need to develop new ways of combating unwanted bacterial growth, particularly in bacteria that are resistant to existing drugs.

Some existing drugs target enzymes that are involved in the construction of bacterial cell walls. The bacterial cell wall is assembled by a glycosyltransferase (GT51) (cazy-.org/GT51.html) and transpeptidase (TP) enzymes, which together catalyse the bond formation in the important cell wall polymer peptidoglycan. This is a mesh-like structure and is responsible for bacterial shape and strength. Due to their periplasmic location and lack of mammalian counterpart, both the GT51 and TP are excellent targets for inhibition. Indeed the transpeptidase is inhibited by the medically important β-lactam group of antibacterials. The GT51 domains are membrane associated and catalyse the polymerisation of a lipid II pentapeptide substrate into b1,4-linked N-acetylmuramic acid, N-acetylglucosamine polymers [(MurNAc-GlcNAc)n] (Types A., et al., *Nat Rev Microbiol*, 10, 123-136).

The GT51 enzymes are inhibited by moenomycins which cause accumulation of cell-wall intermediates leading to bacterial cell lysis and death. It is the only class of antibacterial which inhibits the GT51 enzyme. Moenomycins are extremely potent with minimal inhibitory concentration (MIC) against various Gram positive bacteria ranging from 1 ng/ml-100 ng/ml biological activity and is 10-1000 fold more potent than clinically useful glycopeptide vancomycin.

Bambermycin (also known as flavomycin, flavophospholipol) is a phosphoglycolipid antimicrobial produced by various strains of *Streptomyces*. Moenomycin A is a component of Bambermycin. It is active primarily against Gram-positive bacteria due to inhibition of transglycosylase and thus of cell wall synthesis (Pfaller M. A., et al. *Diagnostic Microbiology and Infectious Disease* 56 (2006) 115-121).

The antimicrobial spectrum of flavophospholipol is known to be limited. Both fermentative (e.g. Enterobacteriaceae) and nonfermentative (e.g., *Pseudomonas* spp.) Gram-negative bacilli are considered to be inherently resistant to flavophospholipol. It is believed that flavophospholipol is unable to penetrate the outer membrane of Gram-negative organisms and thus is unable to reach the target elements in these organisms (Pfaller M. A., ibid.).

Despite their potency, interest in developing moenomycins as novel drugs dissipated because of their poor bioavailability and suboptimal pharmacokinetic properties. (Ostash B. et al. *Nat. Prod, Rep.*, 2010, 27, 1594-1617). Moenomycins show almost no curative or protective effects and no toxicity via the oral route, reflecting their extremely low absorption from the gastrointestinal tract. Moenomycin has a very long halflife in the bloodstream, some hemolytic activity and it is not orally bioavailable. Nevertheless, moenomycins have been successfully commercialised as animal growth promoters.

Ting-Jen et al. *PNAS*, 105, 2, 431-436 (2008) discusses the interactions between moenomycin and the penicillin binding proteins. However, there is no discussion of how the poor bioavailability and suboptimal pharmacokinetic properties of moenomycin may be overcome.

El-Abadla N. et al., *Tetrahedron* 55 (1999) 699-722 discloses the combination of moenomycin A with a cyclic polypeptide molecule. The polypeptide molecule is believed to disorganise the outer membrane of the target cells, however the potential for the polypeptide to similarly disrupt a host organism's cells and thereby be toxic to the host organism is not addressed. The toxicity of polymyxin was reported in Falagas M. E. et al. *Critical Care* (2006) Vol 10, No. 1, 1-13.

The listing or discussion of a prior-published document in this specification should not necessarily be taken as an acknowledgement that the document is part of the state of the art or is common general knowledge.

DESCRIPTION OF THE INVENTION

According to the invention, there is provided a series of novel compositions of matter comprising a combination of an antibacterial agent and a delivery agent. The combinations have been developed in order to allow new and existing antibacterial agents, some of which may previously have been considered to be insufficiently active in the clinic, to be useful in treating and preventing bacterial infections. The approach involves the synthesis and use of new delivery agents which are capable of binding to both the antibacterial agent and certain components of a bacterial cell, thereby acting as an anchor for the antibacterial agent and significantly increasing its effectiveness.

According to a first aspect of the invention, there is provided a combination of an antibacterial agent and a delivery agent, wherein:

(i) the delivery agent is a moiety that is covalently bonded to the antibacterial agent, and wherein the delivery agent is either capable of covalently bonding to one or more structures on a bacterial cell membrane or comprises a hydrophilic portion capable of otherwise binding (e.g. by way of electrostatic interactions (i.e. ionic interactions) and/or hydrogen bonding) to one or more structures on a bacterial cell membrane;

(ii) the delivery agent is a compound of formula I,

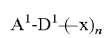
$$A^1\text{-}D^1\text{-}(\text{-}X)_n \qquad \qquad I$$

or a pharmaceutically-acceptable salt thereof, wherein $A^1$ represents a hydrogen atom or a terminating group; $D^1$ represents a dendrimer fragment to which the X groups shown are attached, X represents —NH$_2$, boronic acid or a boronic acid derivative; and n is 2 or more (e.g. from 2 to 20); or (iii) the delivery agent is a polypeptide or a polypeptide derivative, or a pharmaceutically-acceptable salt thereof, that comprises at least two amino acid residues selected from the group consisting of arginine and lysine, and is capable of otherwise binding to one or more structures on a bacterial cell membrane.

Such combinations are hereinafter referred to as "compositions of the invention".

In one embodiment, the composition is a combination of an antibacterial agent and a delivery agent, wherein:
(i) the delivery agent is a moiety that is covalently bonded to the antibacterial agent, and wherein the delivery agent is either capable of covalently bonding to one or more structures on a bacterial cell membrane or comprises a hydrophilic portion capable of otherwise binding (e.g. by way of electrostatic interactions (i.e. ionic interactions) and/or hydrogen bonding) to one or more structures on a bacterial cell membrane;
(ii) the delivery agent is a compound of formula I,

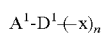   I or a pharmaceutically-acceptable salt thereof, wherein $A^1$ represents a hydrogen atom or a terminating group; $D^1$ represents a dendrimer fragment to which the X groups shown are attached, X represents —$NH_2$, boronic acid or a boronic acid derivative; and n is 2 or more (e.g. from 2 to 20); or
(iii) the delivery agent is a polypeptide, or a pharmaceutically-acceptable salt thereof, that comprises at least two arginine residues and is capable of otherwise binding to one or more structures on a bacterial cell membrane.

For the avoidance of doubt, the delivery agent must be bound or capable of binding to the antibacterial agent, and it must also be bound or capable of binding to one or more structures on a bacterial cell membrane.

By "antibacterial agent" we mean any substance which is capable of inhibiting bacterial growth and/or reproduction, or which is capable of killing bacteria following administration to the organism in vivo or in vitro. This includes known antibiotic compounds, and particularly includes compounds for which the development of bacterial resistance has been observed in the clinic. This also includes fragments of known antibiotic compounds where those fragments are themselves capable of inhibiting bacterial growth and/or reproduction, or capable of killing bacteria, under specific conditions (e.g. once the fragments are brought into association with a target structure in or on a bacterial cell).

By "delivery agent" we mean any substance which facilitates the binding of an antibacterial agent to a portion of a bacterial cell (preferably in the region of the bacterial cell wall), and which can thereby anchor the antibacterial agent in the vicinity of the biological target (e.g. an enzyme that is important for cellular activity).

In particular embodiments of the invention, the delivery agent is covalently bonded to the antibacterial agent. In alternative embodiments, the delivery agent and antibacterial agent are discrete molecules which are capable of binding to each other via non-covalent interactions.

Unless otherwise stated, terms such as "binding", "bound", etc., refer to the interaction between molecules or chemical structures which serve to hold those molecules or chemical structures in close proximity to one another. In the context of the present invention, the term "binding", unless otherwise stated, particularly refers to the binding that occurs as a result of interactions between permanent dipoles or more preferably as a result of hydrogen bonding between the molecular structures involved.

By the term "hydrophilic portion which is capable of binding to one or more structures", we include a molecular fragment which is more soluble in water or other polar solvents (e.g. protic solvents such as alcohols) than in oil or other hydrophobic solvents (e.g. hydrocarbons). The term specifically includes any structure which is capable of binding to one or more structures in bacterial cell membranes by way of one or more hydrogen bonds and/or electrostatic interactions (i.e. ionic bonds).

Delivery Agents

Where the delivery agent is a moiety that is covalently bonded to the antibacterial agent, particular delivery agents that may be mentioned include those which are capable of binding to one or more structures on a bacterial cell membrane via the formation of one or more covalent bonds with said structures, via the formation of one or more hydrogen bonds with said structures, or through electrostatic interactions between oppositely charged regions on the delivery agent and the bacterial cell membrane (i.e. a form of ionic bonding). In particular embodiments, the delivery agents are able to bind to the bacterial cell membrane via one or more such covalent bonds, a plurality of hydrogen bonds and/or a plurality of such electrostatic interactions. For example, the delivery agent moiety may be capable of forming 1, 2, 3, 4, 5, 6, 7, 8, 9 or more separate covalent bonds or hydrogen bonds with said structures, thereby greatly enhancing the extent to which the delivery agent is anchored to the cell wall. Delivery agents which are capable of forming at least 4, at least 6, or at least 8 of such linkages (particularly hydrogen bonding linkages) are preferred.

In embodiments of the invention in which the delivery agent is covalently bonded to the antibacterial agent, as well as embodiments in which the delivery agent and antibacterial agent are not covalently bonded together, covalent bonds between the delivery agent and the one or more structures on the bacterial cell membrane may be formed, for example, where the delivery agent comprises a boronic acid component or a pharmaceutically-acceptable salt thereof. Where such boronic acids or boronic acid derivatives are present, covalent bonding may occur between the boron atoms of the delivery agent and 1,2- and 1,3-diol groups within the saccharides on the surface of the bacterial cell.

In embodiments of the invention in which the delivery agent is covalently bonded to the antibacterial agent, as well as embodiments in which the delivery agent and antibacterial agent are not covalently bonded together, hydrogen bonds between the delivery agent and the one or more structures on the bacterial cell membrane may be formed through interactions of the delivery agent with saccharides on the surface of the bacterial cell, and particularly with other structures such as phosphate groups or sulphate groups in the lipopolysachharides or phospholipids of the cell membrane. Functional groups that are capable of participating in hydrogen bonding are well known to the skilled person. Particular functional groups that may be mentioned in this respect include primary amines amidines (including guanidines) and amides (including ureas), as well as pharmaceutically-acceptable salts thereof. Still further particular functional groups that should be mentioned include primary amines, amidines, guanidines, amides and ureas (and pharmaceutically-acceptable salts thereof).

In embodiments in which the delivery agent binds to the bacterial cell wall by way of one or more electrostatic interactions (optionally in combination with one or more hydrogen bonding interactions), the delivery agent may carry a plurality of positively charged regions. Such positively charged regions are able to interact with the negatively charged phosphate groups that are present in the phospholipids and lipopolysaccharides of the cell membranes. The positively charged regions on the delivery agent may be present due to the delivery agent molecule being provided in the form of a salt, or the delivery agent may exist as a zwitterion under physiological conditions. Accordingly, positive charges may be present as a result of the reaction of a free base form of the delivery agent with an acid to form an acid addition salt. In embodiments of the invention in which the delivery agent is covalently bonded to the antibacterial agent, as well as embodiments in which the delivery agent and antibacterial agent are not covalently bonded together, particular delivery agents that may be mentioned include those which contain a plurality (e.g. at least 4, at least 6, or at least 8 charged regions) of such charged regions.

Particular delivery agents that may be mentioned therefore include those which comprise one or more functional groups selected from the list consisting of boronic acids, boronic acid derivatives, primary amines, guanidines, and pharmaceutically-acceptable acid addition salts thereof. For example, when the delivery agent is covalently bonded to the antibacterial agent, the delivery agent may comprise one or more functional groups selected from the list consisting of boronic acids, boronic acid derivatives, primary amines, guanidines, and pharmaceutically-acceptable acid addition salts thereof, and when the delivery agent is a compound of formula I, X may represent a boronic acid group, a boronic acid derivative, a primary amine, a guanidine, or a pharmaceutically-acceptable acid addition salts of any such groups.

Where the delivery agent comprises one or more primary amine groups, it is preferred that the delivery agent is provided as an acid addition salt (thus containing one or more —$NH_3^+$ groups). Particular delivery agents that may be mentioned in this respect include delivery agents which are not covalently bonded to the antibacterial agent, and which comprise a polypeptide or a polypeptide derivative, or a pharmaceutically-acceptable salt thereof.

In other embodiments of the invention, the delivery agent comprises a plurality of said functional groups, particularly where the functional groups are intended to interact with the cell membrane via electrostatic or hydrogen bonding interactions. For example, the delivery agent may comprise 2, 3, 4, 5, 6, 7, 8, 9 or more of said functional groups. Delivery agents which comprise larger numbers of such functional groups are believed to be capable of binding more strongly to the structures in the bacterial cell wall, and thereby improve the efficacy of the associated antibacterial agent.

In certain embodiments, the delivery agent comprises a dendrimer-like structure. For example, compounds of formula I contain a dendrimer fragment at the position denoted as $D^1$. For the avoidance of doubt, in embodiments of the invention in which the delivery agent is covalently bonded to the antibacterial agent, the delivery agent may also comprise a dendrimer-like structure. The term "dendrimer" is well known in the art, and refers to structures containing a branching, tree-like architecture. Preferably, such dendrimer structures are generally acyclic (e.g. they do not contain any cyclic structures having more than 6 members (i.e. the largest ring structures that may be present in the dendrimers are 6-membered rings such as phenyl groups)) or the dendrimer structure may be completely acyclic. A preferred delivery agent is an organic molecule (or a salt thereof) containing a dendrimer fragment (i.e. a fragment containing multiple, tree-like branches), and each of the branches of that dendrimer fragment may be linked to a relevant functional group. Thus, a single delivery agent may contain a plurality of functional groups capable of binding to a bacterial cell membrane via covalent bonds, hydrogen bonds and/or electrostatic interactions along the lines described above.

Particular delivery agents that may be mentioned include those which contain a dendrimer fragment. For example, delivery agents that may be mentioned include those of formula II:

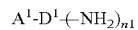

or a pharmaceutically-acceptable salt thereof, wherein A represents a hydrogen atom, a terminating group or an antibacterial agent (or a derivative thereof); $D^1$ represents a dendrimer fragment to which the $NH_2$ groups shown above are attached; and n1 is 2 or more (e.g. from 2 to 20).

Other delivery agents that may be mentioned include those of formulae III and IV:

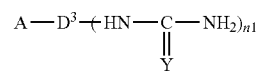

or a pharmaceutically-acceptable salt thereof, wherein each A independently represents a hydrogen atom, a terminating group or an antibacterial agent (or a derivative thereof); $D^2$ and $D^3$ each represent a dendrimer fragment to which the groups shown in parentheses are attached; Y represents O, NH or S; and each n1 is 2 or more (e.g. from 2 to 20).

Further delivery agents that may be mentioned include those of formulae V to VII:

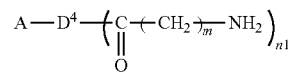
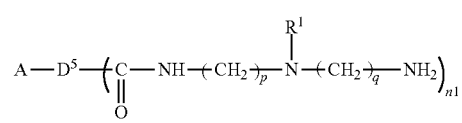
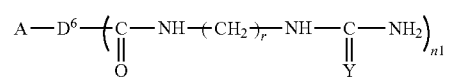

or a pharmaceutically-acceptable salt thereof, wherein each A independently represents a hydrogen atom, a terminating group or an antibacterial agent; each of $D^4$ to $D^6$ represents a dendrimer fragment to which the groups shown in parentheses are attached; Y represents O, NH or S; each n1 is 2 or more (e.g. from 2 to 20); m, p, q and r each independently represent from 1 to 8 (e.g. from 1 to 6); $R^1$ represents a $C_{1-6}$ alkyl group.

In particular embodiments of each of the compounds of formulae I to VII, n1 represents from 3 to 20, from 4 to 18, from 6 to 16 or most particularly from 8 to 16.

Dendrimer fragments $D^1$ to $D^6$ may be polyglycerol-based structures or may be dendron-based structures. Particular dendrimer fragments that $D^1$ to $D^6$ (preferably $D^4$ to $D^6$) may represent include those of formulae A to F:

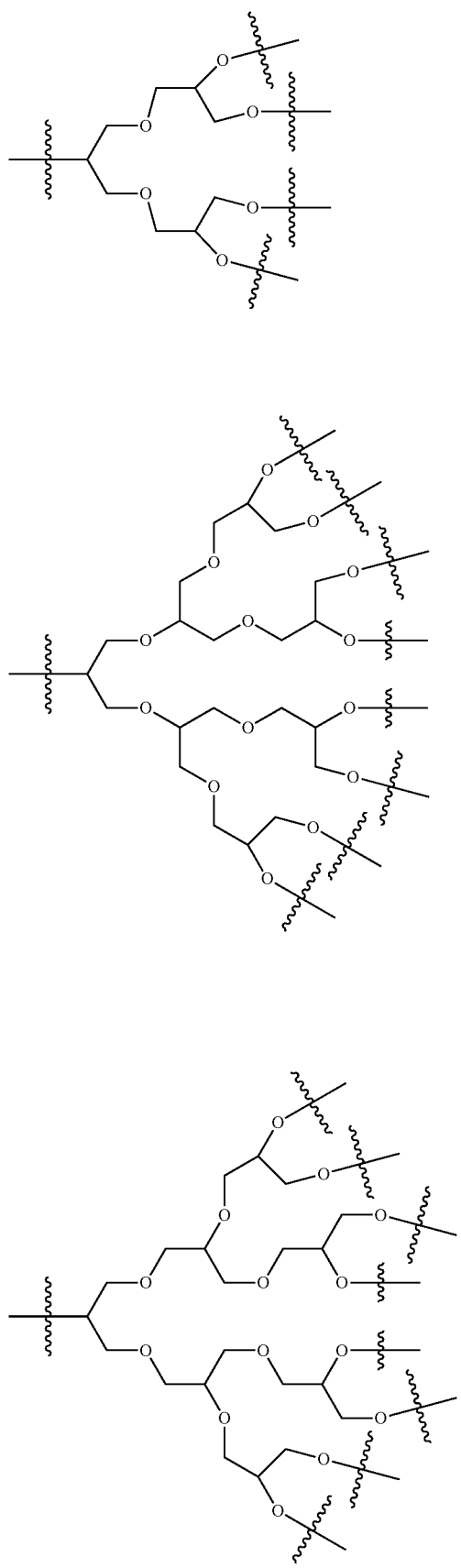
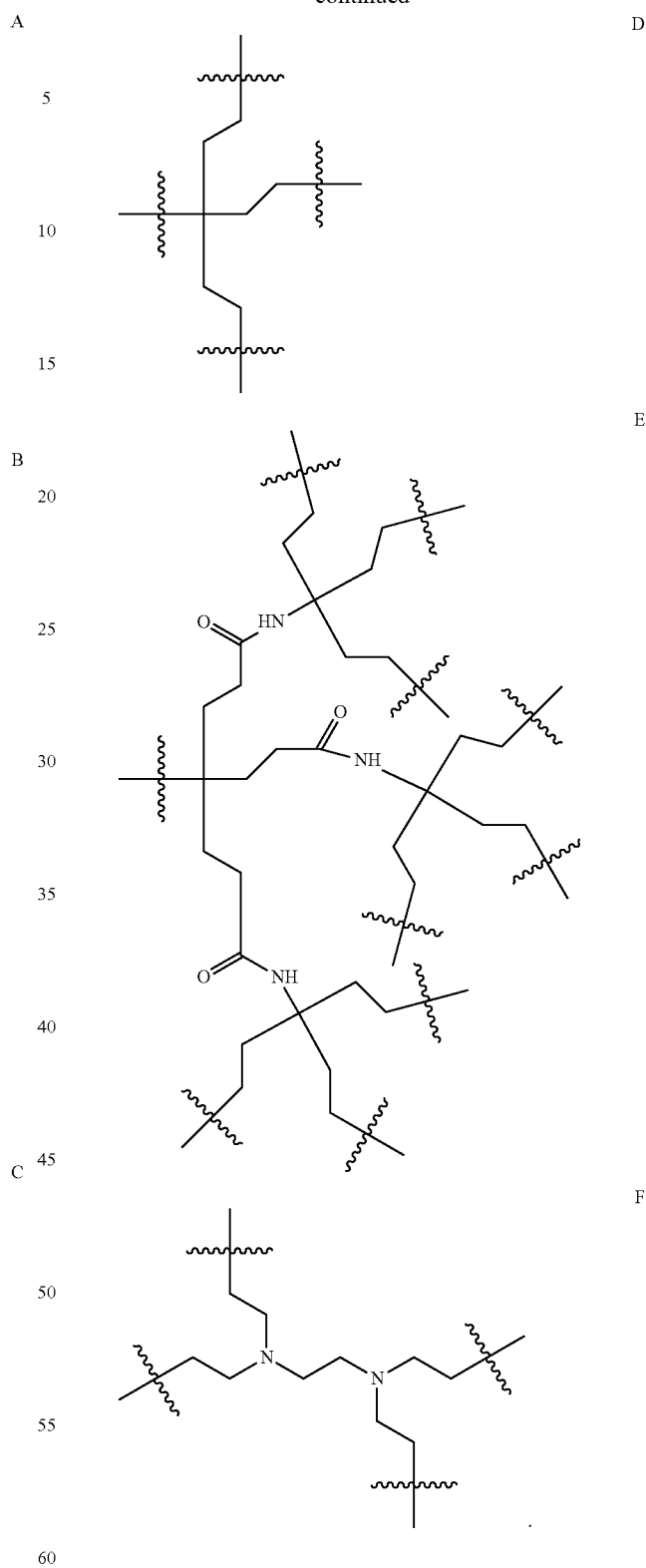
For each of the dendrimers of formula A to E, the single wavy line on the left-hand side of the structures as shown corresponds to the point of attachment of the A, $A^1$ or $A^2$ (which latter group is defined below) group (i.e. the hydrogen atom, the terminating group or the antibacterial agent). The remaining wavy lines indicate the points of attachment of the plurality of amine-, X- or boronic acid-containing portions of the delivery agent (i.e. the bracketed portions in formulae I to IX).

Dendrimer F is an example of a dendrimer that is not covalently bonded to an antibacterial agent, thus all of the wavy lines shown for dendrimer F represent points of attachment of the amine-containing portions of the delivery agent. The group denoted by $A^1$ or A in compounds of formula I to VII is incorporated in the structure for dendrimer F and so is not shown.

In compounds of formulae II to IV, particular dendrimer fragments that $D^1$ to $D^3$ may represent include those of formulae A to F as defined above wherein the dendrimer fragments are linked to the plurality of amine-containing portions of the delivery agent (i.e. the bracketed portions in formulae II to IV) by way of direct bonds or, preferably, additional linker groups. Additional linker groups that may be mentioned in this respect include ester linkages (i.e. —C(O)—O—), amide linkages (i.e. —C(O)—NH—), sulfonamide linkages (i.e. —S(O)$_2$—NH—), ether linkages (i.e. —O—), amine linkages (i.e. —N(R$^x$)— in which R$^x$ represents hydrogen or a $C_{1-6}$ alkyl group), a $C_{1-12}$ (e.g. $C_{1-6}$) alkylene linkage, or a plurality of such linkages in combination. In compounds of formulae II to IV which contain multiple such additional linker groups, the additional linker groups may be the same or different.

Particular preferred delivery agents include:
(i) compounds of formula V in which $D^4$ represents a dendrimer fragment of any one of formulae A to F (particularly formula C);
(ii) compounds of formula VI in which $D^5$ represents a dendrimer fragment of any one of formulae A to F (particularly formulae A or B);
(iii) compounds of formula VII in which $D^6$ represents a dendrimer fragment of any one of formulae A to F (particularly formulae D, E or F).

Other dendrimer structures will be known to the skilled person. For example, various dendrimers that are known to the skilled person include those disclosed in *J. Mater. Chem. B* 2012, 2, 2153-2167. The disclosures in that document show that such dendrimer compounds may have low toxicities.

By the use of the term "terminating group" we include any structural feature that is largely inert under physiological conditions. Particular examples of such groups include hydrogen or a $C_{1-30}$ (e.g. $C_{8-22}$) alkyl chain. Where the terminating group is a $C_{1-30}$ (e.g. $C_{8-22}$) alkyl chain, that group may optionally be interrupted by one or more heteroatoms selected from 0 and N (e.g. so forming an alkyl-O-alkylene-group or an alkyl-N(R$^y$)-alkylene-group in which R$^y$ represents hydrogen or a $C_{1-6}$ alkyl group), and/or it may be bound to the dendrimer portion via an ester linkage, an amide linkage, a sulfonamide linkage, an ether linkage, an aryl group or heteroaryl group. Particular aryl or heteroaryl groups that may be mentioned in this respect include phenyl groups, and 5- or 6-membered heterocyclic aromatic rings in which the ring contains from 1 to 3 heteroatoms selected from O, N and S. For example, the heteroaryl group may be a 1,2,3-triazole, which is advantageous as it is amenable to synthesis via relatively simple chemical processes (known as "click"-chemistry).

Other delivery agents that may be mentioned include those of formulae VIIIa, VIIIb, and IX:

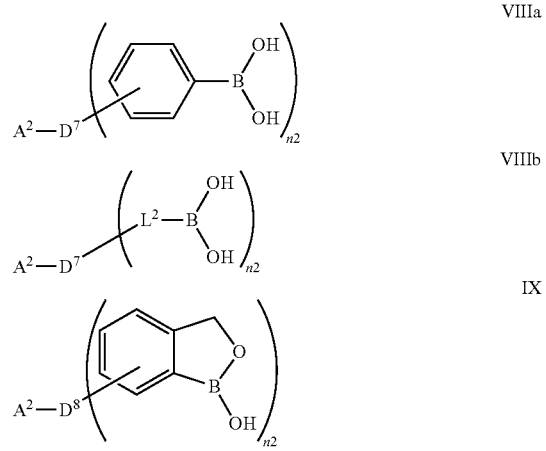

wherein each $A^2$ independently represents an antibacterial agent (or a derivative thereof); $L_2$ represents aliphatic linker (e.g. a $C_{1-6}$ alkyl chain); D7 and $D^8$ independently represent a direct bond or a dendrimer fragment to which the boron-containing groups shown are attached; n2 is 1 or more (e.g. from 2 to 20); and optionally wherein $D^7$ and $D^8$ are attached to the boronic acid portions of the compound of formula VIIIa and IX, or boric acid portions of the compound of formula VIIIb, via a linker group. Thus, where the delivery agent is a compound of formula VIIIa, VIIIb or IX, it is covalently bonded to the antibacterial agent.

In embodiments of compounds of formulae VIIIa, VIIIb and IX, the dendrimer fragments that are represented by $D^7$ and $D^8$ may be polyglycerol-based structures or dendron-based structures as defined above in respect of dendrimer fragments $D^1$ to $D^6$. Similarly, particular dendrimer fragments that $D^7$ and $D^8$ may represent include those of formulae A to E as defined above.

In compounds of formulae VIIIa, VIIIb and IX, the linker group that may be present may comprise one or more groups selected from the list comprising $C_{1-10}$ alkyl, —NH—, —O—, —C(O)—O—, and —C(O)—NH— (wherein the amide and ester linkers may each be attached in either of the two possible orientations). For example, the linker group may be a —(CH$_2$)$_2$—NH—(CH$_2$)$_8$—C(O)—NH— group.

Particular delivery agents that may be mentioned include those which contain a dendrimer fragment. That is, particular delivery agents that may be mentioned include compounds of formulae II, VIIIa, VIIIb and IX, or pharmaceutically-acceptable salts thereof (e.g. compounds of formulae III, IV, VIIIa, VIIIb and IX or pharmaceutically-acceptable salts thereof, or most preferably compounds of formulae V, VI, VII, VIIIa, VIIIb and IX or pharmaceutically-acceptable salts thereof).

Unless otherwise specified, alkyl groups and alkoxy groups as defined herein may be straight-chain or, when there is a sufficient number (i.e. a minimum of three) of carbon atoms, be branched-chain and/or cyclic. Further, when there is a sufficient number (i.e. a minimum of four) of carbon atoms, such alkyl and alkoxy groups may also be part cyclic/acyclic. Such alkyl and alkoxy groups may also be saturated or, when there is a sufficient number (i.e. a minimum of two) of carbon atoms, be unsaturated. Unless otherwise specified, alkyl and alkoxy groups may also be substituted by one or more halo, and especially fluoro, atoms.

Unless otherwise specified, alkylene groups as defined herein may be straight-chain or, when there is a sufficient number (i.e. a minimum of two) of carbon atoms, be branched-chain. Such alkylene chains may also be saturated or, when there is a sufficient number (i.e. a minimum of two) of carbon atoms, be unsaturated. Unless otherwise specified, alkylene groups may also be substituted by one or more halo atoms.

The term "aryl", when used herein, includes $C_{6-10}$ aryl groups such as phenyl, naphthyl and the like. When substituted, aryl groups are preferably substituted by between one and three substituents.

When used herein, the term "heteroaryl group" includes 4- to 12-membered (e.g. 5- to 10-membered) cyclic aromatic groups containing one or more heteroatoms selected from N, O and S. The term therefore includes such groups that are mono- or bicyclic. Preferred heterocyclic groups include groups such as pyrrolyl, furanyl, thienyl, imidazolyl, pyrrazolyl, thiazolyl, oxazolyl, triazolyl (e.g. 1,2,3-triazolyl), benzoxazolyl and pyridyl. Particularly preferred heterocyclic groups include pyrrolyl, imidazolyl, 1,2,3-triazolyl, and oxazolyl.

The term "halo", when used herein, includes fluoro, chloro, bromo and iodo.

Pharmaceutically-acceptable salts that may be mentioned include acid addition salts and base addition salts. Such salts may be formed by conventional means, for example by reaction of a free acid or a free base form of a delivery agent with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a delivery agent in the form of a salt with another counter-ion, for example using a suitable ion exchange resin.

Examples of pharmaceutically acceptable addition salts include those derived from mineral acids, such as hydrochloric, hydrobromic, phosphoric, metaphosphoric, nitric and sulphuric acids; from organic acids, such as tartaric, acetic, trifluoroacetic, citric, malic, lactic, fumaric, benzoic, glycolic, gluconic, succinic and arylsulphonic acids; and from metals such as sodium, magnesium, or preferably, potassium and calcium. Particularly preferred salts include those derived from acetic, trifluoroacetic hydrochloric and tartaric acids.

Certain delivery agents disclosed herein may be novel and so may be of use in the treatments disclosed herein. Thus in a second aspect of the invention, there is provided a delivery agent as defined above. That is, the delivery agent may be a compound of any one of formulae I to IX as defined hereinbefore, or a pharmaceutically-acceptable salt thereof.

In particular embodiments of this aspect of the invention, the delivery agent is not covalently bonded to an antibacterial agent (but may be used in combination with an antibacterial agent in order to achieve the effects described herein).

In a first embodiment in which the delivery agent is not covalently bonded to an antibacterial agent, the delivery agent is a compound of formula I to VII, or a pharmaceutically-acceptable salt thereof, wherein $D^1$ to $D^6$, m, n, p, q, r and $R^1$ are as hereinbefore defined and A, if present, represents $A^1$ as hereinbefore defined.

In a second embodiment in which the delivery agent is not covalently bonded to an antibacterial agent, the delivery agent is a compound of formulae I to VII, or a pharmaceutically-acceptable salt thereof, wherein m, n, p, q, r and $R^1$ are as hereinbefore defined, A represents $A^1$ as hereinbefore defined, and $D^1$ to $D^6$ each represent a dendrimer fragment of formula A to F as hereinbefore defined.

In a third embodiment in which the delivery agent is not covalently bonded to an antibacterial agent, the delivery agent is a compound of formulae V to VII, as hereinbefore defined, wherein m, n, p, q, r and $R^1$ are as hereinbefore defined, A represents $A^1$ as hereinbefore defined, and $D^1$ to $D^6$ each represent a dendrimer fragment of formula A to F as hereinbefore defined (e.g. wherein, in the compounds of formulae VIIIa, VIIIb and IX, the optional linkers between the $D^7/D^8$ groups and the boronic acid or boric acid groups are absent).

In a fourth embodiment in which the delivery agent is not covalently bonded to an antibacterial agent, the delivery agent is a polypeptide or a polypeptide derivative, or a pharmaceutically-acceptable salt thereof. It is preferred (though not essential) that, when the delivery agent is a polypeptide or polypeptide derivative, or a pharmaceutically-acceptable salt thereof, then the polypeptide contains at least two residues selected from the group consisting of arginine and lysine. The amino acid residues may be provided in their naturally occurring stereochemical configuration (e.g. the L-configuration), or the alternative stereochemical configuration. It is preferred that the amino acid residues are provided in their naturally occurring stereochemical configuration.

In embodiments in which the delivery agent is a polypeptide, a polypeptide derivative or a pharmaceutically-acceptable salt thereof (e.g. a polypeptide, or a pharmaceutically-acceptable salt thereof), preferably the polypeptide contains at most 20 (e.g. no more than 15) amino acid residues. Particular polypeptides that may be mentioned include acyclic polypeptides (e.g. acyclic polypeptides containing at most 20 amino acid residues). For example, polypeptides of particular interest include those which contain at least four, at least six or at least eight arginine residues. In all cases, the term the amino acids that form the polypeptides that may be used in the delivery agents may be in either the D or L forms.

Other polypeptides and polypeptide derivatives of particular interest include compounds containing a sequence of at most 20 (e.g. between 5 and 15) amino acid residues. Polypeptide derivatives include polypeptide compounds which contain non-peptide moieties at one or both ends of the peptide chain. Alternatively or additionally, polypeptide derivatives include polypeptide compounds in which one or more of the amino acids is optionally provided in a chemically modified form. Examples of such modifications include replacing one or more —$NH_2$ groups on side chains on said amino acids (e.g. the side chains of lysine or arginine) with amides and derivatives thereof (e.g. amides, ureas, thioamides or thioureas).

Particular polypeptides and polypeptide derivatives that may be mentioned in this respect include compounds containing a polypeptide sequence selected from the list consisting of formulae XX to XL:

| | |
|---|---|
| RRRRRRRR (SEQ ID NO: 1) | XX |
| KPLIYLLRLRGQF (SEQ ID NO: 2) | XXI |
| KPLIYLLLRRGQF (SEQ ID NO: 3) | XXII |
| KRRKRRKRR (SEQ ID NO: 4) | XXIII |
| KRRRRRR (SEQ ID NO: 5) | XXIV |
| PLIYLKLLKGQF (SEQ ID NO: 6) | XXV |
| rrrrrrr (SEQ ID NO: 7) | XXVI |

| | |
|---|---|
| PLIYLLGRR (SEQ ID NO: 8) | XXVII |
| PLIYLLRGR (SEQ ID NO: 9) | XXVIII |
| PLIYLLKGR (SEQ ID NO: 10) | XXIX |
| PLIYLLRGK (SEQ ID NO: 11) | XXX |
| PLIYLLKGK (SEQ ID NO: 12) | XXXI |
| PLIYLKLLK (SEQ ID NO: 13) | XXXII |
| KKKKKR (SEQ ID NO: 14) | XXXIII |
| RRRR (SEQ ID NO: 15) | XXXIV |
| RRRRRRRR (SEQ ID NO: 16) | XXXV |
| RRRRRRRRR (SEQ ID NO: 17) | XXXVI |
| KKRRRRRRR (SEQ ID NO: 18) | XXXVII |
| KKRKKKKR (SEQ ID NO: 19) | XXXVIII |
| RRWWRRWRR (SEQ ID NO: 21) | XXXIX |
| PLIYLRLLRGQF (SEQ ID NO: 22) | XL |

In a further embodiment, the polypeptide derivative may consist of one amino acid selected from the group consisting of arginine and lysine.

In each case, either the N-terminus or the C-terminus, or both, may be modified, e.g. one or both ends of the polypeptide may be modified with a PEG group, an azide, an alkyne group, an alkyl group, an —OH group, a —C(O)—NH$_2$ group or a thiol. For example, the —C(O)OH at the C-terminus may be replaced with a —C(O)—C≡CH group. As a further example, the N-terminus may be modified by the incorporation of a dye label (e.g. a TAMRA dye label) or a —C(O)—NH$_2$ group.

Polypeptides and polypeptide derivatives which contain higher positive charge have been found to have increased effectiveness in enhancing the antibacterial potential (i.e. reducing the minimum inhibitory concentration) of existing antibacterial agents when the two agents are provided in combination. Therefore, in a preferred embodiment, the polypeptide or polypeptide derivative is a polypeptide-containing compound that bears a positive charge of at least 3 units. Particularly preferred embodiments include those in which the polypeptide or polypeptide derivative is a polypeptide-containing compound that bears a positive charge of at least 5 (e.g. at least 6) units.

The positive charge may be nominally determined by counting the number of lysine and arginine amino acids that are present in the polypeptide (each such amino acid providing one unit of positive charge). Other amino acids having side chains that are positively charged may also be mentioned in this respect.

Other polypeptides that may be used in the present invention include disulphide-based polypeptides. Examples of such polypeptides include poly-CBA peptides (e.g. as disclosed in Son et al. *Accounts of Chemical Research*, (2012) Vol 45, No. 7, 1100-1112 (see, in particular, poly (CBA-DAH) modified with arginine residues (poly(CBA-DAH-R), and poly(CBA-DAH) containing RGD peptide)).

Polypeptide delivery agents may be bound to the antibacterial agent, or alternatively may be provided as a separate agent. Salts (e.g. acid addition salts) of such polypeptide-based delivery agents are of particular interest.

Examples of polypeptide-based delivery agents which may be (covalently) bound to an antibacterial agent include delivery agents containing a polypeptide sequence selected from the list consisting of formulae XX to XXXII, as defined above. Particular such delivery agents include those containing a polypeptide sequence selected from the list consisting of formulae XX, XXIII and XXXIII. The polypeptide-based delivery agent may be bound to the antibacterial agent by any one of the structural linkages discussed hereinafter.

Without wishing to be bound by theory, it is believed that the delivery agents disclosed herein are able to facilitate the binding of an antibacterial agent close to the cell membrane in a bacterial cell due to the presence of functional groups on the delivery agent which are capable of hydrogen bonding to the cell wall, or bonding through electrostatic interactions. The delivery agent may be able to mask certain negative charges that may exist on the antibacterial fragment. For example, moenomycin derivatives contain a phosphate group and a carboxylate group, either of which may dissociate into anionic species under physiological conditions. The presence of similar charges on phosphate groups that are present in bacterial cell wall phospholipids and lipopolysaccharides (particularly in Gram negative bacteria) may prevent the antibacterial from entering the cell or approaching the target region.

It is also believed that the delivery agents disclosed herein are capable of reducing the extent to which certain antibacterials bind to blood plasma, thereby increasing the bioavailability of those antibacterials.

Antibacterial Agents

Antibacterial Agents that are of use in the context of the present invention are chemical agents that are bactericidal or bacteriostatic. These include known and naturally occurring antibacterial agents (include synthetic and semi-synthetic antibacterial agents), as well as fragments of those agents where those fragments retain at least a portion of the bactericidal or bacteriostatic activity.

Particular antibacterial agents that may be mentioned include those in which the agent is a molecule or fragment that inhibits the synthesis or repair of bacterial cell walls.

Other particular antibacterial agents that may be mentioned include those in which the agent is a molecule or fragment that modulates the activity of a penicillin binding protein. More particular antibacterial agents include those in which the agent is a molecule or fragment that inhibits a glycosyltransferase enzyme in a bacterium (e.g. a glycosyltransferase enzyme in a penicillin binding protein). In this context, compounds that inhibit a glycosyltransferase enzyme are capable of reducing the formation of peptidoglycan bonds in a bacterial cell, particularly reducing the formation of peptidoglycan bonds that are formed during bacterial cell wall synthesis.

Other antibacterial agents that may be mentioned include those which comprise a glycopeptide or a phosphoglycolipid fragment.

Most particular antibacterial agents that may be mentioned include moenomycin (including moenomycin A), vancomycin, β-lactam antibiotics, and derivatives thereof. The structure of moenomycin A is shown in FIG. 1.

In some embodiments of the invention, the antibacterial agent is covalently bonded to the delivery agent.

Where the antibacterial agent is moenomycin, or a derivative thereof, the delivery agent may be bonded to the moenomycin at any position on the molecular skeleton. For example, the moenomycin, or derivative thereof, may be bound to the delivery agent:

(i) such that the delivery agent (and any associated linker) replaces part or all of the 2-amido-cyclopentane-1,3-dione portion of the moenomycin;

or particularly, (ii) via the moenocinol portion of the moenomycin;

(iii) such that the delivery agent (and any associated linker) replaces part or all of the moenocinol portion of the moenomycin; or (iv) via the 2-amino-cyclopentane-1,3-dione portion of the moenomycin.

Particular delivery agents that may be mentioned in this respect include delivery agents of formulae II to IX, or pharmaceutically-acceptable salts thereof, wherein $D^1$ to $D^8$, m, n, p, q, r and $R^1$ are as hereinbefore defined and A and $A^2$ each represent moenomycin or a derivative thereof.

Further delivery agents that may be mentioned in this respect include delivery agents of formulae II to IX, or pharmaceutically-acceptable salts thereof, wherein m, n, p, q, r and $R^1$ are as hereinbefore defined, A and $A^2$ each represents moenomycin or a derivative thereof, and $D^1$ to $D^8$ each represent a dendrimer fragment of formula A to E as hereinbefore defined.

Still further delivery agents that may be mentioned in this respect include delivery agents of formulae V to IX, or pharmaceutically-acceptable salts thereof, wherein m, n, p, q, r and $R^1$ are as hereinbefore defined, A and $A^2$ each represents moenomycin or a derivative thereof, and $D^1$ to $D^8$ each represent a dendrimer fragment of formula A to E as hereinbefore defined (e.g. wherein, in the compounds of formulae VIIIa, VIIIb and IX, the optional linkers between the $D^7/D^8$ groups and the boric acid or boronic acid groups are absent).

Still further delivery agents that may be mentioned in this respect include delivery agents which contain a polypeptide sequence as defined above bound to the antibacterial agent.

In one embodiment, the delivery agent is an agent which contains a polypeptide sequence selected from the list consisting of formulae XX to XXXII as defined above (and, in particular, a polypeptide sequence selected from the list consisting of formulae XX, XXIII and XXXIII).

Polypeptide-based delivery agents may be bound to the antibacterial agent either directly or via a linker group. Suitable linker groups include any structural fragments that would be known to the skilled person. Such linker groups may include one or more fragments selected from the list comprising an optionally substituted alkyl chain, a carbonyl group, an amide group, an amine group, an ether group, and an optionally substituted aromatic (e.g. a phenyl or heteroaromatic ring).

Particular linkers that may be mentioned include linkers selected from formulae $L_A$ and $L_B$:

wherein the wavy line on the left-hand side represents the point of attachment of the linker to the antibacterial agent, and the wavy line on the right-hand side represents the point of attachment of the linker to the polypeptide-based delivery agent (typically at the C-terminal end), and wherein X represents —O—, a $C_{1-12}$ alkyl group or a polyethylene glycol group (e.g. a group containing —$(CH_2CH_2O)_n$— wherein n is from 1 to 10 (such as from 2 to 5)).

When such linkers are used to join a polypeptide-based delivery agent to moenomycin, it is preferred that the triazole ring is bound to the moenomycin in place of the 2-amido-cyclopentane-1,3-dione constituent of moenomycin.

Covalent conjugates of moenomycin with in combination with particular polypeptide-based delivery agents and linkers have been found to exhibit an increased synergistic effect when used to combat particular pathogens. For example, an antibacterial agent containing moenomycin bound to a polypeptide sequence of formula XX via a linker of formula $L_A$ or $L_B$ (preferably $L_B$) in which X represents a $C_{1-6}$ alkyl-C(O)—NH—$C_{1-6}$ alkyl chain is particularly effective when used to treat *P. aeruginosa* or *K. pneumoniae*.

An antibacterial agent containing moenomycin bound to a polypeptide sequence of formula XXXIII via a linker of formula $L_B$ in which X represents a —$(CH_2CH_2O)_2$—$(CH_2)_2$—NH—C(O)—$(CH_2)_2$—C(O)— group is particularly effective when used to treat *P. aeruginosa* or *A. baumannii*.

An antibacterial agent containing moenomycin bound to a polypeptide sequence of formula XXIII via a linker of formula $L_B$ in which X represents a $C_5$ alkyl chain is particularly effective when used to treat *K. pneumoniae* or *A. baumannii*.

Antibacterial agents containing moenomycin bound to a polypeptide sequence of formula XXXIII via a linker of formula $L_B$ in which X represents a direct bond, —O— or a $C_5$ alkyl chain is also particularly effective when used to treat *A. baumannii*.

The antibacterial agents and delivery agents may exhibit tautomerism. All tautomeric forms and mixtures thereof are included within the scope of the invention.

The antibacterial agents and delivery agents may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional (e.g. fractional crystallisation or HPLC) techniques. Alternatively the desired optical isomers may be made by reaction of the appropriate optically active starting materials under conditions which will not cause racemisation or epimerisation, or by derivatisation, for example with a homochiral acid followed by separation of the diastereomeric esters by conventional means (e.g. HPLC, chromatography over silica). All stereoisomers are included within the scope of the invention.

Particular embodiments of the invention that may be mentioned include the compounds of the Examples disclosed hereinafter.

Preparation

Delivery agents (including compounds of formulae I to IX) may be prepared in accordance with techniques known to those skilled in the art, for example as described hereinafter.

Thus, according to a third aspect of the invention there is provided a process for the preparation of a compound of formula I (or a compound of formula II, III, IV, V, VI, VII, VIIIa, VIIIb or IX, as appropriate), which comprises:

(a) for compounds of formula I in which X represents —$NH_2$ and $A^1$, $D^1$ and n are as hereinbefore defined, or for compounds of formula II as hereinbefore defined, reaction of a compound of formula X:

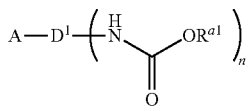

X wherein A, $D^1$ and n are as defined hereinbefore and $R^{a1}$ represents a $C_{1-12}$ alkyl group, with an acid (such as hydrochloric acid, trifluoroacetic acid or p-toluenesulfoic acid), for example under conditions known to those skilled in the art (such as in the presence of a suitable organic solvent (e.g. dioxane, THF, MeCN, diethyl ether, EtOAc, DCM or DMF));

(b) for compounds of formula IV wherein Y represents NH, reaction of a compound of formula I wherein X represents —$NH_2$, and $A^1$, $D^1$ and n are as hereinbefore defined, or a compound of formula II as hereinbefore defined, with a compound of formula XI,

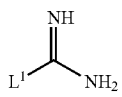

XI wherein $L^1$ represents a suitable leaving group (such as an aryl group or a heteroaryl group (e.g. a pyrazole group)) under conditions known to those skilled in the art (such as in the presence of a suitable organic solvent (e.g. methanol, ethanol, MeCN, THF) and, optionally, in the presence of a suitable base (e.g. $Et_3N$, pyridine, DMAP or DIPEA);

(c) for compounds of formula VII, reaction of a compound of formula XII,

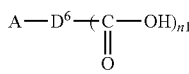

XII wherein A, $D^6$ and n1 are as defined hereinbefore, by an amide coupling reaction, i.e. the formation of an amide from a carboxylic acid, with a compound of formula XIII,

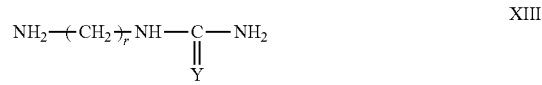

XIII wherein r and Y are as defined hereinbefore, which reaction may be performed in the presence of a suitable coupling reagent (e.g. 1,1'-carbonyldiimidazole, N,N'-dicyclohexylcarbodiimide, N,N'-diisopropylcarbodiimide, 1-hydroxy-7-azabenzotriazole (HOAt), or the like) or, alternatively the —C(O)OH group may first be activated to the corresponding acyl halide (e.g —C(O)Cl, by treatment with oxalyl chloride, thionyl chloride, phosphorous pentachloride, phosphorous oxychloride, or the like) under standard conditions known to those skilled in the art (e.g. optionally in the presence of a suitable solvent, suitable base and/or in an inert atmosphere);

(d) for compounds of formula VII, reaction of a compound of formula XII in which the carboxylic acid group(s) is(are) provided as an ester derivative, with a compound of formula XIII, in the presence of, e.g. trimethylaluminium, for example in an inert atmosphere and in the presence of a suitable solvent (e.g. dichloromethane); or (e) for compounds of formula III, in which the amidine (—C(=NH)—$NH_2$) group is linked to $D^2$ via a linker comprising a —$CH_2$—NH— group, reaction of a compound of formula XIV,

XIV wherein A, $D^2$ and n1 are as defined hereinbefore, by reductive amination using a compound of formula XV,

XV wherein Q represents an appropriate linker group (such as a linker containing one or more groups selected from $C_{1-6}$ alkylene, —NH—, —C(O)—NH—, —C(O)—O— and —O—), under appropriate reaction conditions, for example in a "one-pot" procedure in the presence of an appropriate reducing agent, such as a chemoselective reducing agent such as sodium cyanoborohydride or, preferably, sodium triacetoxyborohydride, or the like. Alternatively, such reactions may be performed in two steps, for example a condensation step (in the presence of e.g. a dehydrating agent such as trimethyl orthoformate or $MgSO_4$ or molecular sieves, etc) followed by a reduction step (e.g. by reaction in the presence of a reducing agent such as a chemoselective one mentioned above or $NaBH_4$, $AlH_4$, or the like), for instance the conversion of —$NH_2$ to —N(H)-isopropyl by condensation in the presence of acetone ($H_3C$—C (O)—CH$_3$) followed by reduction in the presence of a reducing agent such as sodium cyanoborohydride (i.e. overall a reductive amination).

Compounds of formulae III, V and VI may be prepared by processes analogous to process (a) above for compounds of formulae I or II, using appropriate starting materials (i.e. appropriate compounds of formula X in which the D$^1$ group contains the relevant linker groups that are attached to the requisite —NH$_2$ groups).

Compounds of formulae VIIIa, VIIIb and IX may be made, for example, by processes analogous to processes (c) to (e) above, e.g. via amide formation reactions or reductive amination processes. An example of a process analogous to process (e) above includes the reaction of a compound of formula XVI,

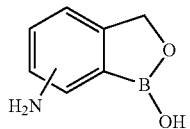

XVI with a compound of formula XVII,

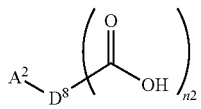

XVII wherein A$^2$, D$^8$ and n2 are as hereinbefore defined under reductive amination conditions, for example as described above.

Other specific transformation steps (including those that may be employed in order to form compounds of formulae I to IX) that may be mentioned include:

(i) reductions, for example of a carboxylic acid (or ester) to either an aldehyde or an alcohol, using appropriate reducing conditions (e.g. —C(O)OH (or an ester thereof), may be converted to a —C(O)H or —CH$_2$—OH group, using DIBAL and LiAlH$_4$, respectively (or similar chemoselective reducing agents));

(ii) reductions of an aldehyde (—C(O)H) group to an alcohol group (—CH$_2$OH), using appropriate reduction conditions such as those mentioned in point (i) above; (iii) oxidations, for example of a moiety containing an alcohol group (e.g. —CH$_2$OH) to an aldehyde (e.g. —C(O)H) or of a —S— moiety to a —S(O)— or —S(O)$_2$— moiety (or the reverse reduction reaction), for example in the presence of a suitable oxidising agent, e.g. MnO$_2$ or mcpba or the like;

(iv) conversion of a primary amide to a nitrile functional group, for example under dehydration reaction conditions, e.g. in the presence of POCl$_3$, or the like;

(v) nucleophilic substitution (e.g. aromatic nucleophilic substitution) reactions, where any nucleophile replaces a leaving group, e.g. an amine may replace a —S(O)CH$_3$ leaving group;

(vi) transformation of a methoxy group to a hydroxy group, by reaction in the presence of an appropriate reagent, such as boron fluoride-dimethyl sulfide complex or BBr$_3$ (e.g. in the presence of a suitable solvent such as dichloromethane);

(vii) alkylation, acylation or sulfonylation reactions, which may be performed in the presence of base and solvent (such as those described hereinbefore);

(viii) specific deprotection steps, such as deprotection of a hydroxy group protected as a silyl ether (e.g. a tert-butyldimethylsilyl protecting group) by reaction with a source of fluoride ions, e.g. by employing the reagent tetrabutylammonium fluoride (TBAF).

Compounds of formulae X, XII, XIV and XVII can be prepared by methods analogous to those described above together with other reactions that are known to those skilled in the art.

Compounds of formulae I to XVII which contain dendrimer structures may be made according to methods known in the art, for example according to the methods described in *J. Mater. Chem.* B 2012, 2, 2153-2167.

Salts of compounds of formulae I to IX (and salts of other compounds) may be formed by conventional means, for example by reaction of a free acid or a free base form of a corresponding compound of formula I to IX with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

Compounds of formula I (etc.) may be isolated from their reaction mixtures using conventional techniques. For example, compounds of formula I (etc.) may be isolated by conversion to an acid (e.g. hydrochloric acid) salt (e.g. by way of addition of acid to the crude product) and then recrystallisation of the salt from a suitable solvent (e.g. methanol or, particularly, ethanol). Alternatively, the salt can simply be washed with or slurried in the presence of such a suitable solvent in order to isolate the pure acid salt of the compound of formula I.

It will be appreciated by those skilled in the art that in the processes described above and hereinafter the functional groups of intermediate compounds may need to be protected by protecting groups.

Functional groups that it is desirable to protect include hydroxy, amino and carboxylic acid groups. Suitable protecting groups for hydroxy include optionally substituted and/or unsaturated alkyl groups (e.g. methyl, allyl, benzyl or tert-butyl), trialkylsilyl or diarylalkylsilyl groups (e.g. t-butyldimethylsilyl, t-butyldiphenylsilyl or trimethylsilyl) and tetrahydropyranyl. Suitable protecting groups for carboxylic acids include C$_{1-6}$ alkyl or benzyl esters.

The protection and deprotection of functional groups may take place before or after coupling, or before or after any other reaction in the above-mentioned schemes.

Protecting groups may be removed in accordance with techniques that are well known to those skilled in the art and as described hereinafter.

Persons skilled in the art will appreciate that, in order to obtain compounds of formula I (etc.) in an alternative, and, on some occasions, more convenient, manner, the individual process steps mentioned hereinbefore may be performed in a different order, and/or the individual reactions may be performed at a different stage in the overall route (i.e. substituents may be added to and/or chemical transformations performed upon, different intermediates to those mentioned hereinbefore in conjunction with a particular reaction). This may negate, or render necessary, the need for protecting groups.

The type of chemistry involved will dictate the need, and type, of protecting groups as well as the sequence for accomplishing the synthesis.

The use of protecting groups is fully described in "Protective Groups in Organic Chemistry", edited by J W F McOmie, Plenum Press (1973), and "Protective Groups in Organic Synthesis", $3^{rd}$ edition, T. W. Greene & P. G. M. Wutz, Wiley-Interscience (1999).

Protected derivatives of compounds of formula I (etc.) may be converted chemically to compounds of the invention using standard deprotection techniques (e.g. hydrogenation). The skilled person will also appreciate that certain compounds of formula I (etc.) may also be referred to as being "protected derivatives" of other compounds of formula I.

Those skilled in the art will also appreciate that certain compounds of formula I (etc.) will be useful as intermediates in the synthesis of certain other compounds of formula I.

Antibacterial agents may be commercially available, or may be synthesised according to known procedures. In many cases, antibacterial agents may be available from biological sources.

For example, moenomycin is produced by at least four streptomycete strains, *Streptomyces ghanaensis* (ATCC14672), *S. bambergiensis* (ATCC13879), *S. ederensis* (ATCC15304) and *S. geysiriensis* (ATCC15303). The composition of the flavomycin complex produced by *S. ghanaensis* has been thoroughly studied. As a result, a number of phosphoglycolipids have been isolated and structures of moenomycins A, $A_{12}$, $C_1$, $C_3$ and $C_4$ have been determined. (Ostash B. et al. *Nat. Prod. Rep.*, 2010, 27, 1594-1617). Moenomycin may be obtained by the processes disclosed in M. Adachi et al., *J. Am. Chem. Soc.* 2006, 128, 14012-14013.

Moenomycin may alternatively be synthesised by bench chemistry (J. G. Taylor, et al., *J. Am. Chem. Soc.*, 2006, 128, 15084; J. G. Taylor, Ph.D. Thesis, Harvard University, 2006; and P. Welzel, *Angew. Chem., Int. Ed.*, 2007, 46, 4825).

Antibacterial agents (whether naturally occurring or not) may be derivatised by way of chemical methods that are known to the skilled person.

For example, the cyclopentyl ring in moenomycin may be derivatised or replaced according to the procedures discussed in Ostash B. et al. ibid., and references cited therein. In particular, the antibacterial may be treated with an aryl diazonium salt, via a Japp-Klingemann reaction, to produce various substituted triazole moieties.

The lipid moiety in moenomycin (which moiety is known as moenocinol) may also be modified, removed or replaced according to methods known to the skilled person (e.g. those described in Ostash B. et al. ibid., and references cited therein). For example, moenomycin (optionally in a protected form) may be ozonised to give an aldehyde of formula XVIII,

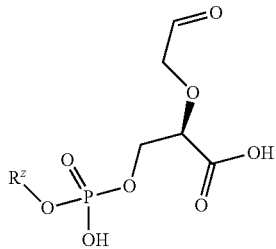

XVIII wherein $R^z$ represents the carbohydrate portion of the molecule (or a derivative thereof), thereby removing the majority of the lipid portion of the molecule.

The compound of formula XVIII may then be further modified, for example by reductive amination of the newly formed aldehyde moiety (e.g. along the lines of reaction (e) above), to give the antibacterial agents that are useful in the compositions of the invention.

Uses and Pharmaceutical Preparations

Compositions of the invention are useful because they possess pharmacological activity. They are therefore indicated as pharmaceuticals.

Thus, according to a fourth aspect of the invention there is provided the compositions of the invention for use as pharmaceuticals.

In particular, compositions of the invention may bind to certain enzymes located in the cell walls of bacteria, thereby inhibiting the activity of those enzymes. Enzymes that may be mentioned in this respect include those necessary for synthesis and repair of bacterial cell walls (e.g. penicillin binding proteins), thus providing the effect of inhibiting bacterial growth, survival and reproduction. Particular enzymes of note are those involved in bond formation in peptidoglycan (a polymer component of bacterial cell walls).

In this respect, fifth, sixth, seventh and eighth aspects of the invention provide, respectively:

(a) the use of a composition of the invention, as hereinbefore defined, for the preparation of a medicament for the treatment or prevention of a bacterial infection;

(b) a method of treating or preventing a bacterial infection in a subject, the method comprising administering to said subject an antibacterially effective amount of a composition of the invention, as hereinbefore defined;

(c) a composition of the invention, as hereinbefore defined, for use in treating or preventing a bacterial infection;

(d) use (e.g. ex vivo use) of a composition of the invention to kill bacteria.

When used herein, the terms "bacteria" (and derivatives thereof, such as "bacterial infection") includes references to organisms (or infections due to organisms) of the following classes and specific types:

Gram-positive cocci, such as

Staphylococci (e.g. *Staph. aureus, Staph. epidermidis, Staph. saprophyticus, Staph. auricularis, Staph. capitis capitis, Staph. c. ureolyticus, Staph. caprae, Staph. cohnii cohnii, Staph. c. urealyticus, Staph. equorum, Staph. gallinarum, Staph. haemolyticus, Staph. hominis hominis, Staph. h. novobiosepticius, Staph. hyicus, Staph. intermedius, Staph. lugdunensis, Staph. pasteuri, Staph. saccharolyticus, Staph. schleiferi schleiferi, Staph. s. coagulans, Staph. sciuri, Staph. simulans, Staph. warneri* and *Staph. xylosus*) and Streptococci (e.g.

beta-haemolytic, pyogenic streptococci (such as *Strept. agalactiae, Strept. canis, Strept dysgalactiae dysgalactiae, Strept dysgalactiae equisimilis, Strept equi equi, Strept equi zooepidemicus, Strept. iniae, Strept porcinus* and *Strept. pyogenes*), microaerophilic, pyogenic streptococci (*Streptococcus* "milleri", such as *Strept. anginosus, Strept constellatus constellatus, Strept constellatus pharyngidis* and *Strept intermedius*), oral streptococci of the "*mitis*" (alpha-haemolytic—
*Streptococcus* "*viridans*", such as *Strept. mitis*,
*Strept. oralis*, *Strept. sanguinis*, *Strept. cristatus*,
*Strept gordonii* and *Strept. parasanguinis*), "*salivarius*" (non-haemolytic, such as *Strept. salivarius* and *Strept vestibularis*) and "*mutans*"
(tooth-surface streptococci, such as *Strept. criceti*,
*Strept. mutans*, *Strept. ratti* and *Strept. sobrinus*)
groups,

*Strept. acidominimus*, *Strept. bovis*, *Strept. faecalis*,
*Strept. equinus*, *Strept. pneumoniae* and *Strept. suis*, or Streptococci alternatively classified as Group A, B, C, D, E, G, L, P, U or V *Streptococcus*);

Gram-negative cocci, such as *Neisseria gonorrhoeae*, *Neisseria meningitidis*, *Neisseria cinerea*, *Neisseria elongata*, *Neisseria flavescens*, *Neisseria lactamica*, *Neisseria mucosa*, *Neisseria sicca*, *Neisseria subflava* and *Neisseria weaveri*;

Bacillaceae, such as *Bacillus anthracis*, *Bacillus subtilis*, *Bacillus thuringiensis*, *Bacillus stearothermophilus* and *Bacillus cereus*;

Enterobacteriaceae, such as
*Escherichia coli*,
*Enterobacter* (e.g. *Enterobacter aerogenes*, *Enterobacter agglomerans* and *Enterobacter cloacae*)
*Citrobacter* (such as *Citrob. freundii* and *Citrob. divernis*),
*Hafnia* (e.g. *Hafnia alvei*),
*Erwinia* (e.g. *Erwinia persicinus*),
*Morganella morganii*,
*Salmonella* (*Salmonella enterica* and *Salmonella typhi*),
*Shigella* (e.g. *Shigella dysenteriae*, *Shigella flexneri*, *Shigella boydii* and *Shigella sonnei*),
*Klebsiella* (e.g. *Klebs. pneumoniae*, *Klebs. oxytoca*, *Klebs. ornitholytica*, *Klebs. planticola*, *Klebs. ozaenae*, *Klebs. terrigena*, *Klebs. granulomatis* (*Calymmatobacterium granulomatis*) and *Klebs. rhinoscleromatis*),
*Proteus* (e.g. *Pr. mirabilis*, *Pr. rettgeri* and *Pr. vulgaris*),
*Providencia* (e.g. *Providencia alcalifaciens*, *Providencia rettgeri* and *Providencia stuartii*),
*Serratia* (e.g. *Serratia marcescens* and *Serratia liquifaciens*), and
*Yersinia* (e.g. *Yersinia enterocolitica*, *Yersinia pestis* and *Yersinia pseudotuberculosis*);

Enterococci (e.g. *Enterococcus avium*, *Enterococcus casseliflavus*, *Enterococcus cecorum*, *Enterococcus dispar*, *Enterococcus durans*, *Enterococcus faecalis*, *Enterococcus faecium*, *Enterococcus flavescens*, *Enterococcus gallinarum*, *Enterococcus hirae*, *Enterococcus malodoratus*, *Enterococcus mundtii*, *Enterococcus pseudoavium*, *Enterococcus raffinosus* and *Enterococcus solitarius*);

*Helicobacter* (e.g. *Helicobacter pylori*, *Helicobacter cinaedi* and *Helicobacter fennelliae*);

*Acinetobacter* (e.g. *A. baumanfi*, *A. calcoaceticus*, *A. haemolyticus*, *A. johnsonii*, *A. junii*, *A. lwoffi* and *A. radioresistens*);

*Pseudomonas* (e.g. *Ps. aeruginosa*, *Ps. maltophilia* (*Stenotrophomonas maltophilia*), *Ps. alcaligenes*, *Ps. chlororaphis*, *Ps. fluorescens*, *Ps. luteola*. *Ps. mendocina*, *Ps. monteilii*, *Ps. oryzihabitans*, *Ps. pertocinogena*, *Ps. pseudalcaligenes*, *Ps. putida* and *Ps. stutzeri*);

*Bacteroides fragilis*;
*Peptococcus* (e.g. *Peptococcus niger*);
*Peptostreptococcus*;
*Clostridium* (e.g. *C. perfringens*, *C. difficile*, *C. botulinum*, *C. tetani*, *C. absonum*, *C. argentinense*, *C. baratii*, *C. bifermentans*, *C. beijerinckii*, *C. butyricum*, *C. cadaveris*, *C. camis*, *C. celatum*, *C. clostridioforme*, *C. cochlearium*, *C. cocleatum*, *C. fallax*, *C. ghonii*, *C. glycolicum*, *C. haemolyticum*, *C. hastiforme*, *C. histolyticum*, *C. indolis*, *C. innocuum*, *C. irregulare*, *C. leptum*, *C.* limosum, *C. malenominatum*, *C. novyi*, *C. oroticum*, *C. paraputrificum*, *C. piliforme*, *C. putrefasciens*, *C. ramosum*, *C. septicum*, *C. sordelii*, *C. sphenoides*, *C. sporogenes*, *C. subterminale*, *C. symbiosum* and *C. tertium*);

*Mycoplasma* (e.g. *M. pneumoniae*, *M. hominis*, *M. genitalium* and *M. urealyticum*);

Mycobacteria (e.g. *Mycobacterium tuberculosis*, *Mycobacterium avium*, *Mycobacterium fortuitum*, *Mycobacterium marinum*, *Mycobacterium kansasii*, *Mycobacterium chelonae*, *Mycobacterium abscessus*, *Mycobacterium leprae*, *Mycobacterium smegmitis*, *Mycobacterium africanum*, *Mycobacterium alvei*, *Mycobacterium asiaticum*, *Mycobacterium aurum*, *Mycobacterium bohemicum*, *Mycobacterium bovis*, *Mycobacterium branderi*, *Mycobacterium brumae*, *Mycobacterium celatum*, *Mycobacterium chubense*, *Mycobacterium confluentis*, *Mycobacterium conspicuum*, *Mycobacterium cookii*, *Mycobacterium flavescens*, *Mycobacterium gadium*, *Mycobacterium gastri*, *Mycobacterium genavense*, *Mycobacterium gordonae*, *Mycobacterium goodii*, *Mycobacterium haemophilum*, *Mycobacterium hassicum*, *Mycobacterium intracellulare*, *Mycobacterium interjectum*, *Mycobacterium heidelberense*, *Mycobacterium lentiflavum*, *Mycobacterium malmoense*, *Mycobacterium mucogenicum*, *Mycobacterium microti*, *Mycobacterium mucogenicum*, *Mycobacterium neoaurum*, *Mycobacterium nonchromogenicum*, *Mycobacterium peregrinum*, *Mycobacterium phlei*, *Mycobacterium scrofulaceum*, *Mycobacterium shimoidei*, *Mycobacterium simiae*, *Mycobacterium szulgai*, *Mycobacterium terrae*, *Mycobacterium thermoresistabile*, *Mycobacterium triplex*, *Mycobacterium triviale*, *Mycobacterium tusciae*, *Mycobacterium ulcerans*, *Mycobacterium vaccae*, *Mycobacterium wolinskyi* and *Mycobacterium xenopi*);

*Haemophilus* (e.g. *Haemophilus influenzae*, *Haemophilus ducreyi*, *Haemophilus aegyptius*, *Haemophilus parainfluenzae*, *Haemophilus haemolyticus* and *Haemophilus parahaemolyticus*);

*Actinobacillus* (e.g. *Actinobacillus actinomycetemcomitans*, *Actinobacillus equuli*, *Actinobacillus hominis*, *Actinobacillus lignieresii*, *Actinobacillus suis* and *Actinobacillus ureae*);

*Actinomyces* (e.g. *Actinomyces israelii*);
*Brucella* (e.g. *Brucella abortus*, *Brucella canis*, *Brucella melintensis* and *Brucella suis*);
*Campylobacter* (e.g. *Campylobacter jejuni*, *Campylobacter coli*, *Campylobacter lari* and *Campylobacter fetus*);
*Listeria monocytogenes*;
*Vibrio* (e.g. *Vibrio cholerae* and *Vibrio parahaemolyticus*, *Vibrio alginolyticus*, *Vibrio carchariae*, *Vibrio fluvialis*, *Vibrio furnissii*, *Vibrio hollisae*, *Vibrio metschnikovii*, *Vibrio mimicus* and *Vibrio vulnificus*);

*Erysipelothrix rhusopathiae;*

Corynebacteriaceae (e.g. *Corynebacterium diphtheriae, Corynebacterium jeikeum* and *Corynebacterium urealyticum*);

Spirochaetaceae, such as *Borrelia* (e.g. *Borrelia recurrentis, Borrelia burgdorferi, Borrelia afzelii, Borrelia andersonii, Borrelia bissettii, Borrelia garinii, Borrelia japonica, Borrelia lusitaniae, Borrelia tanukii, Borrelia turdi, Borrelia valaisiana, Borrelia caucasica, Borrelia crocidurae, Borrelia duttoni, Borrelia graingeri, Borrelia hermsii, Borrelia hispanica, Borrelia latyschewii, Borrelia mazzottii, Borrelia parkeri, Borrelia persica, Borrelia turicatae* and *Borrelia venezuelensis*) and *Treponema* (*Treponema pallidum* ssp. *pallidum, Treponema pallidum* ssp. *endemicum, Treponema pallidum* ssp. *pertenue* and *Treponema carateum*);

*Pasteurella* (e.g. *Pasteurella aerogenes, Pasteurella bettyae, Pasteurella canis, Pasteurella dagmatis, Pasteurella gallinarum, Pasteurella haemolytica, Pasteurella multocida multocida, Pasteurella multocida gallicida, Pasteurella multocida septica, Pasteurella pneumotropica* and *Pasteurella stomatis*);

*Bordetella* (e.g. *Bordetella bronchiseptica, Bordetella hinzii, Bordetella holmseii, Bordetella parapertussis, Bordetella pertussis* and *Bordetella trematum*);

Nocardiaceae, such as *Nocardia* (e.g. *Nocardia asteroides* and *Nocardia brasiliensis*);

*Rickettsia* (e.g. *Ricksettsii* or *Coxiella burnetii*);

*Legionella* (e.g. *Legionalla anisa, Legionalla birminghamensis, Legionalla bozemanfi, Legionalla cincinnatiensis, Legionalla dumoffii, Legionalla feelefi, Legionalla gormanfi, Legionalla hackeliae, Legionalla israelensis, Legionalla jordanis, Legionalla lansingensis, Legionalla longbeachae, Legionalla maceachernii, Legionalla micdadei, Legionalla oakridgensis, Legionalla pneumophila, Legionalla sainthelensi, Legionalla tucsonensis* and *Legionalla wadsworthii*);

*Moraxella catarrhalis;*

*Stenotrophomonas maltophilia;*

*Burkholderia cepacia;*

*Francisella tularensis;*

*Gardnerella* (e.g. *Gardneralla vaginalis* and *Gardneralla mobiluncus*);

*Streptobacillus moniliformis;*

Flavobacteriaceae, such as *Capnocytophaga* (e.g. *Capnocytophaga canimorsus, Capnocytophaga cynodegmi, Capnocytophaga gingivalis, Capnocytophaga granulosa, Capnocytophaga haemolytica, Capnocytophaga ochracea* and *Capnocytophaga sputigena*);

*Bartonella* (*Bartonella baciffiformis, Bartonella clarridgeiae, Bartonella elizabethae, Bartonella henselae, Bartonella quintana* and *Bartonella vinsonii arupensis*);

*Leptospira* (e.g. *Leptospira biflexa, Leptospira borgpetersenii, Leptospira inadai, Leptospira interrogans, Leptospira kirschneri, Leptospira noguchii, Leptospira santarosai* and *Leptospira weilii*);

*Spirillium* (e.g. *Spirillum minus*);

*Baceteroides* (e.g. *Bacteroides caccae, Bacteroides capillosus, Bacteroides coagulans, Bacteroides distasonis, Bacteroides eggerthii, Bacteroides forsythus, Bacteroides fragilis, Bacteroides merdae, Bacteroides ovatus, Bacteroides putredinis, Bacteroides pyogenes, Bacteroides splanchinicus, Bacteroides stercoris, Bacteroides tectus, Bacteroides thetaiotaomicron, Bacteroides uniformis, Bacteroides ureolyticus* and *Bacteroides vulgatus*);

*Prevotella* (e.g. *Prevotella bivia, Prevotella buccae, Prevotella corporis, Prevotella dentalis* (*Mitsuokella dentalis*), *Prevotella denticola, Prevotella disiens, Prevotella enoeca, Prevotella heparinolytica, Prevotella intermedia, Prevotella loeschfi, Prevotella melaninogenica, Prevotella nigrescens, Prevotella oralis, Prevotella oris, Prevotella oulora, Prevotella tannerae, Prevotella venoralis* and *Prevotella zoogleoformans*);

*Porphyromonas* (e.g. *Porphyromonas asaccharolytica, Porphyromonas cangingivalis, Porphyromonas canons, Porphyromonas cansulci, Porphyromonas catoniae, Porphyromonas circumdentaria, Porphyromonas crevioricanis, Porphyromonas endodontalis, Porphyromonas gingivalis, Porphyromonas gingivicanis, Porphyromonas levii* and *Porphyromonas macacae*);

*Fusobacterium* (e.g. *F. gonadiaformans, F. mortiferum, F. naviforme, F. necrogenes, F. necrophorum necrophorum, F. necrophorum fundiliforme, F. nucleatum nucleatum, F. nucleatum fusiforme, F. nucleatum polymorphum, F. nucleatum vincentii, F. periodonticum, F. russii, F. ulcerans* and *F. varium*);

*Chlamydia* (e.g. *Chlamydia trachomatis*);

*Chlamydophila* (e.g. *Chlamydophila abortus* (*Chlamydia psittaci*), *Chlamydophila pneumoniae* (*Chlamydia pneumoniae*) and *Chlamydophila psittaci* (*Chlamydia psittaci*));

*Leuconostoc* (e.g. *Leuconostoc citreum, Leuconostoc cremoris, Leuconostoc dextranicum, Leuconostoc lactis, Leuconostoc mesenteroides* and *Leuconostoc pseudomesenteroides*);

*Gemella* (e.g. *Gemella bergeri, Gemella haemolysans, Gemella morbillorum* and *Gemella sanguinis*); and

*Ureaplasma* (e.g. *Ureaplasma parvum* and *Ureaplasma urealyticum*).

Thus, compositions of the invention may be used to kill any of the above-mentioned bacterial organisms.

Particular bacteria that may be mentioned in this respect include:

Bacillaceae, such as *Bacillus anthracis, Bacillus subtilis, Bacillus thuringiensis, Bacillus stearothermophilus* and *Bacillus cereus;*

Staphylococci, such as *Staph. aureus* (either Methicillin-sensitive (i.e. MSSA) or Methicillin-resistant (i.e. MRSA)) and *Staph. epidermidis;*

*Acinetobacter* (e.g. *A. baumanii, A. calcoaceticus, A. haemolyticus, A. johnsonii, A. junii, A. lwoffi* and *A. radioresistens*);

Enterobacteriaceae, such as *Escherichia coli, Klebsiella* (e.g. *Klebs. pneumoniae* and *Klebs. oxytoca*) and *Proteus* (e.g. *Pr. mirabilis, Pr. rettgeri* and *Pr. vulgaris*); or

*Pseudomonas* (e.g. *Ps. aeruginosa, Ps. maltophilia* (*Stenotrophomonas maltophilia*), *Ps. alcaligenes, Ps. chlororaphis, Ps. fluorescens, Ps. luteola. Ps. mendocina, Ps. monteilii, Ps. oryzihabitans, Ps. pertocinogena, Ps. pseudalcaligenes, Ps. putida* and *Ps. stutzeri*).

Particular bacterial infections that may be mentioned in relation to the fifth to eighth aspects of the invention include infections with:

Bacillaceae, such as *Bacillus anthracis, Bacillus subtilis, Bacillus thuringiensis, Bacillus stearothermophilus* and *Bacillus cereus;*

Staphylococci, such as *Staph. aureus* (either Methicillin-sensitive (i.e. MSSA) or Methicillin-resistant (i.e. MRSA)) and *Staph. epidermidis;*

*Acinetobacter* (e.g. *A. baumanii, A. calcoaceticus, A. haemolyticus, A. johnsonii, A. junii, A. lwoffi* and *A. radioresistens*);

Enterobacteriaceae, such as *Escherichia coli, Klebsiella* (e.g. *Klebs. pneumoniae* and *Klebs. oxytoca*) and *Proteus* (e.g. *Pr. mirabilis, Pr. rettgeri* and *Pr. vulgaris*); or *Pseudomonas* (e.g. *Ps. aeruginosa, Ps. maltophilia* (*Stenotrophomonas maltophilia*), *Ps. alcaligenes, Ps. chlororaphis, Ps. fluorescens, Ps. luteola. Ps. mendocina, Ps. monteilii, Ps. oryzihabitans, Ps. pertocinogena, Ps. pseudalcaligenes, Ps. putida* and *Ps. stutzen*).

The compositions of the present invention are particularly advantageous as they are capable of inhibiting the growth, survival and reproduction of Gram negative bacteria, something which few existing antibacterial agents are able to do effectively. Thus, in particular embodiments of all of the methods disclosed herein, the bacteria are Gram negative bacteria.

In this respect, particular conditions that the compositions of the invention can be used to treat include tuberculosis (e.g. pulmonary tuberculosis, non-pulmonary tuberculosis (such as tuberculosis lymph glands, genito-urinary tuberculosis, tuberculosis of bone and joints, tuberculosis meningitis) and miliary tuberculosis), anthrax, abscesses, acne *vulgaris*, actinomycosis, bacilliary dysentry, bacterial conjunctivitis, bacterial keratitis, botulism, Buruli ulcer, bone and joint infections, bronchitis (acute or chronic), brucellosis, burn wounds, cat scratch fever, cellulitis, chancroid, cholangitis, cholecystitis, cutaneous diphtheria, cystic fibrosis, cystitis, diffuse panbronchiolitis, diphtheria, dental caries, diseases of the upper respiratory tract, empyema, endocarditis, endometritis, enteric fever, enteritis, epididymitis, epiglottitis, erysipelas, erysipeloid, erythrasma, eye infections, furuncles, *Gardnerella vaginitis*, gastrointestinal infections (gastroenteritis), genital infections, gingivitis, gonorrhoea, granuloma inguinale, Haverhill fever, infected burns, infections following dental operations, infections in the oral region, infections associated with prostheses, intraabdominal abscesses, Legionnaire's disease, leprosy, leptospirosis, listeriosis, liver abscesses, Lyme disease, lymphogranuloma venerium, mastitis, mastoiditis, meningitis and infections of the nervous system, mycetoma, nocardiosis (e.g. Madura foot), non-specific urethritis, opthalmia (e.g. opthalmia neonatorum), osteomyelitis, otitis (e.g. otitis externa and otitis media), orchitis, pancreatitis, paronychia, pelveoperitonitis, peritonitis, peritonitis with appendicitis, pharyngitis, phlegmons, pinta, plague, pleural effusion, pneumonia, postoperative wound infections, postoperative gas gangrene, prostatitis, pseudo-membranous colitis, psittacosis, pulmonary emphysema, pyelonephritis, pyoderma (e.g. impetigo), Q fever, rat-bite fever, reticulosis, Ritter's disease, salmonellosis, salpingitis, septic arthritis, septic infections, septicameia, sinusitis, skin infections (e.g. skin granulomas), syphilis, systemic infections, tonsillitis, toxic shock syndrome, trachoma, tularaemia, typhoid, typhus (e.g. epidemic typhus, murine typhus, scrub typhus and spotted fever), urethritis, wound infections, yaws, aspergillosis, candidiasis (e.g. oropharyngeal candidiasis, vaginal candidiasis or balanitis), cryptococcosis, *favus*, histoplasmosis, intertrigo, mucormycosis, *tinea* (e.g. *Tinea corporis, Tinea capitis, Tinea cruris, Tinea pedis* and *Tinea unguium*), onychomycosis, *Pityriasis versicolor*, ringworm and sporotrichosis.

Further conditions that may be mentioned in this respect include infections with MSSA, MRSA, *Staph. epidermidis, Strept. agalactiae, Strept. pyogenes, Escherichia coli, Klebs. pneumoniae, Klebs. oxytoca, Pr. mirabilis, Pr. rettgeri, Pr. vulgaris, Haemophilis influenzae, Enterococcus faecalis* or *Enterococcus faecium*.

The use of certain compositions of the invention in medicine, as well as the use of certain delivery agents in medicine, is, to the knowledge of the inventors, novel. In certain embodiments of the invention, the subject of the treatment or prevention methods is a mammal, particularly a human.

For the avoidance of doubt, references herein to compositions of the invention include references to all embodiments described above in relation to delivery agents of formulae I to IX.

Compositions of the invention may comprise a delivery agent and an antibacterial agent as separate agents or those two agents may be covalently bonded together. Where the delivery agent and antibacterial agent are separate agents, they are distinct chemical entities and may be provided in a form in which they are mixed together or in which they are not intermixed. Additionally, where the delivery agent and antibacterial agent are separate agents, they be separately (e.g. sequentially) delivered to a bacterial cell, or they may be combined prior to delivery. For example, where a composition of the invention is to be used to treat or prevent a bacterial infection in a subject, that subject may be administered each agent either separately or simultaneously.

Because they have a different mode of action to many conventional anti-bacterial agents, compositions of the invention may be particularly useful in the treatment of bacterial infections where the infective agent is resistant to one or more anti-bacterial agents having a different mode of action. In this respect, according to a ninth aspect of the invention there is provided a method of treating a bacterial infection, where the infective agent is resistant to one or more anti-bacterial agents that do not act by inhibiting bond formation in peptidoglycan, which method comprises administration of a therapeutically effective amount of a composition of the invention to a person having that infection.

The use of compositions of the invention in medicine includes their use as pharmaceuticals (both for human and veterinary use). The compositions of the present invention may also be useful in other fields of industry. For example, the compositions may be useful as plant protection products (i.e. in agriculture), in cosmetic products (e.g. in creams, lotions and ointments), and hygiene and sterilisation procedures (e.g. in scientific laboratories).

The compositions of the invention may also be used to facilitate the binding of a pharmaceutically active substance to a penicillin binding protein in a bacterial cell. Therefore in a tenth aspect of the invention, there is provided a method of binding a pharmaceutically active substance to a penicillin binding protein in a bacterial cell, which method involves delivering the pharmaceutically active substance and a delivery agent to the bacterial cell;

wherein the delivery agent is covalently bonded to the pharmaceutically active substance or is capable of binding to the pharmaceutically active substance;

wherein the pharmaceutically active substance is capable of binding to a transglycosylase domain of the penicillin binding protein; and wherein the delivery agent is capable of binding to a transmembrane domain of the penicillin binding protein.

In this context, the term binding means that the pharmaceutically active substance is held in close proximity to a transglycosylase domain of a penicillin binding protein in a bacterial cell wall, or may interact with the transglycosylase domain by way of one or more hydrogen bonds.

As a result of binding to a penicillin binding protein in a bacterial cell, or through other means, the compositions of the invention may also be used to modulate the activity of a penicillin binding protein in a bacterial cell. Therefore in an eleventh aspect of the invention, there is provided a method of modulating the activity of a penicillin binding protein in a bacterial cell, which method involves delivering a pharmaceutically active substance and a delivery agent to the bacterial cell;
  wherein the delivery agent is covalently bonded to the pharmaceutically active substance or is capable of binding to the pharmaceutically active substance;
  wherein the pharmaceutically active substance is capable of binding to a transglycosylase domain of the penicillin binding protein; and
  wherein the delivery agent is capable of binding to a transmembrane domain of the penicillin binding protein.

In particular embodiments, the modulation of the activity of a penicillin binding protein in a bacterial cell may be the inhibition of the activity of that penicillin binding protein.

In certain embodiments, the methods of binding a pharmaceutically active substance to a penicillin binding protein and the methods of modulating the activity of a penicillin binding protein may be performed in vivo or ex vivo. For example, the methods may be used in the fields of agriculture, cosmetics, hygiene and general scientific research.

The delivery agents described hereinbefore may be capable of enhancing the efficacy of new and existing antibacterial agents due to their ability to bind to the structures in a bacterial cell membrane (thereby allowing them to facilitate in bringing an antibacterial agent into close proximity with structures in the bacterial cell wall, and potentially aiding in delivering the antibacterial agent into the cytoplasmic region of the cell). Thus in a twelfth aspect of the invention, there is provided a method of enhancing the antibacterial effectiveness of an antibacterial agent, which method involves bringing the antibacterial agent into association with a delivery agent as defined herein. By the use of the term "bringing into association" it is meant that the delivery agent and the antibacterial agent may be separate agents or may be covalently bonded together. Where they are separate agents, they be separately (e.g. sequentially) delivered to a bacterial cell, or they may be combined prior to delivery.

The compositions of the invention will normally be administered orally, subcutaneously, intravenously, intraarterially, transdermally, intranasally, by inhalation, or by any other parenteral route, in the form of pharmaceutical preparations comprising the active ingredient either as a free base or a non-toxic organic or inorganic acid addition salt, in a pharmaceutically acceptable dosage form. Depending upon the disorder and patient to be treated, as well as the route of administration, the compositions may be administered at varying doses.

According to a thirteenth aspect of the invention there is thus provided a pharmaceutical formulation including a composition of the invention in admixture with a pharmaceutically acceptable adjuvant, diluent or carrier. Such formulations may be used for the treatment or prevention of bacterial infections. Thus, in one embodiment of this aspect of the invention there is provided a pharmaceutical formulation including, in admixture with a pharmaceutically acceptable adjuvant, diluent or carrier, a composition of the invention and optionally one or more other chemical agents that are known to be effective in treating or preventing bacterial infections.

Compositions of the invention may comprise a delivery agent and an antibacterial agent as separate agents (i.e. where the two agents are not covalently bonded together).

According to an embodiment of this aspect of the invention, there is provided a combination product comprising:
  (A) a delivery agent, as hereinbefore defined; and
  (B) an antibacterial agent as hereinbefore defined,
    wherein each of components (A) and (B) is formulated in admixture with a pharmaceutically-acceptable adjuvant, diluent or carrier.

Such combination products provide for the administration of a delivery agent in conjunction with an antibacterial agent, and may thus be presented either as separate formulations, wherein at least one of those formulations comprises a delivery agent, and at least one comprises an antibacterial agent, or may be presented (i.e. formulated) as a combined preparation (i.e. presented as a single formulation including a delivery agent and an antibacterial agent).

Thus, there is further provided:
  (1) a pharmaceutical formulation including a delivery agent as hereinbefore defined, an antibacterial agent as hereinbefore defined, and a pharmaceutically-acceptable adjuvant, diluent or carrier; and
  (2) a kit of parts comprising components:
    (a) a pharmaceutical formulation including a delivery agent, as hereinbefore defined, in admixture with a pharmaceutically-acceptable adjuvant, diluent or carrier; and
    (b) a pharmaceutical formulation including an antibacterial agent, as hereinbefore defined, in admixture with a pharmaceutically-acceptable adjuvant, diluent or carrier,
  which components (a) and (b) are each provided in a form that is suitable for administration in conjunction with the other.

Suitable daily doses of the compositions of the invention in therapeutic treatment of humans are about 1 to 2000 mg/m$^2$.

The most effective mode of administration and dosage regimen for the compositions of the invention depends on several factors, including the particular condition being treated, the extent and localisation of that condition in the patient being treated, as well as the patient's state of health and their reaction to the compound being administered. Accordingly, the dosages of the compositions of the invention should be adjusted to suit the individual patient. Methods for determining the appropriate dose for an individual patient will be known to those skilled in the art.

Additionally, compositions of the invention may have the advantage that they may be more efficacious than, be less toxic than, have a broader range of activity than, be more potent than, produce fewer side effects than, or have other useful pharmacological properties over compositions known in the prior art. In particular, compositions of the invention may have the advantage that they are less toxic than compositions known in the prior art due to a reduction in the detrimental effects that the delivery agents may have on cell membrane (of the host organisms).

The invention will now be described in more detail by reference to the following, non-limiting, Figures and Examples.

FIGURES

FIG. 1: The structure of moenomycin A.

Figure 2:
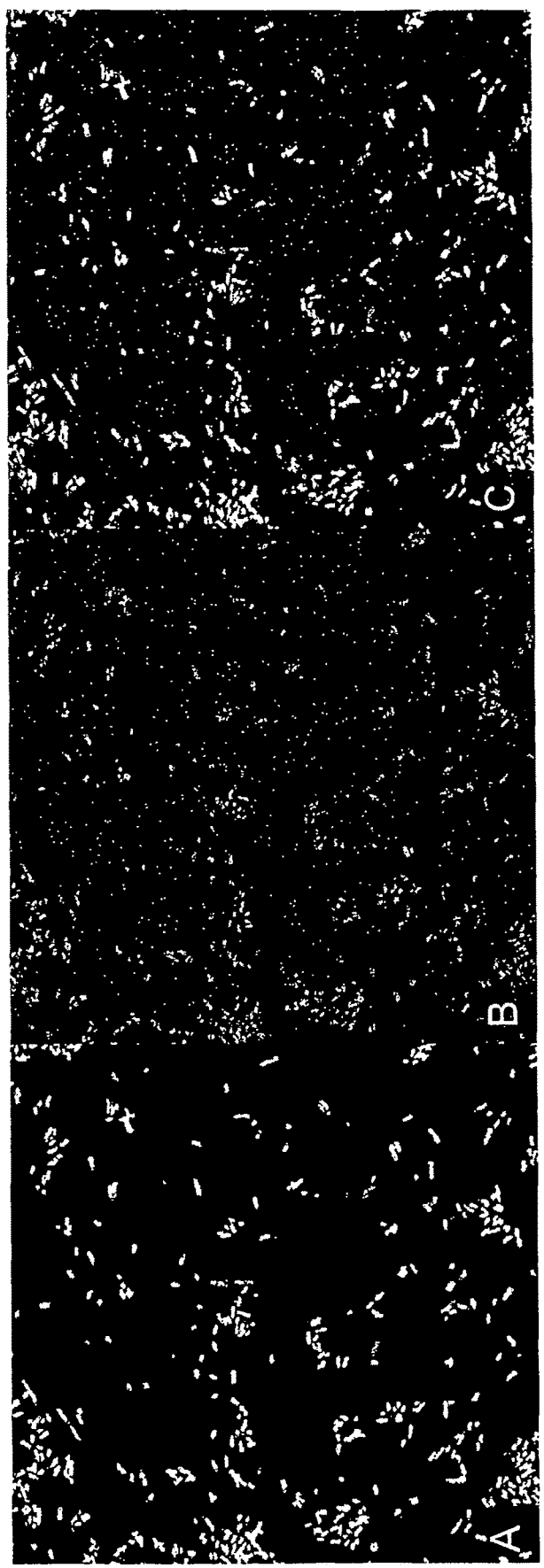

FIG. 2: Showing the peptide delivery of TAMRA to *E. coli* labelled with GFP. Confocal microscope images of GFP labelled *E. coli* after treatment with TAMRA labelled cell penetrating peptides. A *E. coli* labelled with GFP, B The same image area looking at TAMRA labelled peptides. C an overlay of images A and B.

BIOLOGICAL TESTS

The effects of compounds of the invention in relation to inhibiting the growth of various microorganisms was determined using methods known to those skilled in the art, for example in vitro methods as described in *J. Med. Chem.* 47, 2133-2156 (2004) and in vivo methods as described in *J. Med. Microbiol.* 46, 208-213 (1997), the disclosures of which documents are hereby incorporated by reference.

MIC Testing

The bacteria were grown in 5 ml of Mueller Hinton Broth overnight at 37° C.

The inhibitor was tested on its own or in conjunction with a cell penetrating peptide (CPP).

When tested with a CPP they were incubated together at room temperature for 1 hour before use.

Delivery agents (Compound 5, Compound 6, and 7) were used at a 1:2 ratio. CPP Linker was used at a 1:3 ratio or a 1:10 ratio where stated.

All dilutions were carried out using Mueller Hinton Broth.

The MIC tests were carried out across two 96 well plates unless otherwise stated.

100 µl of autoclaved Mueller Hilton Broth was added to wells 2-12 on plate 1 and 1-12 on plate 2.

200 µl of the inhibitor was added to well 1 at a concentration of 512 µg/ml.

100 µl of the inhibitor was taken from well 1 and pipetted into well 2.

The mixture was pipetted up and down three times before 100 µl was taken from well 2 and added to well 3.

This process was repeated until well 11 on plate 2.

100 µl was then taken up from well 11 and discarded ensuring that there was no inhibitor present in well 12 of plate 2.

The pipette tips were changed between each well so that the concentration was not affected by any inhibitor on the outside of the tips.

Each well was inoculated with 100 µl of bacteria that had been diluted to an $OD_{600\ nm}$ of 0.1.

This was repeated three times.

The 96 well plates were then incubated for 24 hours at 37° C.

The minimum inhibitory concentration (MIC) was determined to be the lowest concentration at which there was no growth visible.

To determine the minimum bactericidal concentration (MBC) 10 µl of the sample was pipetted onto a Muller Hinton agar plate containing no inhibitor.

This was done for each well in which there was no growth and the three wells above the MIC.

These were then incubated overnight and the MBC was determined by any growth from a sample corresponding to a well that had no visible growth.

Confocal Microscope

XL1 blue *E. coli* was used for this experiment as it was transformed with pJF40 so that it produced GFP.

Once the transformation had been completed, 5 ml overnights were inoculated with a single colony and grown up overnight (37° C., 180 rpm).

1 ml of bacteria was then spun down and the supernatant was removed.

The bacteria pellet as then re-suspended in 0.5 ml HBSS.

The labelled peptides were then added to each sample to achieve a final concentration of 10 µM of peptide.

The samples were incubated at room temperature for three hours.

The samples were then washed 5 times in 0.5 ml PBS by re-suspended the pellet and re-suspending in PBS.

After washing 10 µl of each sample was smeared onto a microscope slide ready for viewing on the confocal.

No fixation was used as the GFP bleaches quite quickly so the samples will not be able to be used for than once.

Toxicity Test Methods

*Galleria mellonella* Model

This model was used to test Moenomycin A and peptides in vivo both for toxicity and antimicrobial activity. Conjugates were also tested using the same methods.

*Galleria mellonella* were selected on the basis of being free of infection and signs of trauma, not beginning to pupate and weighing between 225 mgs and 275 mgs. All calculations were on the basis of an average weight of 250 mgs. The selected *Galleria mellonella* were swabbed with 70% ethanol prior to injection using a Hamilton 10 µl syringe using disposable needles. Tips were changed between solutions and between each *Galleria*. All injections were into the front left proleg unless otherwise stated.

Preliminary Testing

Ringers solution was chosen as a control, and all dilutions of bacteria, antimicrobials and peptides were carried out in this. Ringers supplemented with 20% DMSO was also used as a control to account for the DMSO used to dissolve Compound 6. Groups of 10 *Galleria* were used for these control groups and injected with 10 µl of the appropriate solution as previously described. These were then observed for 96 hours. The *Galleria* were deemed to be alive if there was movement in response to physical stimuli (touch).

The kill kinetics of *P. aeruginosa, S. aureus* and *A. baumannii* were also determined by injecting a set CFU into the *Galleria*, the aim was to ensure that the *Galleria* died within 36 hours but not less than 24.

To determine the appropriate antimicrobial concentration, a range was set up from 40 mg/kg to 0.5 mg/kg. Moenomycin was tested both singularly and in conjunction with either Compound 6 or 8; these two compounds were also tested separately. Groups of 2 were used for each test with control groups of 5 used to cover the whole experiment. The *Galleria* were injected as previously described. For toxicity testing of Moenomycin conjugates, the same procedure was followed with a concentration range up to 80 mg/kg.

To determine the appropriate concentration of antimicrobial in regards to treatment of *P. aeruginosa*, the *Galleria* were first injected with 10 µl of the appropriate concentration of bacteria as previously described. They were then treated within half an hour by injection into the first right pro-leg with the compound(s) being tested.

EXAMPLES

Example 1—Purification of Moenomycin A

Flavomycin (100 g) was extracted twice with methanol (400 mL) at room temperature for 16 h. The combined methanol extract was concentrated in vacuo and the residue was purified by silica gel chromatography with a gradient of 2-propanol:2 M ammonium hydroxide from 9.5:0.5 to 7:3. Moenomycin A eluted with the last gradient. The solvent was evaporated in vacuo and the obtained brown mass was lyophilized to give a brown solid. Further purification with RP-HPLC (Gemini C18) was performed with a gradient of ACN in water in 30 min to give moenomycin A as a white solid (400 mg).

Calculated mass: 1581.7. Found 789.5 (M/2−H$^+$); 1582.7 (M+H$^+$); 1604.6 (M+Na$^+$)

Example 2—Synthesis of Dendrimer Delivery Agents
Compounds 1~4 shown below were prepared using reported procedures from *J. Mater. Chem. B* 2014, 2, 2153-2167 (see Schemes 1 and 2).
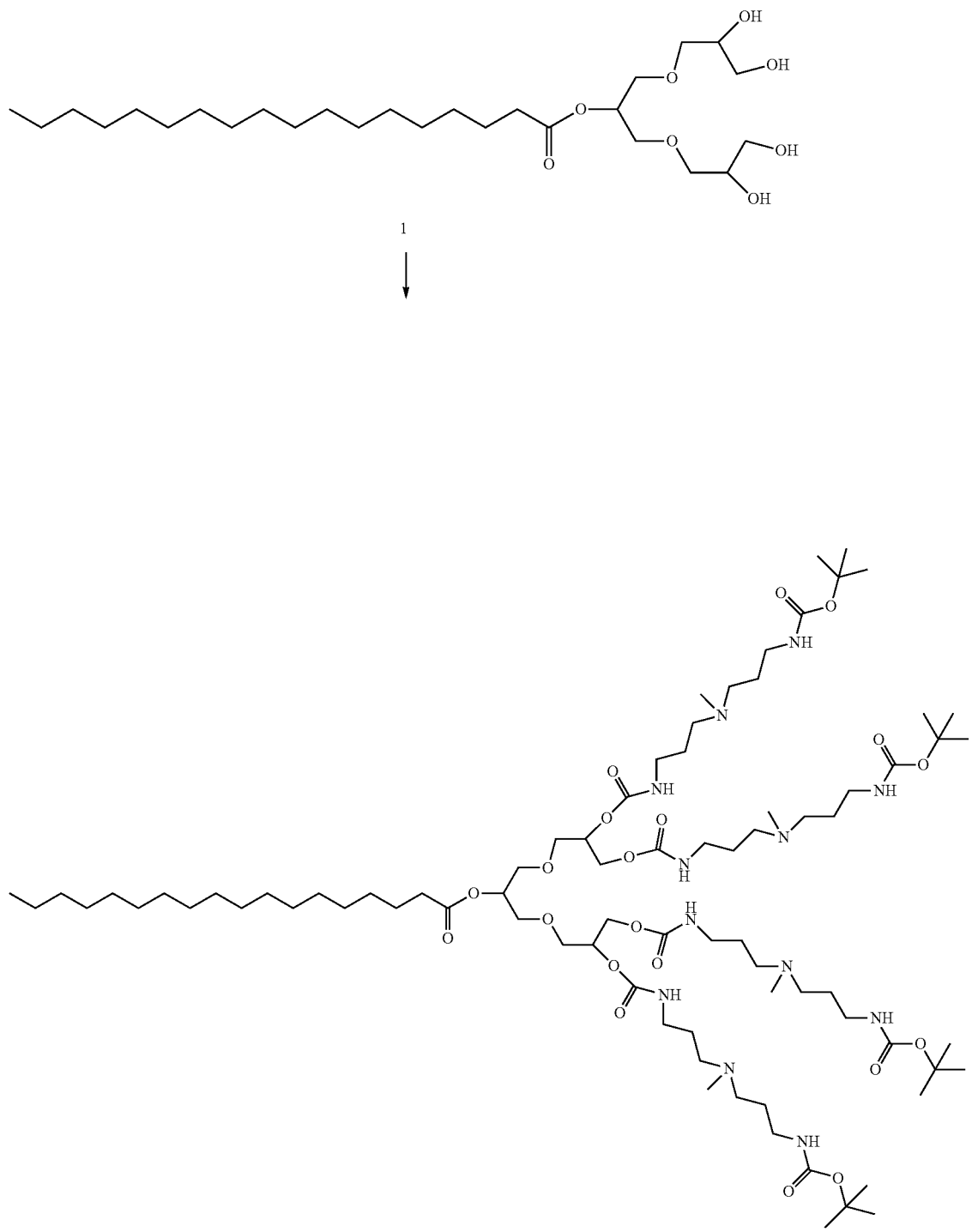

Scheme 2. Synthesis of Compound 4
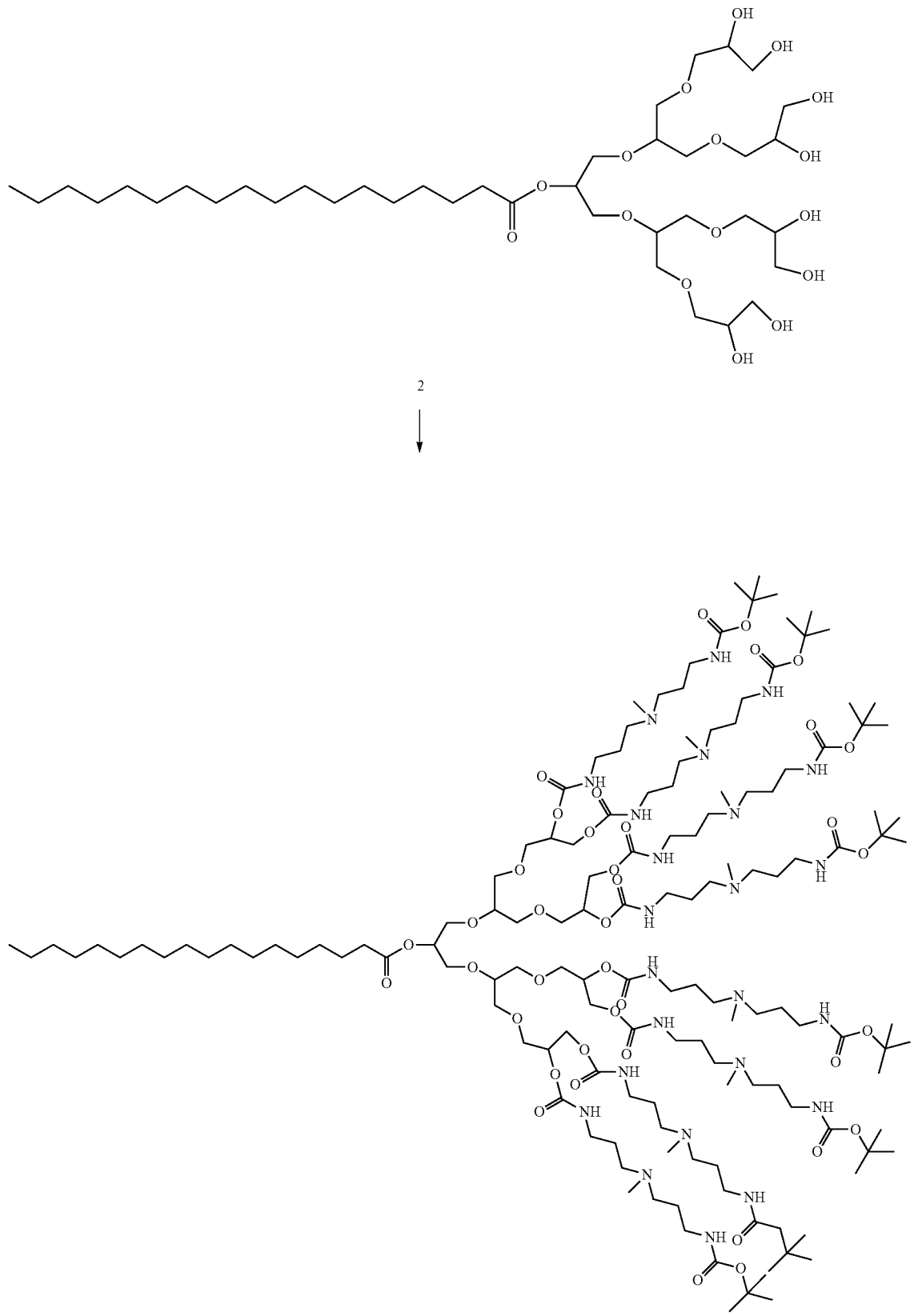

Example 3—General Procedure for the Synthesis of Compounds 3 and 4

Each solution of the crude compounds 1 (500 mg, 0.43 mmol) or 2 (175 mg, 0.08 mmol), which were dissolved in dry DCM (120 mL), was added dropwise over 2 h at 0° C. into a solution of mono-Boc-DAPMA (1.24 g, 5.08 mmol, 12 eq., dissolved in 50 mL dry DCM) employing dry reaction conditions. Immediately, the solution turned yellow due to the displacement of p-nitrophenol. A solution of DMAP (0.20 g, 1.69 mmol, 0.5 eq. per p-nitrophenyl branch) and DIPEA (0.15 mL, 1.69 mmol, 1.0 eq. per p-nitrophenyl branch) in dry DCM (30 mL) was added and the reaction mixtures were stirred at room temperature for 72 h. The solvent was then removed under reduced pressure. Purification was performed both by column chromatography (CHCl$_3$—MeOH—NH$_4$OH 90:9:1) and size exclusion chromatography (SEC) using a Sephadex™ LH-20 (CHCl$_3$—MeOH 1:1). Drying under high vacuum yielded the products 11 and 12 as yellowish oils.

Compound 3 was obtained as a yellowish viscous oil (1.57 g, 49%).

Compound 4 was obtained as a yellowish viscous oil (0.45 g, 40%).

Example 4—General Procedure for the Synthesis of Compounds 5 and 6

Compounds 5 and 6 were synthesised from compounds 3 and 4, respectively, according to the procedure below.

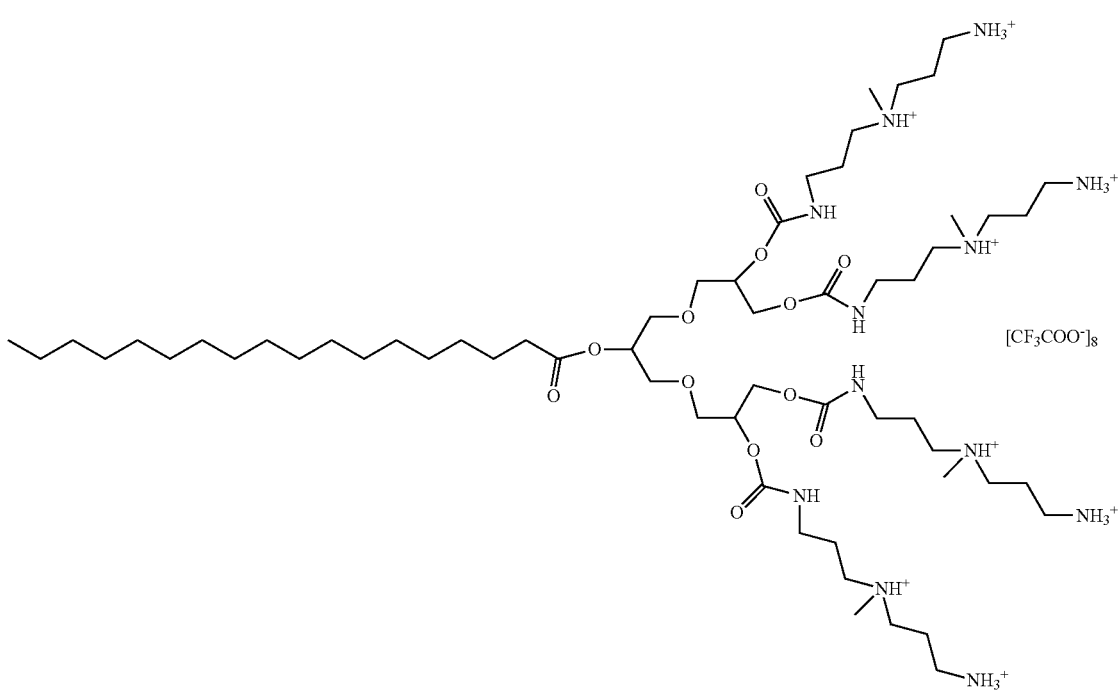

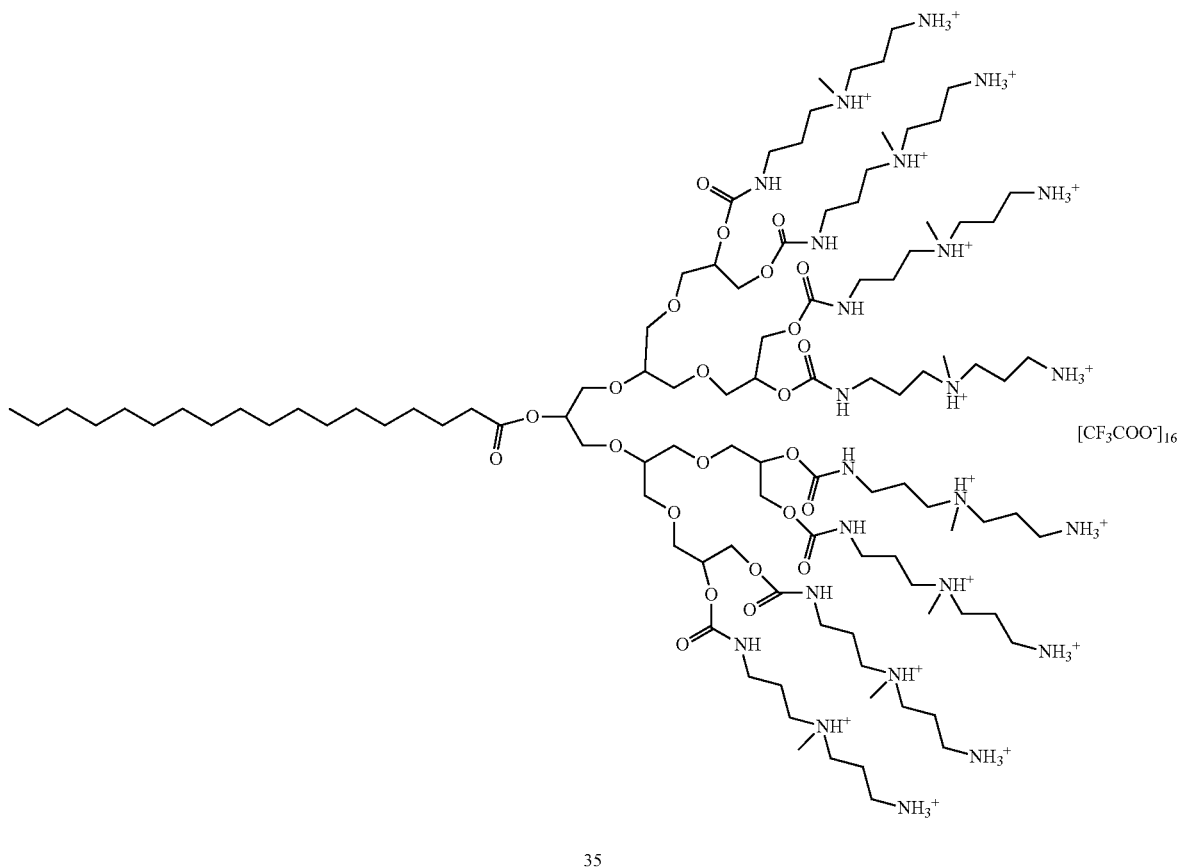

6

TFA (6.0 mL, excess) was slowly added to a solution of compounds 3 (0.10 g, 0.06 mmol) or 4 (0.10 g, 0.03 mmol) in DCM (6.0 mL) and stirred overnight at room temperature. The solvent was removed in vacuo and the residue washed alternately with hexane and diethyl ether. Purification was accomplished via SEC (Sephadex™ LH20, MeOH) to remove any trace amounts of impurities. Freeze drying yielded the compounds 5 and 6 as white foams.

Compound 5 was obtained as a white foam (98 mg, quant.).

Compound 6 was obtained as a white foam (131 mg, quant.).

Example 5—Guanidilation of PAMAM Dendrimer, 3,3',3'',3'''-(ethane-1,2-diylbis(azanetriyl)) tetrakis (N-(2-guanidinoethyl)propanamide) (Compound 7)

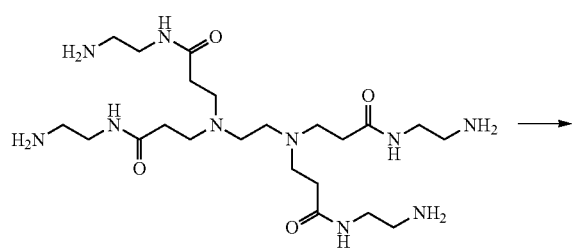

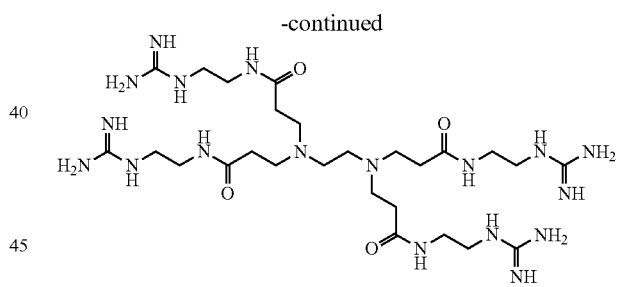

To a solution of PAMAM dendrimer (200 mg, 0.387 mmol from a solution of 20% in MeOH) in EtOH (1.5 mL), was added 1-H-pyrazole-1-carboxamidine hydrochloride (348.3 mg, 2.322 mmol). The reaction mixture was refluxed at 86° C. and stirred overnight. After stirring, the solvent was removed in vacuo. Extraction in DCM (3×3 mL) was performed and supernatant solution was removed.

Crude mass: 430 mg; crude yield: 78%
Calculated mass: 684.6. Found: 685.6 (M+H$^+$)

Example 6—Cell Penetration Studies

TAMRA dye and Confocal Microscopy was used to demonstrate the principle of compound mediated delivery to Gram negative bacteria. E. coli cells were label by transforming with pJF40 which vector which harbours a gene for Green fluorescent protein (GFP) when viewed under confocal microscopy (excited at 555 nm emission at 570 nm). This was used to clearly identify bacterial cells.

The same cells were treated with TAMRA labelled cell penetrating peptides (sequence: PLIYLRLLRGQF (SEQ ID NO: 21); excited at 555 nm emission at 570 nm) which fluoresced under a different wavelength which was used to follow the penetration of the dye into the bacteria. Control experiment where peptides were omitted showed no fluorescence.

Confocal microscope images of GFP labelled *E. coli* after treatment with TAMRA labelled cell penetrating peptides. A *E. coli* labelled with GFP, B The same image area looking at TAMRA labelled peptides. C an overlay of images A and B.

Example 7—General Procedure for the Synthesis of Compounds 8 to 19

General Procedure for Peptide Synthesis

Peptide syntheses was performed using standard Fmoc Solid Phase Peptide Synthesis (SPPS) protocols on Rink Amide Chemmatrix Resin, loading=0.49 mmol/g on a 0.1 mmol scale using a Biotage Initiator+Alstra fully automated microwave peptide synthesizer. All amino acid couplings were performed using 5 eq. Amino Acid with 5 eq. DIC/Oxyma in DMF as a coupling cocktail by irradiating at 70° C. for 5 min. Fmoc deprotection was performed using 20% piperidine in DMF by shaking for 3 min, followed by shaking for 10 min. 4×45 s washes were performed after each coupling cycle and 3×30 s washes were performed after each deprotection cycle.

Propiolic acid was coupled using 3 eq. of acid, 2.9 eq. of HATU and 6 eq. of DIPEA in DMF and shaking for 1 h.

Peptide cleavage was performed using TFA/TIS/H$_2$O=95:2.5:2.5 (3 mL/100 mg resin). For sequences containing 1 or 2 Arg groups, the cleavage time was 2 h. For 3 or higher Arg containing peptides, cleavage time was 5 h. Peptides were precipitated using cold Et$_2$O (−20° C.) by adding approximately 5× volume of the TFA used for cleavage and centrifuging at 7000 rpm at 0° C.

Analysis and Purification of Peptides/Conjugates:

All peptides/conjugates were analysed on a Thermo Scientific Dionex Ultimate 3000 RP-HPLC equipped with a Phenomenex Gemini NX C18 110 Å (150×4.6 mm) column using the following buffer systems: A: 0.1% HCOOH in milliQ water. B: ACN using a flow rate of 1 ml/min. The use of TFA was avoided as it can damage the phosphate group of Moenomycin A. The column was flushed with 100% A for 5 min prior to an injection and was flushed for 5 min with 95% B and 5% A after the run was finished.

Peptides and conjugates were analysed using the following gradient: 100% A for 2 min. 0-95% B in 15 min. 95% B for 5 min. 100% A for 4 min.

Peptides and conjugates were purified using the same gradient as mentioned above, on a Thermo Scientific Dionex Ultimate 3000 RP-HPLC with a flow rate of 5 mL/min using a Phenomenex Gemini NX C18 110 Å (150×10 mm) semi-prep column.

LC-MS data were collected on an Agilent 1100 Series instrument with a Phenomenex Kinetex C18 100 Å column (150×4.6 mm, 5 μm at 35° C.) connected to an ESMSD type VL mass detector with a flow rate of 1.5 ml/min was used with the following solvent systems: (A): 0.1% HCOOH in H$_2$O and (B) MeCN. The column was flushed with 100% A for 2 min, then a gradient from 0 to 100% B over 6 min was used, followed by 2 min of flushing with 100% B.

The following compounds were synthesised by this method.

| Comp. number | Peptide Derivative | Chemical Formula | Exact Mass | Mass found |
|---|---|---|---|---|
| 8 | 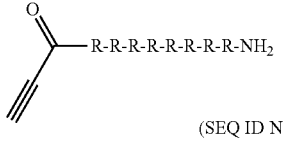R-R-R-R-R-R-R-NH$_2$ (SEQ ID NO: 1) | C$_{51}$H$_{99}$N$_{33}$O$_9$ | 1317.83 | 1453.58 [M + CF$_3$CO$_2^-$ + Na$^+$] |
| 9 | 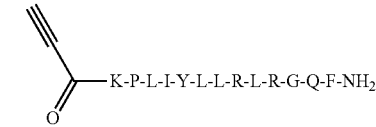K-P-L-I-Y-L-L-R-L-R-G-Q-F-NH$_2$ (SEQ ID NO: 2) | C$_{81}$H$_{130}$N$_{22}$O$_{16}$ | 1667.00 | 1667.87 |
| 10 | 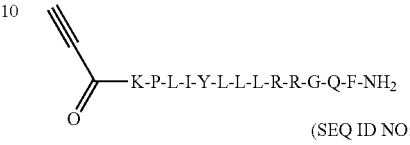K-P-L-I-Y-L-L-R-G-Q-F-NH$_2$ (SEQ ID NO: 3) | C$_{81}$H$_{130}$N$_{22}$O$_{16}$ | 1667.00 | 1667.67 |
| 12 | 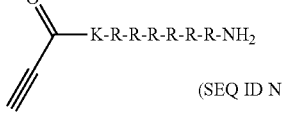K-R-R-R-R-R-R-NH$_2$ (SEQ ID NO: 5) | C$_{45}$H$_{87}$N$_{27}$O$_8$ | 1133.72 | 1133.9 [M + H$^+$] |
| 13 | H-P-L-I-Y-L-K-L-L-K-G-Q-F-NH$_2$ (SEQ ID NO: 6) | C$_{72}$H$_{118}$N$_{16}$O$_{14}$ | 1430.90 | 1432.94 [M + H$^+$] |

-continued

| Comp. number | Peptide Derivative | Chemical Formula | Exact Mass | Mass found |
|---|---|---|---|---|
| 14 | (propynoyl)-P-L-I-Y-L-R-L-L-R-G-Q-F-NH$_2$ (SEQ ID NO: 21) | $C_{75}H_{118}N_{20}O_{15}$ | 1538.91 | 1538.90 |
| 15 | (propynoyl)-P-L-I-Y-L-L-R-L-R-G-Q-F-NH$_2$ (SEQ ID NO: 36) | $C_{75}H_{118}N_{20}O_{15}$ | 1538.91 | 1674.51 [M + CF$_3$CO$_2^-$ + Na$^+$] |
| 16 | (propynoyl)-P-L-I-Y-L-L-L-R-R-G-Q-F-NH$_2$ (SEQ ID NO: 37) | $C_{75}H_{118}N_{20}O_{15}$ | 1538.91 | 1674.55 [M + CF$_3$CO$_2^-$ + Na$^+$] |
| 17 | H-P-L-I-Y-L-R-L-L-R-G-Q-F-NH$_2$ (SEQ ID NO: 21) | $C_{72}H_{118}N_{20}O_{14}$ | 1486.91 | 1487.4 |
| 18 | H-P-L-I-Y-L-L-L-R-R-G-Q-F-NH$_2$ (SEQ ID NO: 37) | $C_{72}H_{118}N_{20}O_{14}$ | 1486.91 | 1487.43 |
| 19 | (propynoyl)-K-P-L-I-Y-L-R-L-L-R-G-Q-F-NH$_2$ (SEQ ID NO: 29) | $C_{81}H_{130}N_{22}O_{16}$ | 1667.00 | 1667.87 |

Example 8—General Procedure for the Synthesis of Peptide-Moenomycin A Conjugates Via A Ring Conjugation (Compounds 20 to 39)

Peptide Synthesis:

Peptide synthesis was performed using standard Fmoc Solid Phase Peptide Synthesis (SPPS) protocols on Rink Amide Chemmatrix Resin, loading=0.49 mmol/g on a 0.1 mmol scale using a Biotage Initiator+Alstra fully automated microwave peptide synthesizer. All amino acid couplings were performed using 5 eq. Amino Acid with 5 eq. DIC/Oxyma in DMF as a coupling cocktail by irradiating at 70° C. for 5 min. Fmoc deprotection was performed using 20% piperidine in DMF by irradiating at 70° C. for 3 min, followed by shaking at r.t. for 10 min. 4×45 s washes were performed after each coupling cycle and 3×30 s washes were performed after each deprotection cycle.

Peptide cleavage was performed using TFA/TIS/H$_2$O=95:2.5:2.5 (3 mL/100 mg resin). For sequences containing 1 or 2 Arg groups, the cleavage time was 2 h. For 3 or higher Arg containing peptides, cleavage time was 5 h. Peptides were precipitated using cold Et$_2$O (−20° C.) by adding approximately 5× volume of the TFA used for cleavage and centrifuging at 7000 rpm at 0° C.

Fmoc-ε-Ahx-OH and (9H-fluoren-9-yl)methyl (2-(2-(2-aminoethoxy)ethoxy)ethyl)-carbamate and 5-Amino-2-Nitrobenzoic acid were coupled using Amino acid, HATU and DIPEA in DMF.

General Procedure for Coupling Peptides to Moenomycin a (15 mg Scale):

The peptides were coupled using the procedure described in Eur. J. Org. Chem. 2002, 1149-1162.

Analysis and Purification of Peptides/Conjugates:

All peptides/conjugates were analysed on a Thermo Scientific Dionex Ultimate 3000 RP-HPLC equipped with a Phenomenex Gemini NX C18 110 Å (150×4.6 mm) column using the following buffer systems: A: 0.1% HCOOH in milliQ water. B: ACN using a flow rate of 1 ml/min. The use of TFA was avoided as it can damage the phosphate group of Moenomycin A. The column was flushed with 100% A for 5 min prior to an injection and was flushed for 5 min with 95% B and 5% A after the run was finished.

Peptides and conjugates were analysed using the following gradient: 100% A for 2 min. 0-95% B in 15 min. 95% B for 5 min. 100% A for 4 min.

Peptides and conjugates were purified using the same gradient as mentioned above, on a Thermo Scientific Dionex Ultimate 3000 RP-HPLC with a flow rate of 5 mL/min using a Phenomenex Gemini NX C18 110 Å (150×10 mm) semi-prep column.

LC-MS data were collected on an Agilent 1100 Series instrument with a Phenomenex Kinetex C18 100 Å column (150×4.6 mm, 5 μm at 35° C.) connected to an ESMSD type VL mass detector with a flow rate of 1.5 ml/min was used with the following solvent systems: (A): 0.1% HCOOH in H$_2$O and (B) MeCN. The column was flushed with 100% A for 2 min, then a gradient from 0 to 100% B over 6 min was used, followed by 2 min of flushing with 100% B.

Complete List of Peptides Synthesized (Peptide Nos. 1 to 17):

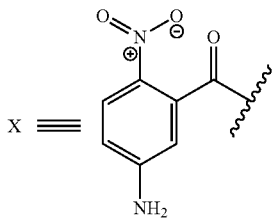

| Peptide No. | Peptide-linker structure | Chemical Formula | Exact Mass | Mass found |
|---|---|---|---|---|
| 1. | [structure]-R-R-R-R-NH$_2$ (SEQ ID NO: 15) | $C_{37}H_{66}N_{20}O_8$ | 918.54 | 919.54 |
| 2. | X-R-R-R-R-R-R-R-R-NH$_2$ (SEQ ID NO: 1) | $C_{55}H_{103}N_{35}O_{11}$ | 1429.86 | 1430 |
| 3. | [structure]-R-R-R-R-R-R-R-R-NH$_2$ (SEQ ID NO: 1) | $C_{61}H_{114}N_{36}O_{12}$ | 1542.94 | 1543 |
| 4. | [structure]-R-R-R-R-R-R-R-R-NH$_2$ (SEQ ID NO: 1) | $C_{67}H_{125}N_{37}O_{13}$ | 1656.03 | 1655.8 |
| 5. | [structure]-R-R-R-R-R-R-R-R-R-NH$_2$ (SEQ ID NO: 16) | $C_{67}H_{126}N_{40}O_{13}$ | 1699.04 | 1698.9 |
| 6. | [structure]-R-R-R-R-R-R-R-R-R-R-NH$_2$ (SEQ ID NO: 17) | $C_{73}H_{138}N_{44}O_{14}$ | 1855.14 | 1855.5 |
| 7. | [structure]-K-K-R-R-R-R-R-R-R-R-NH$_2$ (SEQ ID NO: 18) | $C_{73}H_{138}N_{40}O_{14}$ | 1799.13 | 1799.4 |
| 8. | X-K-R-R-K-R-R-K-R-R-NH$_2$ (SEQ ID NO: 4) | $C_{61}H_{115}N_{33}O_{12}$ | 1501.94 | 1502 |
| 9. | [structure]-K-R-R-K-R-R-K-R-R-NH$_2$ (SEQ ID NO: 4) | $C_{67}H_{126}N_{34}O_{13}$ | 1615.02 | 1614.6 |
| 10. | [structure]-K-R-R-K-R-R-K-R-R-NH$_2$ (SEQ ID NO: 4) | $C_{73}H_{137}N_{35}O_{14}$ | 1728.11 | 1728.6 |
| 11. | X-K-K-K-K-K-R-NH$_2$ (SEQ ID NO: 14) | $C_{43}H_{79}N_{17}O_9$ | 977.62 | 977.5 |

-continued

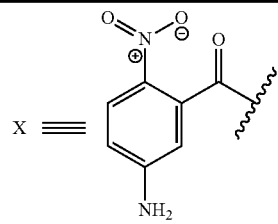

| Peptide No. | Peptide-linker structure | Chemical Formula | Exact Mass | Mass found |
|---|---|---|---|---|
| 12. | X-HN-(CH2)-C(O)-K-K-K-K-K-R-NH2 (SEQ ID NO: 14) | $C_{49}H_{90}N_{18}O_{10}$ | 1090.71 | 1090.6 |
| 13. | X-NH-(CH2)-C(O)-NH-(CH2)-C(O)-K-K-K-K-K-R-NH2 (SEQ ID NO: 14) | $C_{55}H_{101}N_{19}O_{11}$ | 1203.79 | 1203.9 |
| 14. | X-NH-(CH2)-C(O)-NH-(CH2)-C(O)-K-K-R-K-K-K-K-R-NH2 (SEQ ID NO: 19) | $C_{66}H_{123}N_{25}O_{13}$ | 1487.99 | 1487.8 |
| 15. | X-HN-(CH2)-C(O)-R-R-W-W-R-R-W-R-R-NH2 (SEQ ID NO: 20) | $C_{82}H_{120}N_{34}O_{13}$ | 1788.98 | 1789.5 |
| 16. | X-P-L-I-Y-L-R-L-L-R-G-Q-F-NH2 (SEQ ID NO: 21) | $C_{79}H_{122}N_{22}O_{17}$ | 1650.94 | 1651 |
| 17. | [structure with nitro-aminobenzamide-arginine] | $C_{13}H_{19}N_7O_4$ | 337.15 | 338.1 [M + H+] |

Complete List of Conjugates Synthesized (Compounds 20 to 34):

| Comp. No. | Conjugate description | Chemical Formula | Exact Mass | Mass found |
|---|---|---|---|---|
| 20. | Conjugate with peptide 1 | $C_{106}H_{171}N_{26}O_{42}P$ | 2511.18 | 2512.2 |
| 21. | Conjugate with peptide 2 | $C_{124}H_{208}N_{41}O_{45}P$ | 3022.50 | 3022.8 |
| 22. | Conjugate with peptide 3 | $C_{130}H_{219}N_{42}O_{46}P$ | 3135.58 | 3137.1 |
| 23. | Conjugate with peptide 4 | $C_{136}H_{230}N_{43}O_{47}P$ | 3248.67 | 3249.6 |
| 24. | Conjugate with peptide 5 | $C_{136}H_{231}N_{46}O_{47}P$ | 3291.68 | 3292.8 |
| 25. | Conjugate with peptide 6 | $C_{142}H_{243}N_{50}O_{48}P$ | 3447.78 | 3448.5 |
| 26. | Conjugate with peptide 7 | $C_{136}H_{231}N_{40}O_{47}P$ | 3207.67 | 3208.2 |
| 27. | Conjugate with peptide 8 | $C_{130}H_{220}N_{39}O_{46}P$ | 3094.58 | 3094.8 |
| 28. | Conjugate with peptide 9 | $C_{142}H_{243}N_{46}O_{48}P$ | 3391.77 | 3392.1 |

-continued

| Comp. No. | Conjugate description | Chemical Formula | Exact Mass | Mass found |
|---|---|---|---|---|
| 29. | Conjugate with peptide 10 | $C_{142}H_{242}N_{41}O_{48}P$ | 3320.75 | 3322 |
| 30. | Conjugate with peptide 11 | $C_{112}H_{184}N_{23}O_{43}P$ | 2570.27 | 2570.8 |
| 31. | Conjugate with peptide 12 | $C_{118}H_{195}N_{24}O_{44}P$ | 2683.35 | 2683.8 |
| 32. | Conjugate with peptide 13 | $C_{124}H_{206}N_{25}O_{45}P$ | 2796.43 | 2797 |
| 33. | Conjugate with peptide 16 | $C_{148}H_{227}N_{28}O_{51}P$ | 3243.58 | 3244.4 |
| 34. | Conjugate with peptide 17 | $C_{82}H_{124}N_{13}O_{38}P$ | 1929.79 | 1930 |

General Structure of a Peptide-Moenomycin A Conjugate Via A Ring Conjugation

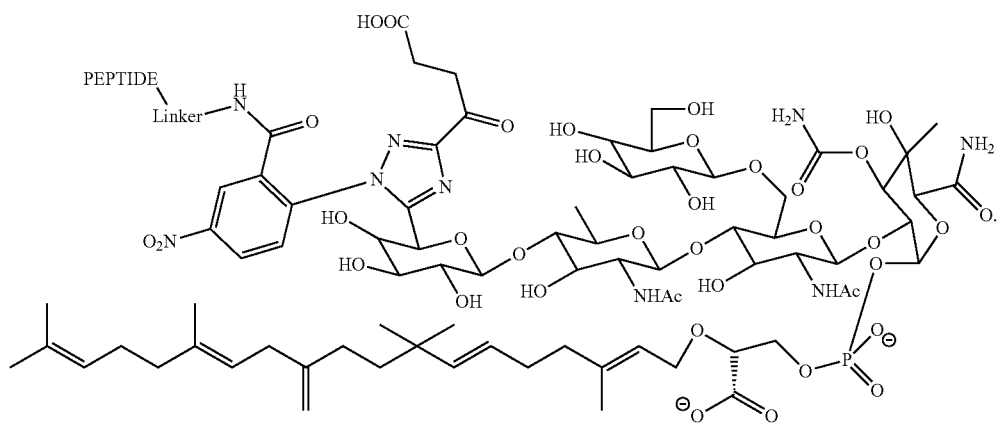

The molecular fragment shown below is present in all of peptides 1 to 17:

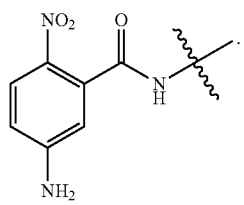

The general structure shown above for the peptide-Moenomycin A conjugates shows the nitrobenzene ring (as is present in all of peptides 1 to 17) attached to the Moenomycin skeleton.

Shown below are structures of peptide conjugates that have been synthesised.

Compound 20 (SEQ ID NO: 15)
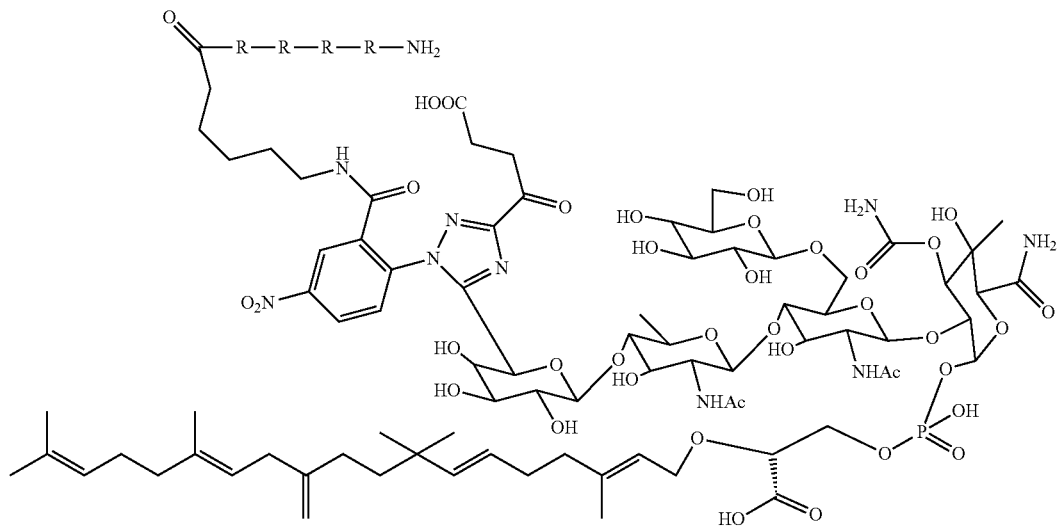
Compound 21 (SEQ ID NO: 1)
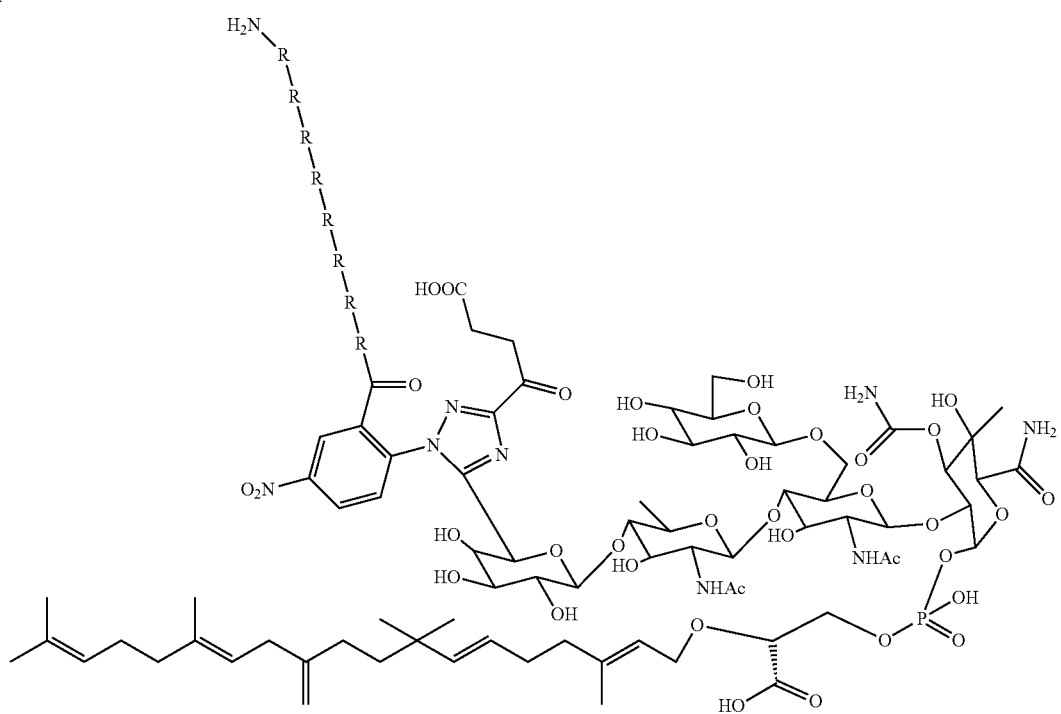

Compound 22 (SEQ ID NO: 1)
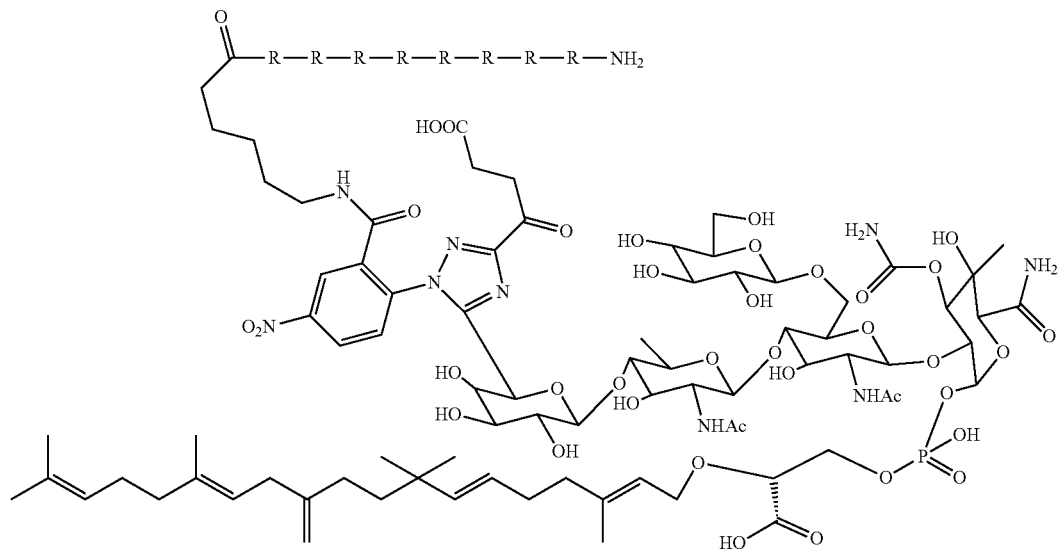
Compound 23 (SEQ ID NO: 1)
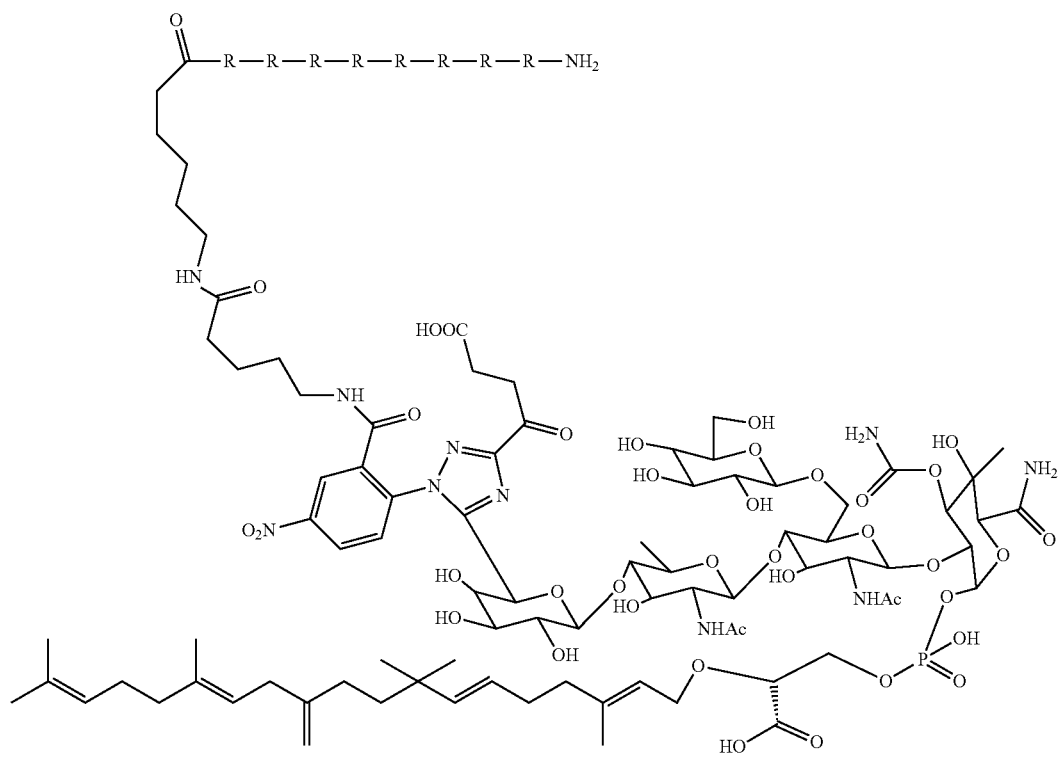

Compound 24 (SEQ ID NO: 16)
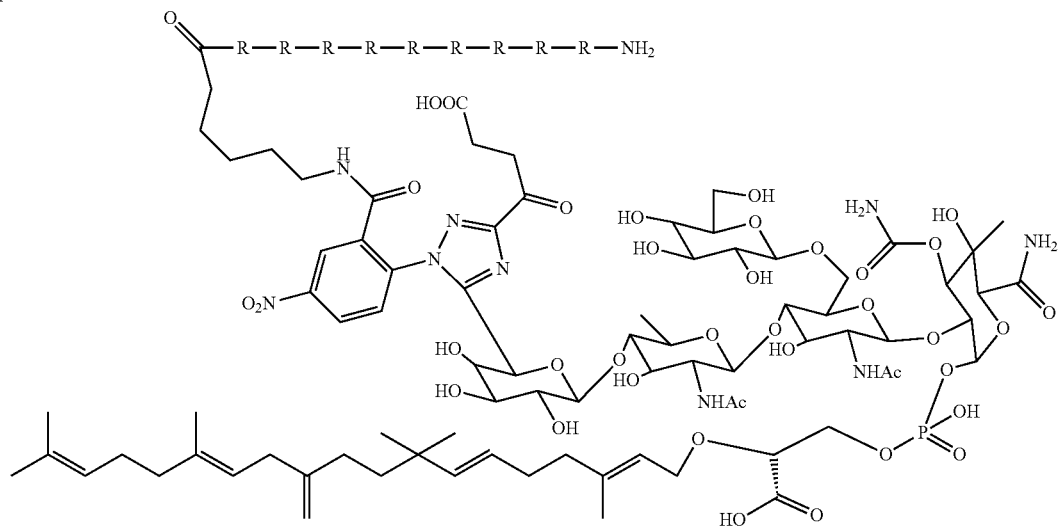
Compound 25 (SEQ ID NO: 17)
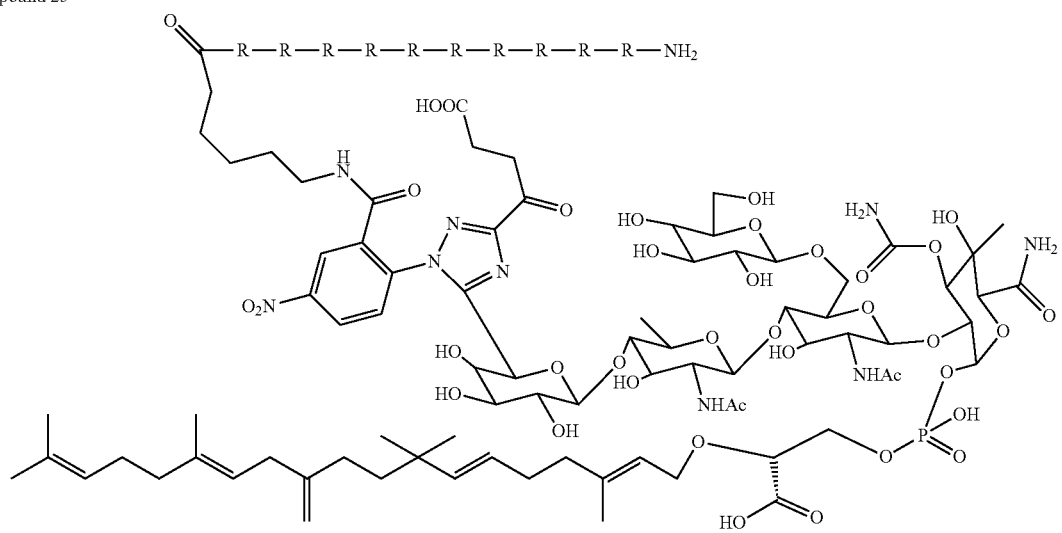
Compound 26 (SEQ ID NO: 18)
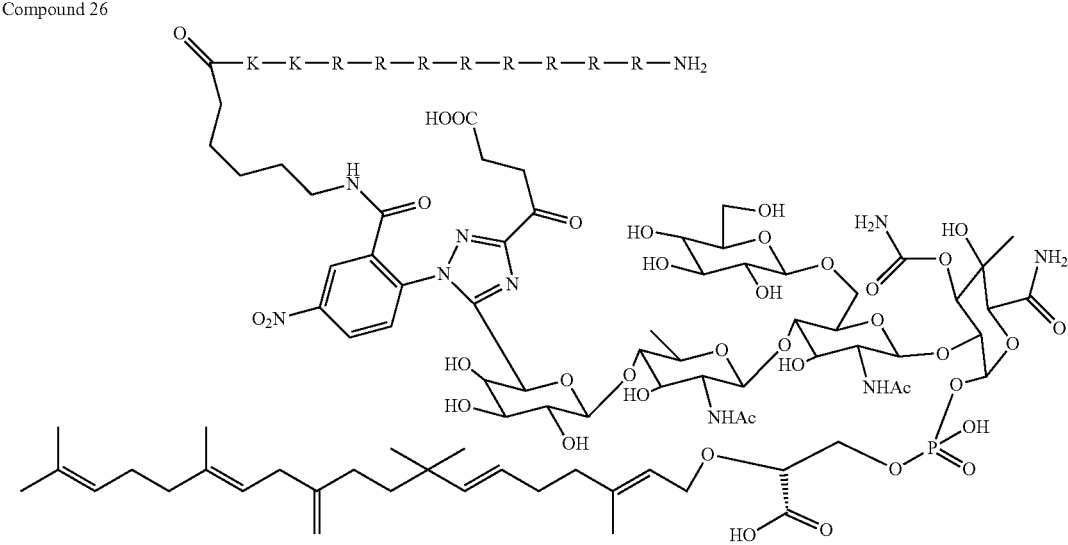

Compound 27 (SEQ ID NO: 4)
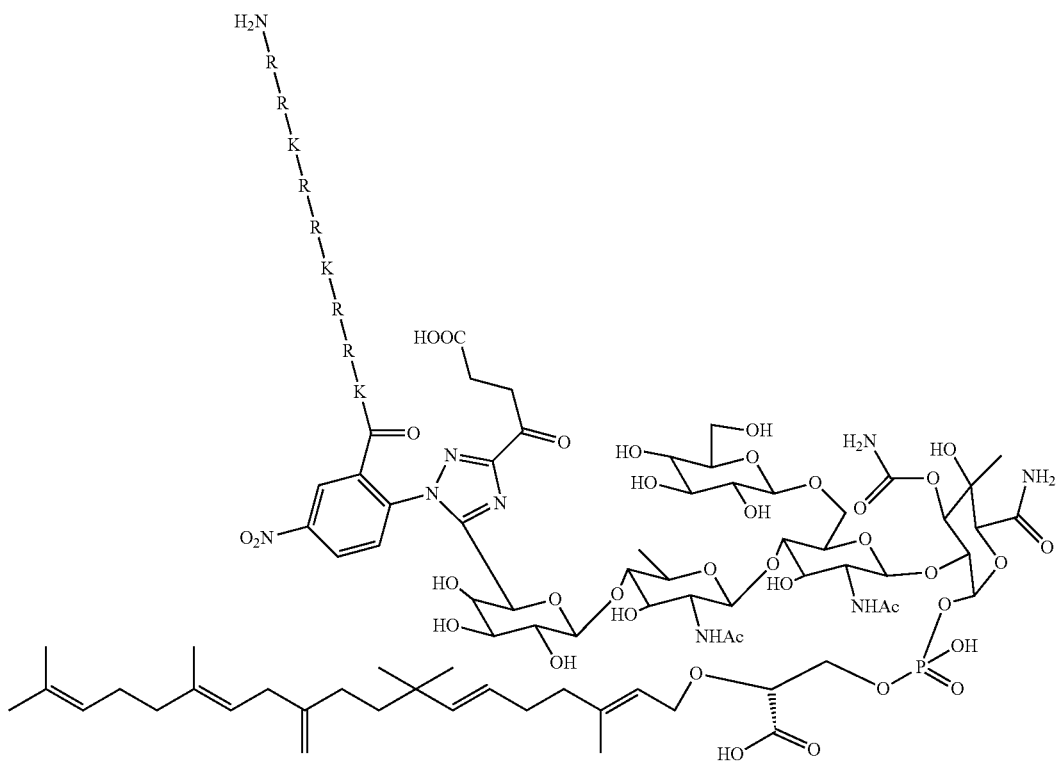
Compound 28 (SEQ ID NO: 4)
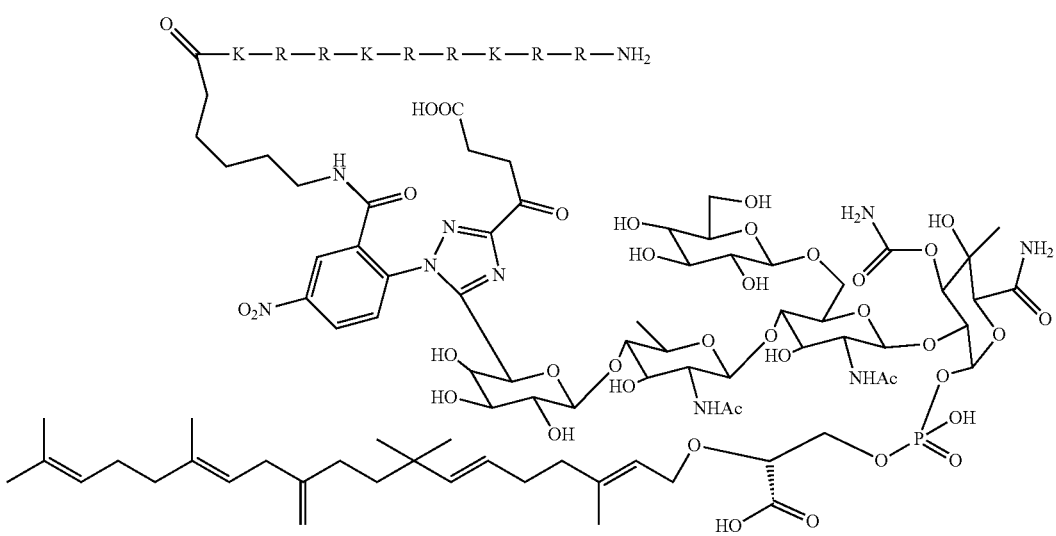

Compound 29 (SEQ ID NO: 4)
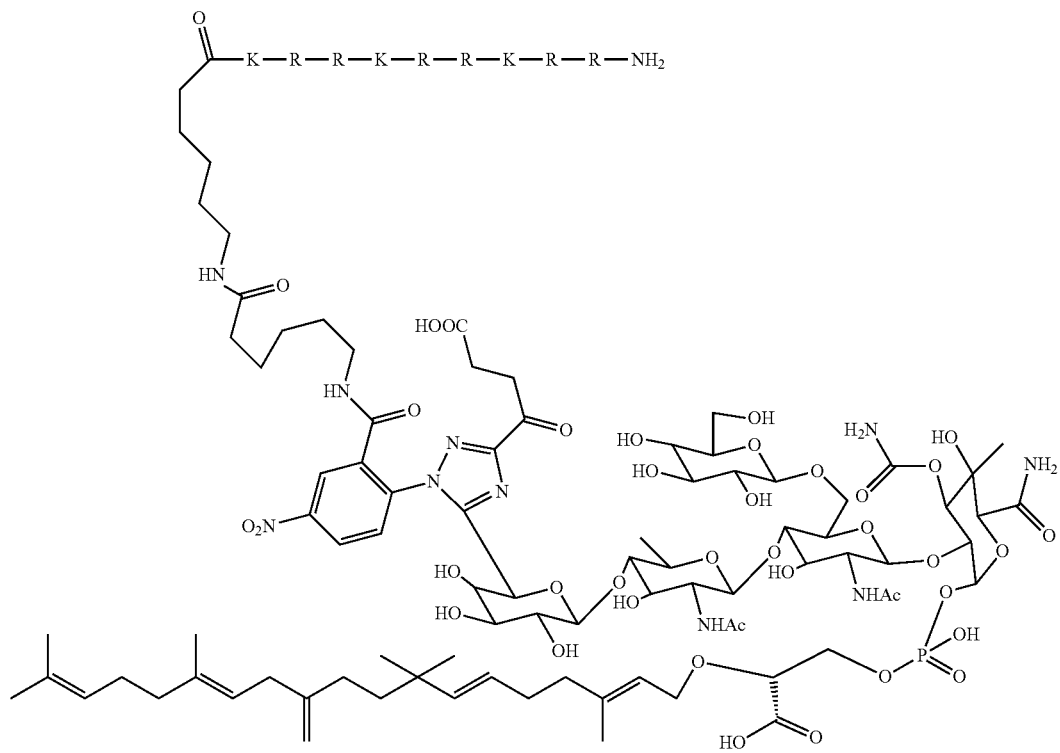
Compound 30 (SEQ ID NO: 14)
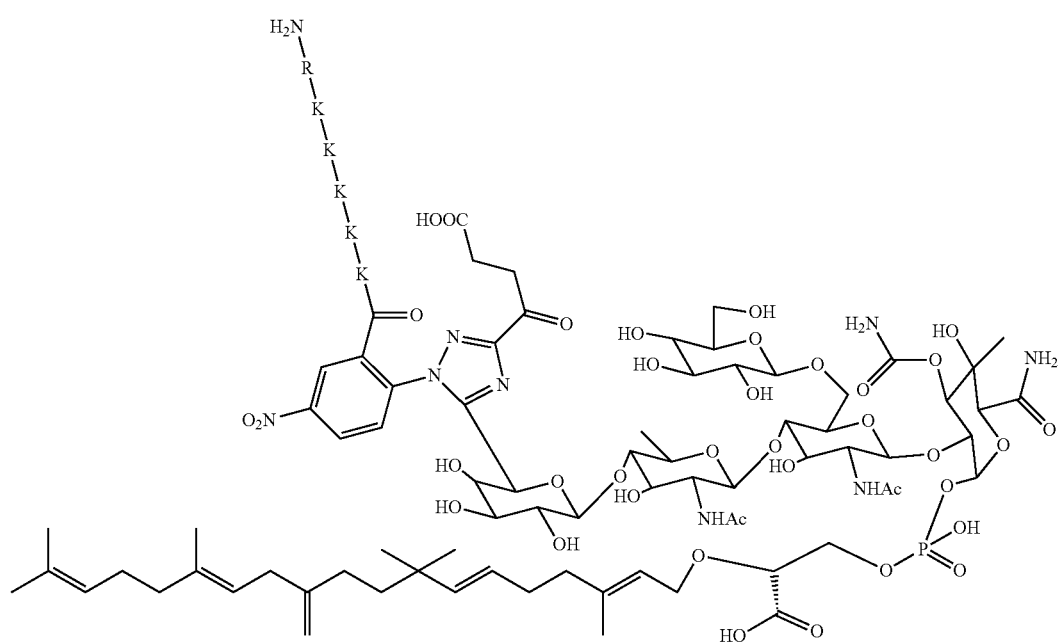

Compound 31 (SEQ ID NO: 14)
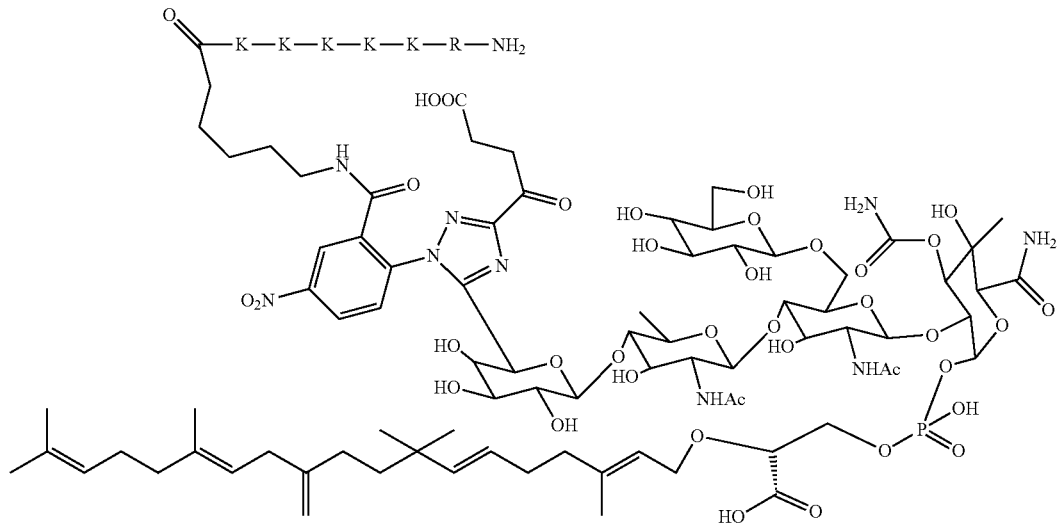
Compound 32 (SEQ ID NO: 14)
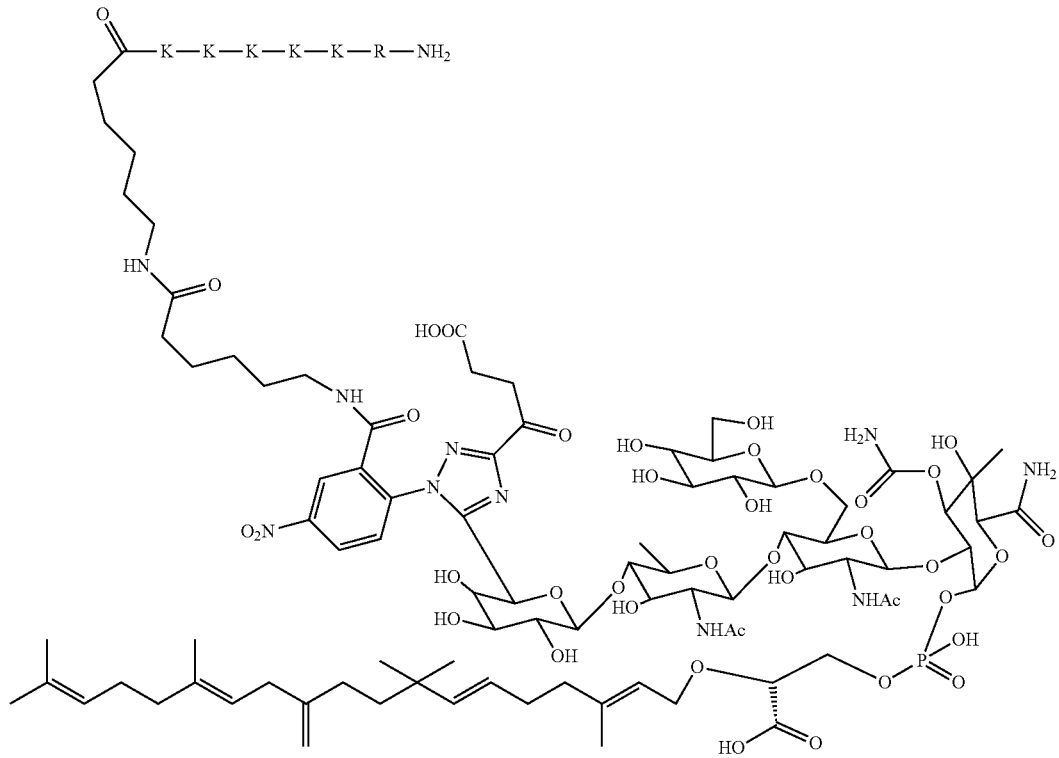

Compound 33 (SEQ ID NO: 21)
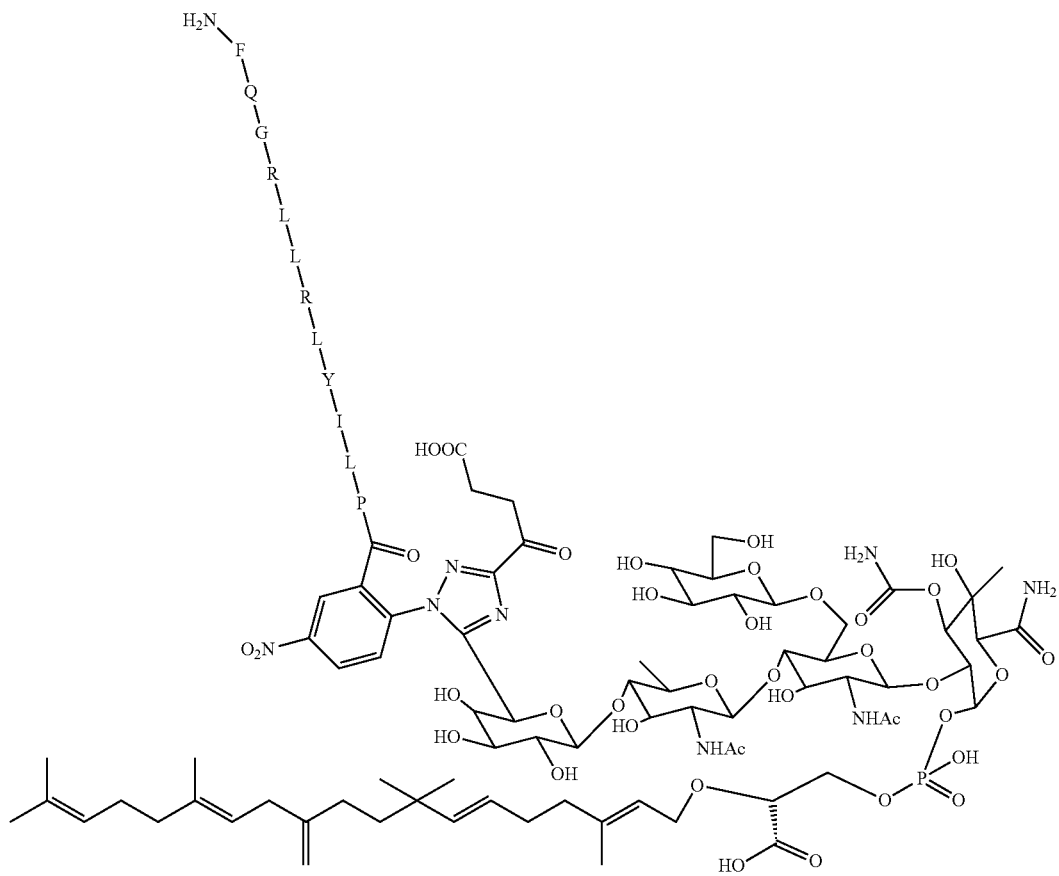
Compound 34
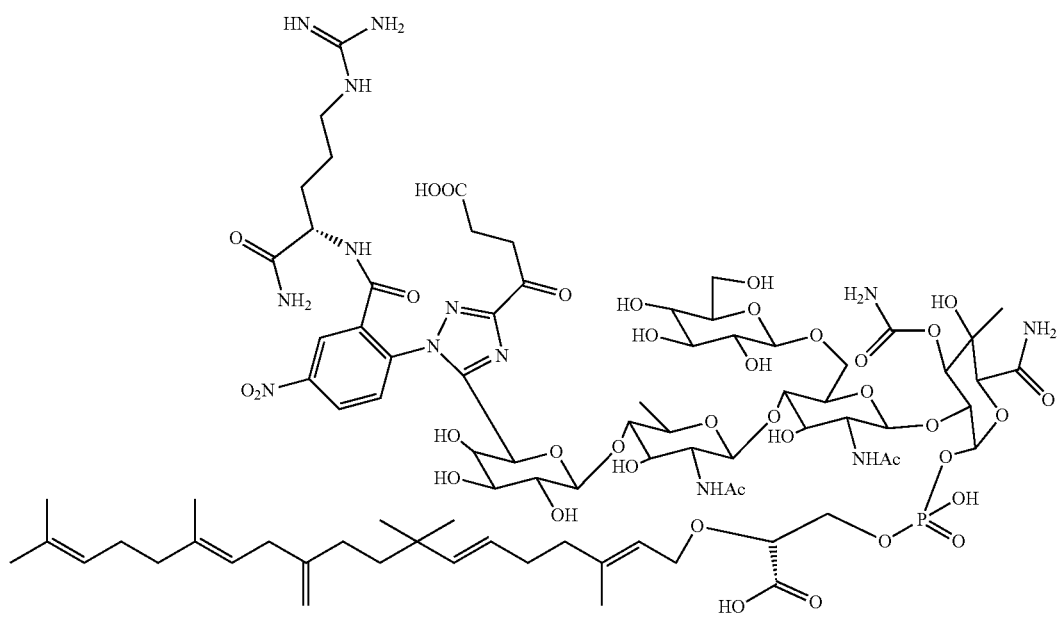

Example 9—Antibacterial Efficacy Test Results

| Test material | MIC | MBC |
|---|---|---|
| Organism: *A. baumannii* 19606 | | |
| Ampicillin | | |
| A | 128 μg/ml | Growth in all wells |
| B | 128 μg/ml | Growth in all wells |
| C | 128 μg/ml | Growth in all wells |
| Moenomycin A | | |
| A | 4 μg/ml | 8 μg/ml |
| B | 4 μg/ml | 8 μg/ml |
| C | 8 μg/ml | 8 μg/ml |
| Moenomycin A + Compound 5 | | |
| A | 4 μg/ml | 8 μg/ml |
| B | 4 μg/ml | 8 μg/ml |
| C | 4 μg/ml | 8 μg/ml |
| Compound 5 | | |
| A | Growth in all wells | Growth in all wells |
| B | Growth in all wells | Growth in all wells |
| C | Growth in all wells | Growth in all wells |
| Moenomycin A + Compound 6 | | |
| A | 2 μg/ml | 2 μg/ml |
| B | 2 μg/ml | 2 μg/ml |
| C | 2 μg/ml | 2 μg/ml |
| Compound 6 | | |
| A | 256 μg/ml | 256 μg/ml |
| B | 256 μg/ml | 256 μg/ml |
| C | 256 μg/ml | 256 μg/ml |
| Moenomycin A + Compound 7 | | |
| A | 4 μg/ml | 8 μg/ml |
| B | 4 μg/ml | 8 μg/ml |
| C | 4 μg/ml | 8 μg/ml |
| Compound 7 | | |
| A | Growth in all wells | Growth in all wells |
| B | Growth in all wells | Growth in all wells |
| C | Growth in all wells | Growth in all wells |
| Moenomycin A + Compound 8 | 2 | 16 |
| Compound 8 | Growth in all wells | Growth in all wells |
| Moenomycin A + Compound 9 | 16 | 128 |
| Compound 9 | Growth in all wells | Growth in all wells |
| Moenomycin A + Compound 10 | 16 | 128 |
| Compound 10 | Growth in all wells | Growth in all wells |
| Moenomycin A + Compound 11 | 16 | 32 |
| Compound 11 | Growth in all wells | Growth in all wells |
| Moenomycin A + Compound 12 | 4 | 8 |
| Compound 12 | Growth in all wells | Growth in all wells |
| Moenomycin A + Compound 13 | 16 | 16 |
| Compound 13 | Growth in all wells | Growth in all wells |
| Moenomycin A + Compound 15 | 8 | 32 |
| Compound 15 | Growth in all wells | Growth in all wells |
| Moenomycin A + Compound 16 | 2 | 64 |
| Compound 16 | Growth in all wells | Growth in all wells |
| Moenomycin A + Compound 17 | 8 | 64 |
| Compound 17 | Growth in all wells | Growth in all wells |
| Organism: *K. pneumonia* 700603 | | |
| Ampicillin | | |
| A | Growth in all wells | Growth in all wells |
| B | Growth in all wells | Growth in all wells |
| C | Growth in all wells | Growth in all wells |
| Moenomycin A | | |
| A | 64 μg/ml | 128 μg/ml |
| B | 64 μg/ml | 128 μg/ml |
| C | 64 μg/ml | 128 μg/ml |
| Moenomycin A + Compound 5 | | |
| A | 32 μg/ml | 16 μg/ml |
| B | 16 μg/ml | 8 μg/ml |
| C | 16 μg/ml | 16 μg/ml |

-continued

| Test material | MIC | MBC |
|---|---|---|
| Compound 5 | | |
| A | 128 µg/ml | 128 µg/ml |
| B | 64 µg/ml | 64 µg/ml |
| C | 64 µg/ml | 64 µg/ml |
| Moenomycin A + Compound 6 | | |
| A | 4 µg/ml | 4 µg/ml |
| B | 4 µg/ml | 4 µg/ml |
| C | 4 µg/ml | 4 µg/ml |
| Compound 6 | | |
| A | Growth in all wells | Growth in all wells |
| B | Growth in all wells | Growth in all wells |
| C | Growth in all wells | Growth in all wells |
| Moenomycin A + Compound 7 | | |
| A | 64 µg/ml | 64 µg/ml |
| B | 32 µg/ml | 32 µg/ml |
| C | 32 µg/ml | 32 µg/ml |
| Compound 7 | | |
| A | Growth in all wells | Growth in all wells |
| B | Growth in all wells | Growth in all wells |
| C | Growth in all wells | Growth in all wells |
| Moenomycin A + Compound 8 | 4 | 4 |
| Compound 8 | Growth in all wells | Growth in all wells |
| Moenomycin A + Compound 9 | 32 | 64 |
| Compound 9 | Growth in all wells | Growth in all wells |
| Moenomycin A + Compound 10 | 32 | 64 |
| Compound 10 | Growth in all wells | Growth in all wells |
| Moenomycin A + Compound 11 | 32 | 64 |
| Compound 11 | Growth in all wells | Growth in all wells |
| Moenomycin A + Compound 12 | 8 | 32 |
| Compound 12 | Growth in all wells | Growth in all wells |
| Moenomycin A + Compound 13 | 32 | 128 |
| Compound 13 | Growth in all wells | Growth in all wells |
| Moenomycin A + Compound 15 | 32 | 32 |
| Compound 15 | Growth in all wells | Growth in all wells |
| Moenomycin A + Compound 16 | 16 | 64 |
| Compound 16 | Growth in all wells | Growth in all wells |
| Moenomycin A + Compound 17 | 8 | 64 |
| Compound 17 | Growth in all wells | Growth in all wells |
| Organism: *P. aeruginosa* 27853 | | |
| Ampicillin | | |
| A | Growth in all wells | Growth in all wells |
| B | Growth in all wells | Growth in all wells |
| C | Growth in all wells | Growth in all wells |
| Moenomycin A | | |
| A | 256 µg/ml | Growth in all wells |
| B | 256 µg/ml | Growth in all wells |
| C | 256 µg/ml | Growth in all wells |
| Moenomycin A + Compound 5 | | |
| A | 32 µg/ml | 256 µg/ml |
| B | 32 µg/ml | 256 µg/ml |
| C | 32 µg/ml | 128 µg/ml |
| Compound 5 | | |
| A | 256 µg/ml | Growth in all wells |
| B | 256 µg/ml | 256 µg/ml |
| C | 256 µg/ml | 256 µg/ml |
| Moenomycin A + Compound 6 | | |
| A | 4 µg/ml | 16 µg/ml |
| B | 8 µg/ml | 32 µg/ml |
| C | 4 µg/ml | 16 µg/ml |

-continued

| Test material | MIC | MBC |
|---|---|---|
| Compound 6 | | |
| A | 256 µg/ml | 256 µg/ml |
| B | 256 µg/ml | 256 µg/ml |
| C | 256 µg/ml | 256 µg/ml |
| Moenomycin A + Compound 7 | | |
| A | 128 µg/ml | Growth in all wells |
| B | 128 µg/ml | Growth in all wells |
| C | 128 µg/ml | Growth in all wells |
| Compound 7 | | |
| A | Growth in all wells | Growth in all wells |
| B | Growth in all wells | Growth in all wells |
| C | Growth in all wells | Growth in all wells |
| Moenomycin A + Compound 8 | 16 | 64 |
| Compound 8 | Growth in all wells | Growth in all wells |
| Moenomycin A + Compound 9 | 128 | Growth in all wells |
| Compound 9 | Growth in all wells | Growth in all wells |
| Moenomycin A + Compound 10 | 128 | Growth in all wells |
| Compound 10 | Growth in all wells | Growth in all wells |
| Moenomycin A + Compound 11 | 64 | 128 |
| Compound 11 | Growth in all wells | Growth in all wells |
| Moenomycin A + Compound 12 | 32 | 64 |
| Compound 12 | Growth in all wells | Growth in all wells |
| Moenomycin A + Compound 13 | 64 | 256 |
| Compound 13 | Growth in all wells | Growth in all wells |
| Moenomycin A + Compound 15 | 128 | Growth in all wells |
| Compound 15 | Growth in all wells | Growth in all wells |
| Moenomycin A + Compound 16 | 256 | Growth in all wells |
| Compound 16 | Growth in all wells | Growth in all wells |
| Moenomycin A + Compound 17 | Growth in all wells | Growth in all wells |
| Compound 17 | Growth in all wells | Growth in all wells |
| Organism: *E. coli* 25922 | | |
| Ampicillin | 8 µg/ml | 8 µg/ml |
| Moenomycin A | 32 µg/ml | 128 µg/ml |
| Moenomycin A + Compound 5 | 16 µg/ml | 64 µg/ml |
| Compound 5 | 64 µg/ml | 128 µg/ml* |
| Moenomycin A + Compound 6 | 4 µg/ml | 8 µg/ml |
| Compound 6 | 256 µg/ml | Growth in all wells |
| Moenomycin A + Compound 7 | Not tested | Not tested |
| Compound 7 | Not tested | Not tested |
| Organism: *B. subtilis* 2410 | | |
| Ampicillin | 128 µg/ml | 256 µg/ml |
| Moenomycin A | 256 µg/ml | Growth in all wells |
| Moenomycin A + Compound 5 | 8 µg/ml | 64 µg/ml |
| Compound 5 | 32 µg/ml | 32 µg/ml |
| Moenomycin A + Compound 6 | 4 µg/ml | 64 µg/ml |
| Compound 6 | 32 µg/ml | 32 µg/ml |
| Moenomycin A + Compound 7 | Not tested | Not tested |
| Compound 7 | Not tested | Not tested |

Example 9—Antibacterial Efficacy Test Results for Conjugated Delivery Agents

| Compound number | B. subtilis 168 | | K. pnumoniae ATCC 700603 | | A. baumannii ATCC 19606 | | P. aeruginosa ATCC 27853 | |
|---|---|---|---|---|---|---|---|---|
| | MIC | MBC | MIC | MBC | MIC | MBC | MIC | MBC |
| Compound 20 | 32 | GAW | 64 | — | 32 | 64 | GAW | GAW |
| Compound 21 | — | — | 128 | GAW | 8 | 256 | 128 | GAW |
| Compound 22 | 16 | 32 | 64 | — | 32 | 64 | 256 | GAW |
| Compound 23 | 2 | 64 | 8 | 256 | 64 | 128 | 16 | 256 |
| Compound 24 | 2 | 64 | GAW | GAW | 32 | 64 | 256 | GAW |
| Compound 25 | 1 | 64 | GAW | 256 | 64 | 128 | 256 | 256 |
| Compound 26 | 4 | GAW | 16 | 64 | 8 | 32 | 128 | 256 |
| Compound 27 | — | — | GAW | GAW | 4 | 64 | 128 | GAW |
| Compound 28 | 8 | 64 | GAW | GAW | 64 | 128 | 256 | GAW |
| Compound 29 | — | — | 256 | GAW | 16 | 64 | 128 | GAW |
| Compound 30 | — | — | 64 | 64 | 4 | 32 | 64 | 128 |
| Compound 31 | 0.5 | 64 | 64 | 128 | 1 | — | 64 | 64 |
| Compound 32 | — | — | 64 | GAW | 2 | 8 | 128 | GAW |
| Compound 33 | — | — | GAW | GAW | 64 | GAW | GAW | GAW |
| Compound 34 | — | — | 64 | 64 | 4 | 256 | 256 | GAW |

| Compound number | S. Aureus ATCC 25922 | |
|---|---|---|
| | MIC | MBC |
| Compound 34 | 0.25 | — |

Example 10—Antibacterial Efficacy Test Results for Peptide Delivery Agents

| Peptide/anti-bacterial agent | B. subtilis 168 | | K. pnumoniae ATCC 700603 | | A. baumannii ATCC 19606 | | P. aeruginosa ATCC 27853 | |
|---|---|---|---|---|---|---|---|---|
| | MIC | MBC | MIC | MBC | MIC | MBC | MIC | MBC |
| Peptide 4 | 128 | GAW | GAW | GAW | GAW | GAW | GAW | GAW |
| Peptide 4 + Moenomycin A | 1 | GAW | 16 | 32 | 2 | 4 | 64 | 256 |
| Peptide 5 | 128 | GAW | GAW | GAW | GAW | GAW | GAW | GAW |
| Peptide 5 + Moenomycin A | 0.25 | 8 | 32 | GAW | 1 | 4 | 32 | 256 |
| Peptide 6 | 128 | 256 | GAW | GAW | GAW | GAW | GAW | GAW |
| Peptide 6 + Moenomycin A | 0.25 | 8 | 16 | GAW | 1 | 8 | 32 | GAW |
| Peptide 9 | GAW | GAW | GAW | GAW | GAW | GAW | GAW | GAW |
| Peptide 9 + Moenomycin A | 0.5 | GAW | 16 | 16 | 2 | 16 | 32 | 256 |
| Peptide 15 | GAW | GAW | GAW | GAW | GAW | GAW | GAW | GAW |
| Peptide 15 + Moenomycin A | 0.25 | 16 | 8 | 16 | 1 | 4 | 32 | 64 |

| Peptide/anti-bacterial agent | S. Aureus ATCC 25922 | |
|---|---|---|
| | MIC | MBC |
| Peptide 17 | 256 | — |
| Peptide 17 + Moenomycin A | 0.25 | — |

"GAW" = growth in all wells

Example 11—Toxicity Data for Unbound Delivery Agents

Wax Moth *Galleria mellonella*

In vivo toxicity tests were conducted for Compounds 1 to 19 using wax moth *Galleria mellonella*. No toxicity was observed below 40 mg/kg (24-96 hr, 100% survival).

Mammalian Cytotoxicity

Moenomycin A—no toxicity was observed up to 10 mg/mL.

Compound 8—no toxicity was observed up to 110 µg/mL.

Compound 6 did not affect the cell viability in the tumor cell line 786-0 in initial in vitro testing. Compound 6 was toxic in HeLa cells at 20 µg/ml.

Example 12—Toxicity Data for Covalent Conjugates of Moenomycin A Wax Moth *Galleria mellonella*

Compounds 26, 29, 32 were tested—no toxicity was observed below 80 mg/kg (24 hr, 100% survival).

Mammalian Cytotoxicity

In Vitro Testing in HeLa cells showed no toxicity up to the concentrations mentioned in the table below.

| Compound number | 100% survival in µM | 100% survival in µg/mL |
|---|---|---|
| 29 | 10 | 33.23 |
| 26 | 2 | 6.42 |
| 32 | 10 | 27.98 |

Abbreviations

ACN=Acetonitrile
Boc=tert-butyloxycarbonyl
DCM=dichloromethane
DIBAL=diisobutylaluminium hydride
DIPEA=N,N-diisopropylethylamine
DMAP=4-dimethylaminopyridine
DMF=N,N-dimethylformamide
eq.=equivalents
Et=ethyl
h=hour(s)
HCl=hydrochloric acid
HPLC=high performance liquid chromatography
IR=infra red (in relation to spectroscopy)
MBC=minimum bactericidal concentration
mcpba=meta-chloroperoxybenzoic acid
Me=methyl
MIC=minimum inhibitory concentration
min.=minute(s)
MS=mass spectrometry
PAMAM=polyamidoamine
RP=reverse phase
rt/RT=room temperature
THF=tetrahydrofuran
TFA=trifluoroacetic acid Prefixes n-, s-, t- and tert- have their usual meanings: normal, secondary, iso, and tertiary.

---

The invention claimed is:

1. A combination of an antibacterial agent or a derivative thereof and a delivery agent, wherein the delivery agent is a compound of formula I, $$A^1-D^1-(-x)_n \qquad I$$

or a pharmaceutically-acceptable salt thereof, wherein $A^1$ represents a hydrogen atom, a terminating group or the antibacterial agent or derivative thereof; X represents a fragment comprising a group selected from —NH$_2$, boronic acid and a boronic acid derivative; n is 2 or more; and $D^1$ represents a dendrimer fragment according to any one of formulae A to F:

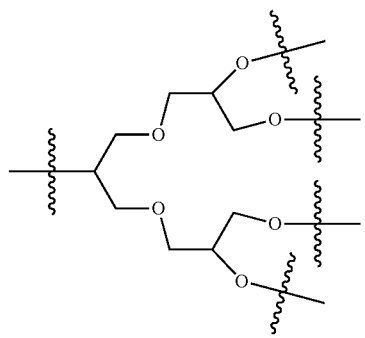

A

B

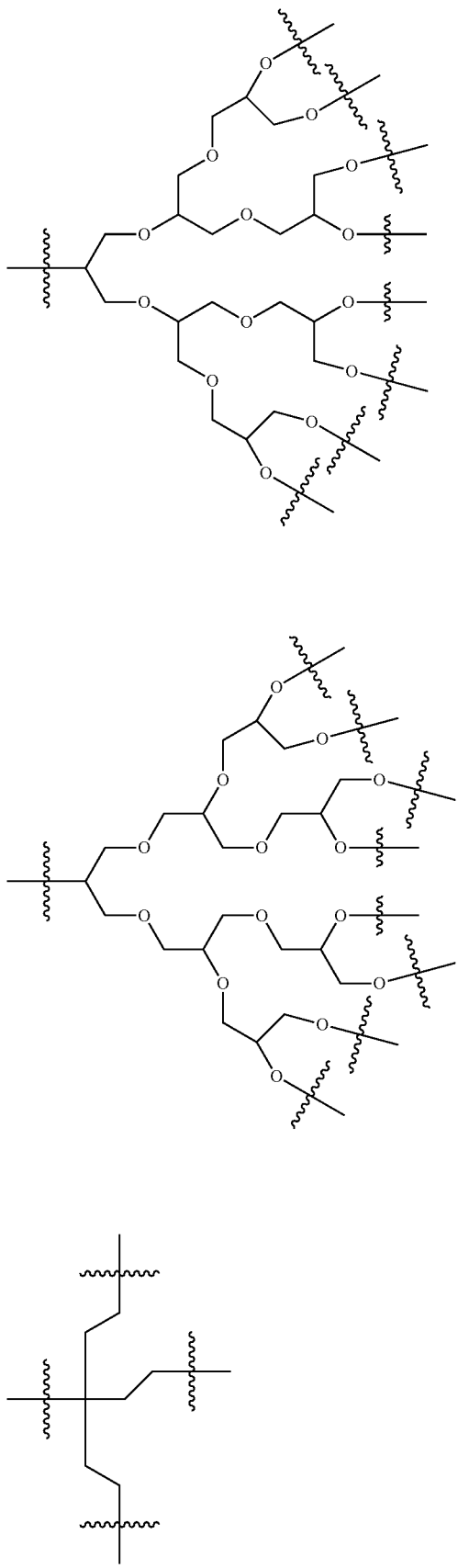

C

D

E

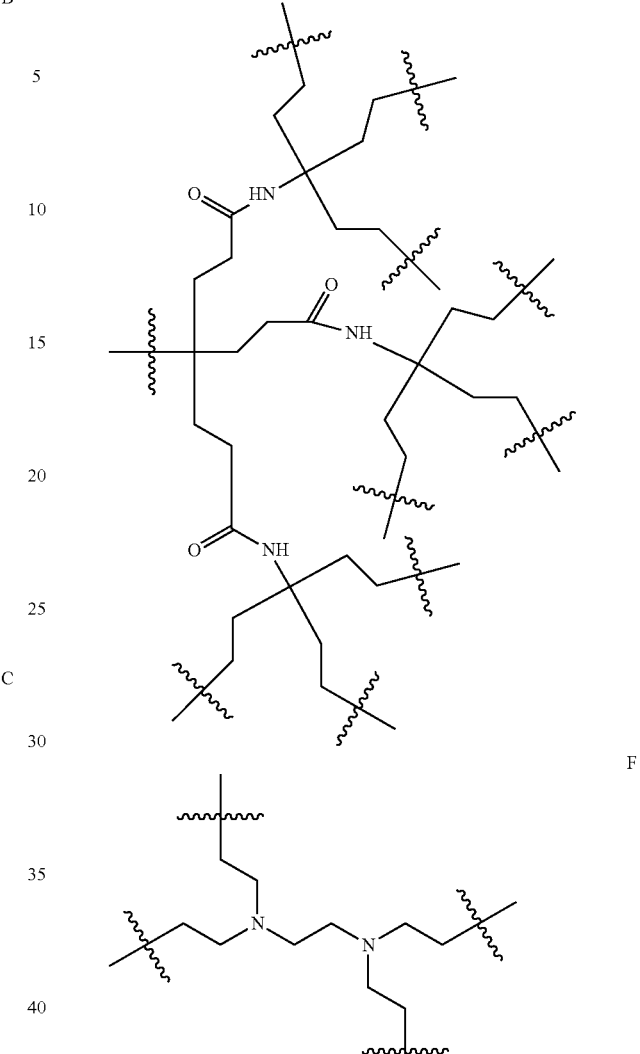

F wherein, for the dendrimer fragments of formula A to E, the single wavy line on the left-hand side of the structure corresponds to the point of attachment of the $A^1$ group and the other wavy lines correspond to the points of attachment of the requisite X groups; and wherein, for the dendrimer fragment of formula F, all of the wavy lines represent points of attachment of the requisite X groups, and $A^1$ represents hydrogen and is incorporated into formula F.

2. The combination according to claim 1, wherein the antibacterial agent is a molecule or fragment that modulates the activity of a penicillin binding protein.

3. The combination according to claim 1, wherein the antibacterial agent is an inhibitor of a glycosyltransferase enzyme.

4. The combination according to claim 1, wherein the antibacterial agent is a molecule or fragment that inhibits the synthesis or repair of bacterial cell walls.

5. The combination according to claim 1, wherein the delivery agent is capable of binding to one or more structures on a bacterial cell membrane via the formation of one or more covalent bonds with said structures, or via the formation of one or more hydrogen bonds with said structures.

6. The combination according to claim 1, wherein the delivery agent comprises one or more functional groups independently selected from the list consisting of boronic acids, boronic acid derivatives, primary amines, amidines, amides, and salts thereof.

7. The combination according to claim 6, wherein the each of the one or more functional groups is independently selected from the list consisting of boronic acids, boronic acid derivatives, primary amines, amidines, guanidines, amides, ureas, and acid addition salts thereof.

8. The combination according to claim 6, wherein the delivery agent comprises at least four of said functional groups.

9. The combination according to claim 1, wherein the delivery agent is a compound of any one of formulae II to VII:

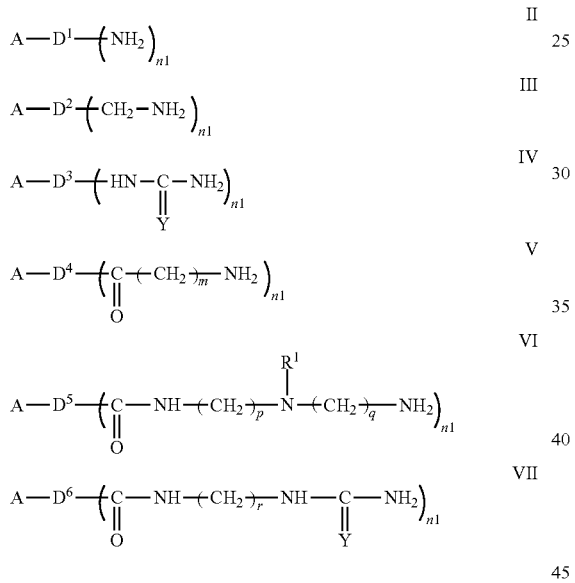

or a pharmaceutically-acceptable salt thereof, wherein each A independently represents a hydrogen atom, a terminating group or an antibacterial agent (or a derivative thereof); $D^1$ to $D^6$ each represent a dendrimer fragment according to any one of formulae A to F:

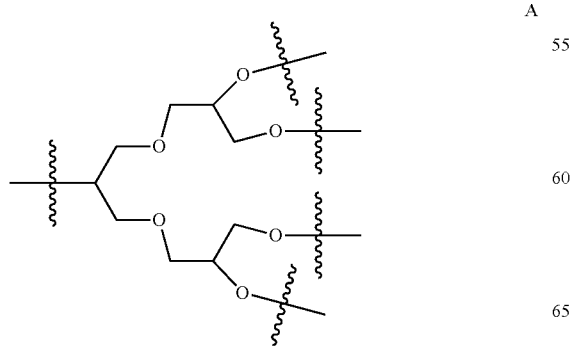

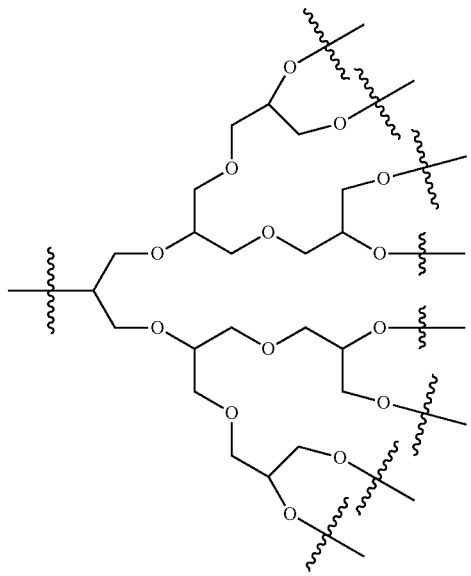

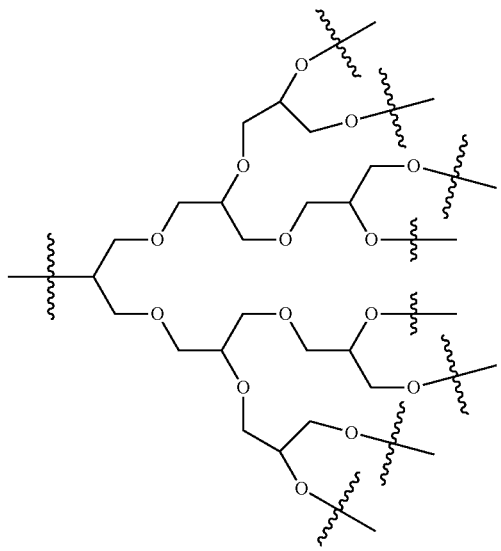

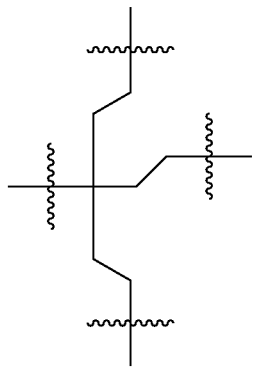

-continued

E

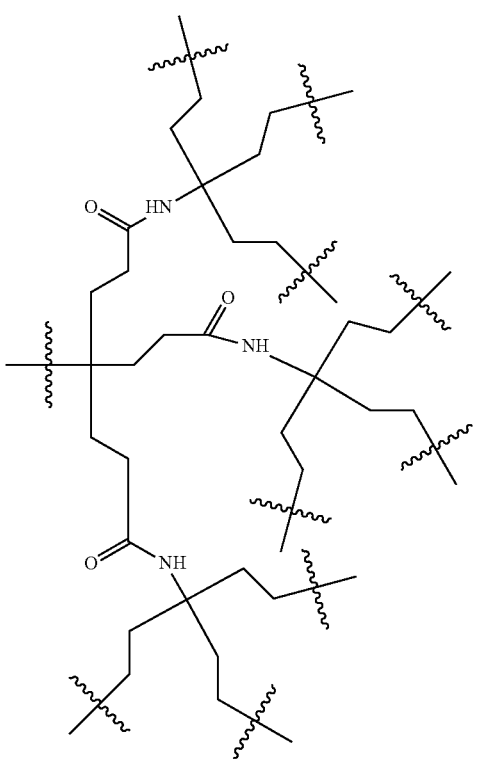

F

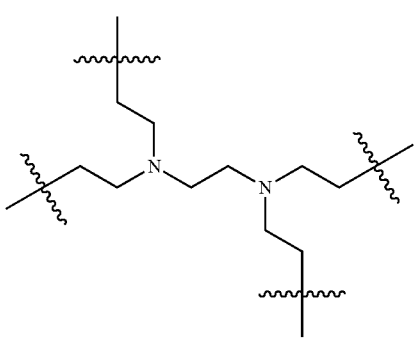

wherein, for the dendrimer fragments of formula A to E, the single wavy line on the left-hand side of the structure corresponds to the point of attachment of the A group and the other wavy lines correspond to the points of attachment of the groups shown in parentheses in formulae II to VII; and wherein, for the dendrimer fragment of formula F, all of the wavy lines represent points of attachment of the groups shown in parentheses in formulae II to VII, and A represents hydrogen and is incorporated into formula F; Y represents O, NH or S; each n1 is 2 or more; m, p, q and r each independently represent from 1 to 8; and $R^1$ represents a $C_{1-6}$ alkyl group; or wherein the delivery agent is a compound of formulae VIIIa, VIIIb or IX:

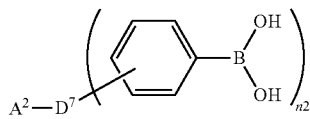

VIIIa

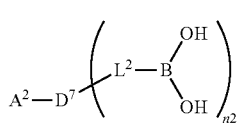

VIIIb

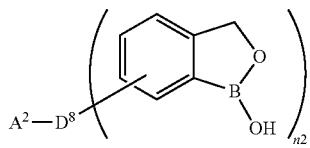

IX wherein each $A^2$ independently represents an antibacterial agent (or a derivative thereof), $L_2$ represents aliphatic linker; $D^7$ and $D^8$ independently represent a direct bond or a dendrimer fragment of any one of formulae A to E above and to which the boron-containing groups shown are attached, n2 is 1 or more, wherein, for compounds of formulae VIIIa, VIIIb and IX, the single wavy line on the left-hand side of each structure in formulae A to E corresponds to the point of attachment of the $A^2$ group and the other wavy lines correspond to the points of attachment of the requisite boronic acid or boric acid-containing portions of the delivery agent;

and optionally wherein $D^7$ and $D^8$ are attached to the boronic acid or boric acid portions of the compound of formula VIIIa, VIIIb and IX via a linker group.

10. The combination according to claim 1, wherein the delivery agent is a compound selected from the group consisting of:

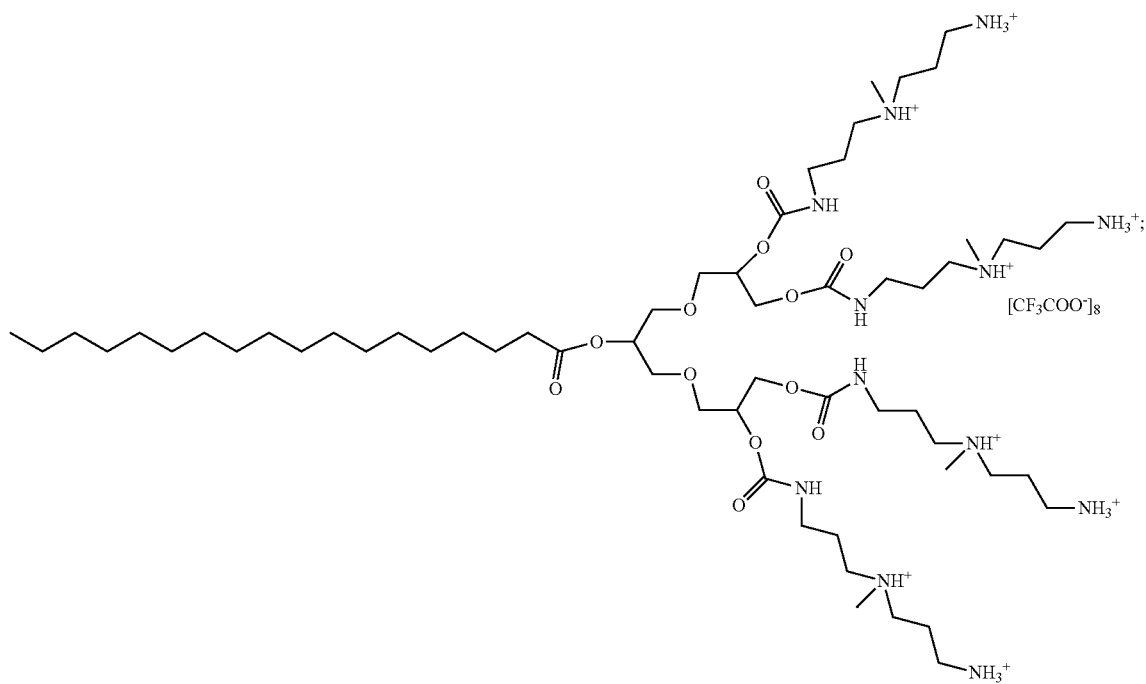
and
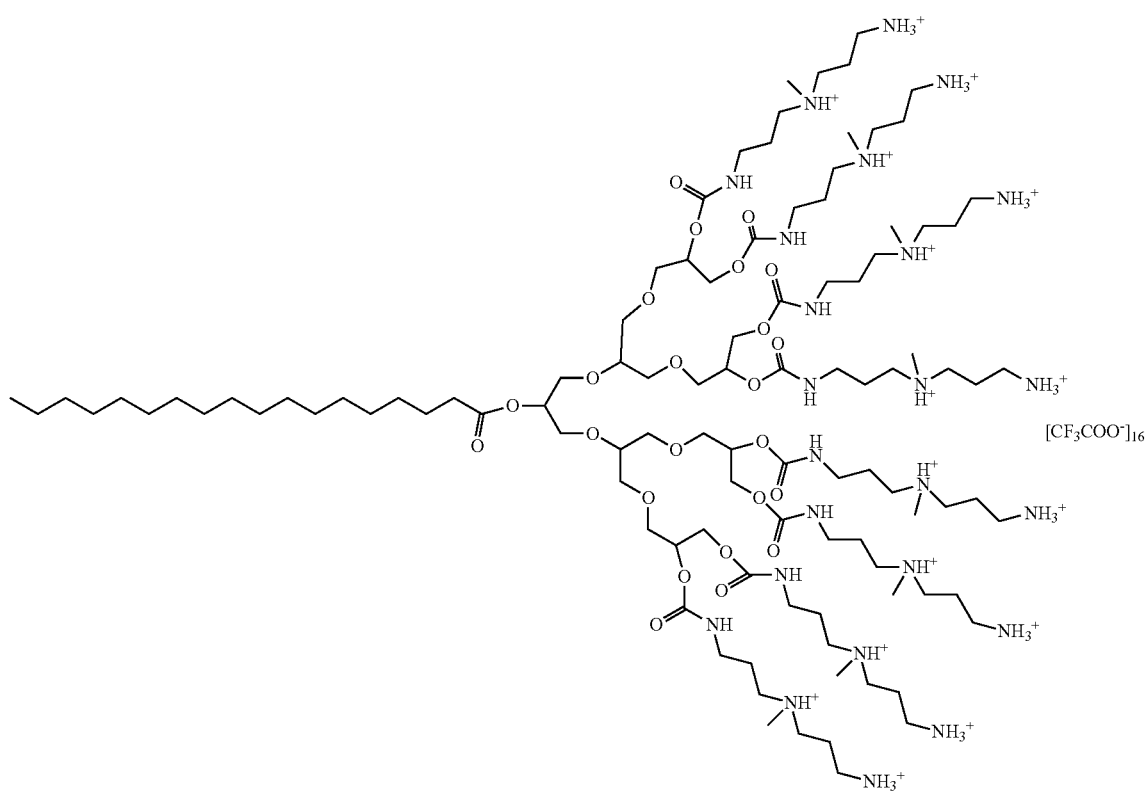

-continued

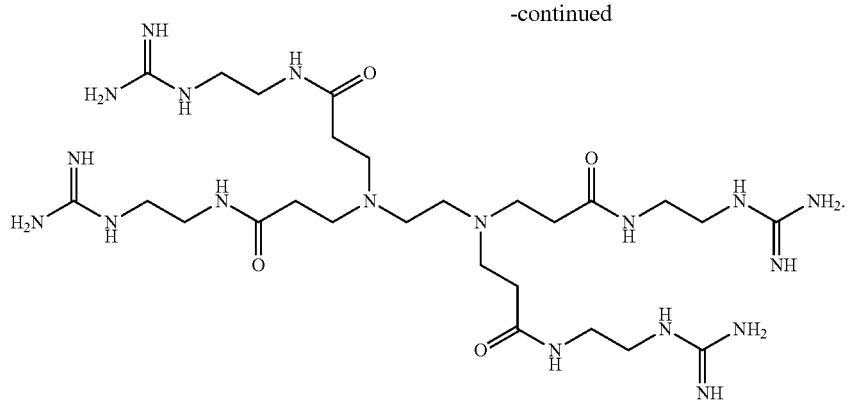

11. The combination according to claim 1, wherein the delivery agent is covalently bonded to the antibacterial agent.

12. The combination according to claim 1, wherein the antibacterial agent is a glycopeptide or a phosphoglycolipid molecule or fragment.

13. The combination according to claim 1, wherein the antibacterial agent is selected from the group consisting of moenomycin, moenomycin derivatives, vancomycin, vancomycin derivatives, β-lactam antibiotics and derivatives thereof.

14. The combination according to claim 13, wherein the antibacterial agent is a moenomycin A or a derivative thereof which is covalently bound to the delivery agent:
   (i) such that the delivery agent and any associated linker replaces part or all of the 2-amido-cyclopentane-1,3-dione portion of the moenomycin or derivative thereof;
   (ii) via the moenocinol portion of the moenomycin or derivative thereof;
   (iii) such that the delivery agent and any associated linker replaces part or all of the moenocinol portion of the moenomycin or derivative thereof; or
   (iv) via the 2-amino-cyclopentane-1,3-dione portion of the moenomycin or derivative thereof.

15. A pharmaceutical formulation comprising the combination of claim 1 in admixture with a pharmaceutically acceptable adjuvant, diluent or carrier.

16. A method of treating a bacterial infection caused by *Acinetobacter, Staphylococcus, Klebsiella, Pseudomonas, Escherichia*, or *Bacillus*, which method comprises administration of a therapeutically effective amount of a combination as defined in claim 1 to a subject in need thereof.

17. The combination according to claim 1, wherein n is from 2 to 20.

18. The combination according to claim 9, wherein each n1 is from 2 to 20.

19. The combination according to claim 9, wherein $L_2$ represents a $C_{1-6}$ alkyl chain.

\* \* \* \* \*